US006495556B2

(12) United States Patent
Uckun et al.

(10) Patent No.: US 6,495,556 B2
(45) Date of Patent: Dec. 17, 2002

(54) DIMETHOXY QUINAZOLINES FOR TREATING DIABETES

(75) Inventors: Fatih M. Uckun, White Bear Leak, MN (US); Elise A. Sudbeck, St. Paul, MN (US); Marina Cetkovic, Maplewood, MN (US); Ravi Malaviya, Shoreview, MN (US); Xing-Ping Liu, Minneapolis, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/812,098

(22) Filed: Mar. 19, 2001

(65) Prior Publication Data

US 2001/0044442 A1 Nov. 22, 2001

Related U.S. Application Data

(63) Continuation of application No. 09/378,093, filed on Aug. 20, 1999.
(60) Provisional application No. 60/097,365, filed on Aug. 21, 1998, and provisional application No. 60/097,359, filed on Aug. 21, 1998.

(51) Int. Cl.$^7$ .............................................. A61K 31/52
(52) U.S. Cl. .................................................. 514/266.4
(58) Field of Search ....................................... 514/266.4

(56) References Cited

U.S. PATENT DOCUMENTS

| 4,322,420 A | 3/1982 | Kobayashi et al. ......... 424/251 |
| 4,343,940 A | 8/1982 | Kreighbaum et al. ....... 544/283 |
| 4,464,375 A | 8/1984 | Kobayashi et al. ......... 424/251 |
| 5,710,158 A | 1/1998 | Myers et al. ................ 514/259 |
| 5,712,395 A | 1/1998 | App et al. ................... 544/344 |
| 5,770,599 A | 6/1998 | Gibson ..................... 514/228.2 |
| 5,770,603 A | 6/1998 | Gibson ....................... 514/259 |
| 5,792,771 A | 8/1998 | App et al. ................... 514/259 |
| 5,798,374 A | 8/1998 | Tang et al. ................. 514/369 |

FOREIGN PATENT DOCUMENTS

| WO | WO 95/03701 | 2/1995 |
| WO | WO 95/15758 | 6/1995 |
| WO | WO 96/09294 | 3/1996 |
| WO | WO 96/18639 | 6/1996 |
| WO | WO 96/40648 | 12/1996 |
| WO | WO 97/03069 | * 1/1997 |
| WO | WO 97/03358 | 1/1997 |
| WO | WO 97/30035 | 8/1997 |

OTHER PUBLICATIONS

Berg, R.J. et al., "Defective Global Genome Repair in XPC Mice is Associated with Skin Cancer Susceptibility But Not with Sensitivity to UVB Induced Erythema and Edema", *The Journal of Investigative Dermatology*, vol. 110, No. 4, pp. 405–409 (Apr. 1998).

Bohm, H., "The development of a simple empirical scoring function to estimate the binding constant for a protein–ligand complex of known three–dimensional structure",*Journal of Computer–Aided Molecular Design*, vol. 8, No. 3, pp. 243–256 (1994).

Bridges, A.J. et al., "Tyrosine kinase inhibitors. 8. An unusually steep structure–activity relationship for analogues of 4 – (3–bromoanilino) –6, 7–dimethoxyquinazoline (PD 153035), a potent inhibitor of the epidermal growth factor receptor", *Journal of Medicinal Chemistry*, vol. 39, pp. 267–276 (1996).

Budesinsky, Z. et al., "A new synthesis of the quinazoline nucleus", *Collection Czechoslov Chem. Commun.*, vol. 37, No. 8, pp. 2779–2785 (1972).

Bushkin, I. et al., "Alterations in Insulin Receptor Kinase Activity During Differentiation of H1–60 Cells", *Biochemical and Biophysical Research Communications*, vol. 172, No. 2, pp. 676–682 (Oct. 30, 1990).

Cerutti, P.A. et al., "Inflammation and Oxidative Stress in Carcinogenesis",*Cancer Cells*, vol. 3, No. 1, pp. 1–7 (Jan. 1991).

D'Cruz, O.J. et al., "Spermicidal Activity of Metallocene Complexes Containing Vanadium (IV) in Humans", *Biology of Reproduction*, vol. 58, No. 6, pp. 1515–1626 (Jun. 1998).

Danial, N.N. et al., "Jak–STAT Signaling Induced by the v–abl Oncogene", *Science*, vol. 269, pp. 875–1877 (Sep. 29, 1995).

Demoulin, J. et al., "A Single Tyrosine of the Interleukin–9 (IL–9) Receptor is Required for STAT Activation, Antiapoptotic Activity, and Growth Regulation by IL–9", *Molecular and Cellular Biology*, vol. 16, No. 9, pp. 4710–4716 (Sep. 1996).

Devary, Y. et al., "The Mammaliam Ultraviolet Response is Triggered by Activation of Src Tyrosine Kinases", *Cell*, vol. 71, pp. 1081–1091 (Dec. 24, 1992).

Fetter, J. et al., "Electron deficient heteroaromatic ammonioamidates–XVIa–The Synthesis and photochemistry of ethyl N–(2–methyl–4–metehylene—6, 7–methylenedioxy–3, 4–dihydro–3–quinazolinyl)–N–phenylcarbamate", *Tetrahedron*, vol. 34, No. 16, pp. 2557–2563 (1978).

Fujii, H. et al., "Recording of mitochondrial transmembrane potential and volume in cultured rat osteoclasts by confocal laser scanning microscopy", *The Histrochemical Journal*, vol. 29, No. 8, pp. 571–581 (Aug. 1997).

(List continued on next page.)

*Primary Examiner*—Mukund J. Shah
*Assistant Examiner*—Hong Liu
(74) *Attorney, Agent, or Firm*—Merchant & Gould P.C.

(57) ABSTRACT

The invention provides novel JAK-3 inhibitors that are useful for treating leukemia and lymphoma. The compounds are also useful to treat or prevent skin cancer, as well as sunburn and UVB-induced skin inflammation. In addition, the compounds of the present invention prevent the immunosuppressive effects of UVB radiation, and are useful to treat or prevent autoimmune diseases, inflammation, and transplant rejection. The invention also provides pharmaceutical compositions comprising compounds of the invention, as well as therapeutic methods for their use.

1 Claim, 55 Drawing Sheets

OTHER PUBLICATIONS

Gosh, S. et al., "alpha–Cyano–Beta–hydroxy–Beta–methyl–N–(4–(trifluoromethoxy) phenyl)) Propenamide: An Inhibitor of the Epidermal Growth Factor Receptor Tyrosine Kinase with Potent Cytotoxic Activity against Breast Cancer Cells", *Clinical Cancer Research*, vol. 4, No. 11, pp. 2657–2668 (Nov. 1998).

Gilchrest, B.A. et al., "The human sunburn reaction: Histologic and biochemical studies", *Journal of the American Academy of Dermatology*, vol. 5., No. 4, pp. 411–422 (Oct. 1981).

Goodman, P.A. et al., "Role of tyrosine kinases in induction of the c–jun proto–oncogene in irradiated B–lineage lymphoid cells", *Journal of Biological Chemistry*, vol. 273, No. 28, pp. 17742–17748 (1998).

Goodwin, J.S., "Immunologic Effects of Nonsteroidal Anti-Inflammatory Drugs", *The American Journal of Medicine*, pp. 7–15 (Oct. 15, 1984).

Grewe, M. et al., "Analysis of the Mechanism of Ultraviolet (UV) B Radiation–Induced Prostaglandin E2 Synthesis by Human Epidermoid Carcinoma Cells", *The Journal of Investigative Dermatology*, vol. 101, No. 4, pp. 528–531 (Oct. 1993).

Gupta, N. et al, "Delayed manifestation of ultraviolet reaction in the guineapig caused by anti–inflammatory drugs", *British Journal of Pharmacology*, vol. 47, pp. 240–24 8 (1973).

Gurniak, C.B. et al., "Murine JAK3 is Preferentially Expressed in Hematopoietic Tissues and Lymphocyte Precursor Cells", *Blood*, vol. 87, No. 8, pp. 3151–3160 (Apr. 15, 1996).

Hall, E.J. et al., "Basis Radiobiology", *American Journal of Clinical Oncology*, vol. 11, No. 3, pp. 220–252 (Jun. 1988).

Hanissian, S.H. et al., "Jak3 Is Associated with CD40 and Is Critical for CD40 Introduction of Gene Expression in B Cells", *Immunity*, vol. 6, No. 4, pp. 379–387 (Apr. 1997).

Hawk, J.L. et al., "Responses of Normal Skin to Ultraviolet Radiation", In: *The Science of Photomedicine*, Chapter 8, Edited by J.D. Regan et al., Plenum Press, New York, pp. 219–260 (1982).

Hial, V. et al., "Alteration of Tumor Growth by Aspirin and Indomethacin: Studies with Two Transplantable Tumors in Mouse", *European Journal of Pharmacology*, vol. 37, pp. 367–376 (1976).

Higashino, T. et al., "Reactions of the anion of quinazoline reissert compound (3–benzoyl–3, 4– dihydro–4– quinazolinecarbonitrile) with electrophiles", *Chem. Pharm. Bull.*, vol. 33, No. 3, pp. 950–961 (1985).

Hoffman, S.M. et al., "JAK3 Maps to Human Chromosome 19p12 within a Cluster of Proto–onocogenes and Transcription Factors", *Genomics*, vol. 43, pp. 109–111 (1997).

Horvath, C.M. et al., "The state of the STATs: recent developments in the study of signal transduction to the nucleus", *Current Opinion in Cell Biology*, vol. 9, No. 2, pp. 233–239 (Apr. 1997).

Hruza, L.L. et al., "Mechanisms of UV–Induced Inflammation", *The Journal of Investigative Dermatology*, vol. 100, No. 1, Supplement, pp. 35S–41S (Jan. 1993).

Hubbard, S.R. et al., "Crystal structure of the tyrosine kinase domain of the human insulin receptor", *Nature*, vol. 372, No. 6508, pp. 746–754 (Dec. 1994).

Ife, R.J. et al., "Reversible inhibitors of the gastric (H+/K+) –ATPase. 5. Substituted 2,4–diaminoquinazolines and thienopyrimidines", *Journal of Medicinal Chemistry*, vol. 38, pp. 2763–2773 (1995).

Ihle, J.N., "Janus kinases in cytokine signaling", *Philosophical Transactions: Biological Sciences*, vol. 351, No. 1336, pp. 159–166 (Feb. 29, 1996).

Ihle, J.N., "The Janus Protein Tyrosine Kinase Family and its Role in Cytokine Signaling", *Advances in Immunology*, vol. 60, Academic Press, Inc., San Diego, CA, pp. 1–35 (1995).

Jurlander, J. et al., "Characterization of Interleukin–10 Receptor Expression on B–Cell Chronic Lymphocytic Leukemia Cells", *Blood*, vol. 89, No. 11, pp. 4146–4152 (Jun. 1, 1997).

Kaneko, S. et al., "Rescue by cytokines of apoptotic cell death induced by IL–2 deprivation of human antigen–specific T cell clones", *Clinical and Experimental Immunology*, vol. 109, No. 1, pp. 185–193 (Jul. 1997).

Kang–Rotondo, C.H. et al., "Enhanced keratinocyte prostaglandin synthesis after UV injury is due to increased phospholipase activity", *American Journal of Physiology*, vol. 264, No. 2, pp. C396–C401 (Feb. 1993).

Kaplan, G.C. et al., "Insulin Receptor Overexpression in a Human Pre–B Acute Lymphocytic Leukemia Cell Line with A t (1;19) Chromosome Translocation Near the INSR Locus", *Biochemical and Biophysical Communications*, vol. 159, No. 3, pp. 1275–1282 (Mar. 31, 1989).

Klapan, I. et al., "Prognostic significance of plasma prostaglandin E concentration in patients with head and neck cancer", *Journal of Cancer Research and Clnical Oncology*, vol. 118, No. 4, pp. 308–313 (1992).

Konger, R.L. et al., "Growth regulation of primary human keratinocytes by prostaglandin E receptor EP2 and EP3 subtypes", *Biochimica et Biophysica Acta*, vol. 1401, pp. 221–234 (1998).

Kubo, K. et al., "A Novel series of 4–phenoxyquinolines: potent and highly selective inhibitors of pdgf receptor autophosphorylation", *Bioorganic & Medicinal Chemistry Letters*, vol. 7, No. 23, pp. 2935–2940 (1997).

Kumar, A. et al., "Structural Organization and Chromosomal Mapping of JAK3 Locus", *Onogene*, vol. 13, No. 9, pp. 2009–2014 (Nov. 7, 1996).

Leonard, W.J., "STATs and Cytokine Specificity", *Nature Medicine*, vol. 2, No. 9, pp. 968–969 (Sep. 1996).

Levy, D.E., "The House that JAK/STAT Built", *Cytokine & Growth Factor Reviews*, vol. 8, No. 1, pp. 81–90 (Mar. 1997).

Ley, R.D. et al., "Rapid Communication Ultraviolet Radiation–Induced Malignant Melanoma in Monodelphis Domestica", *Photochemistry and Pholobiology*, vol. 50, No. 1, pp. 1–5 (1989).

Lynch, N.R. et al., "Mechanism of Inhibition of Tumour Growth by Aspirin and Indomethacin", *The British Journal of Cancer*, vol. 38, No. 4, pp. 503–512 (Oct. 1978).

Maftah, A. et al., "10–N Nonyl–Acridine Orange: A Fluorescent Probe which Stains Mitochondria Independently of their Energetic State", *Biochemical and Biophysical Communications*, vol. 164, No. 1, pp. 185–190 (Oct. 16, 1989).

Mahajan, S. et al., "Rational Design and synthesis of a Novel Anti–leukemic Agent Targeting Bruton's Tyrosine Kinase (BTK), LFM–A13 (alpha–Cyano–Beta–Hydroxy–Beta–Methyl–N– (2, 5–Dibromophenyl) Propenamide)", *The Jouranl of Biological chemistry*, vol. 274, No. 14, pp. 9587–9599 (Apr. 1, 1999).

Mahajan, S. et al., "Src Family Protein Tyrosine Kinases Induce Autoactivation of Bruton's Tyrosine Kinase", *Molecular and Cell Biology*, vol. 15, No. 10, pp. 5304–5311 (Oct. 1995).

Malaviya, R. et al., "Genetic and Biochemical evidence for acritical role of Janus Kinase (JAK)–3 in mast cell–mediated type I hypersensitivity reactions", *Biochemistry and Biophysical Research Communications*, vol. 257, No. 3, pp. 807–813 (1999).

Mancini, M. et al., "Mitochondrial Proliferation and Paradoxical Membrane Depolarization during Terminal Differentiation and Apoptosis in a Human Colon Carcinoma Cell Line", *The Journal of Cell Biology*, vol. 138, No. 2, pp. 449–469 (Jul. 28, 1997).

Marks, R., "An Overview of Skin Cancers—Incidence and Causation", *Supplement to Cancer*, vol. 75, No. 2, pp. 607–612 (Jan. 15, 1995).

Mellet, P. et al., "Stopped Flow Fluorescence Energy Transfer Measurement of the Rate Constants Describing the Reversible Formation and the Irreversible Rearrangement of the Elastase–Alpha1–Proteinase Inhibitor Complex", *The Journal of Biological Chemistry*, vol. 273, No. 9119–9123 (Apr. 10, 1998).

Messinger, Y. et al., "In Vivo Toxcity and Pharmacokinetic Features of B43 (Anti–CD19)–Genistein Immunoconjugate in Nonhuman Primates", *Clinical Cancer Research*, vol. 4, pp. 165–170 (Jan. 1998).

Mitchell, P.D. et al., "Transcriptional Regulation in Mammalian Cells by Sequence–Specific DNA Binding Proteins", *Science*, vol. 245, pp. 371–378 (Jul. 21, 1989).

Miyashita, A. et al., "An approach to the synthesis of apavaverine analogue containing a quinazoline ring system", *Heterocycles*, vol. 40, No. 2, pp. 653–660 (Mar. 1995).

Mohammadi, M. et al., "Structure of the FGF Receptor Tyrosine Kinase Domain Reveals a Novel Autoinhibitory Mechanism", *Cell*, vol. 86, pp. 577–587 (Aug. 23, 1996).

Mohammadi, M. et al., "Structures of the Tyrosine Kinase Domain of Fibroblast Growth Factor Receptor in Complex with Inhibitors", *Science*, vol. 276, pp. 955–960 (May 9, 1997).

Myers, D.E. et al., "Membrane–associated CD219–LYN complex is an endogenous p53–independent and Bc–12–independent regulator of apoptosis in human B–lineage lymphoma cells", *Proceedings of the National Academy of Sciences*, vol. 92, No. 21, pp. 9575–9579 (Oct. 10, 1995).

Myers, M.R. et al., "The preparation and sar of 4–(anilino), 4–(phenoxy), and 4–(thiophenoxy)–quinazolines: inhibitors of p56lck and EGF–R tyrosine kinase activity", *Bioorganic & Medicinal Chemistry Letters*, vol. 7, No. 4, pp. 417–420 (1997).

Nakamura, N. et al., "An epidermal Growth Factor Receptor/Jak2 Tyrosine Kinase Domain Chimera Induces Tyrosine phosphorylation of Stat5 and Transduces a Growth Signal in Hematopoietic Cells", *The Journal of Biological Chemistry*, vol. 271, No. 32, pp. 19483–19488 (Aug. 9, 1996).

Narla, R.K. et al., "4–(3'–Bromo–4' hydroxylphenyl)–amino–6, 7–dimethoxyquinazoline: A novel quinazoline derivative with potent cytotoxic activity against human glioblastoma cells", *Clinical Cancer Research*, vol. 4, No. 6, pp. 1405–1414 (Jun. 1998).

Newman, J.D. et al., "Enhanced Insulin–Receptor Tyrosine Kinase Activity Associated with Chromosomal Translocation (1; 19) in a Pre–B–Cell Leukemia Line", *International Journal of Cancer*, vol. 50, No. 3, pp. 500–504 (Feb. 1, 1992).

Nomoto, Y. et al., "Studies on Cardiotonic Agents. I. Synthesis of Some Quinazoline Derivatives", *Chemical & Pharmaceutical Bulletin*, vol. 38, No. 6, pp. 1591–1595 (Jun. 1990).

Nosaka, T. et al., "Defective Lymphoid Development in Mice Lacking Jak3", *Science*, vol. 270, pp. 800–802 (Nov. 3, 1995).

Petit, P.X. et al., "Alterations in Mitochondrial Structure and Function Are Early Events of Dexamethasone–Induced Thymocyte Apoptosis", *The Journal of Cell Biology*, vol. 130, No. 1, pp. 157–167 (Jul. 1995).

Plescia, O.J. et al., "Subversion of Immune System by Tumor Cells and Role of Prostaglandins", *Proceedings of the National Academy of Sciences*, vol. 72, No. 5, pp. 1848–1851 (May 1975).

Rewcastle, G.W. et al., "Tyrosine Kinase Inhibitors. 5. Synthesis and Structure–Activity Relationships for 4–(Phenylmethyl) amino) – and 4–(Phenylamino) quinazolines as Potent Adenosine 5'–Triphosphate Binding Site Inhibitors of the Tyrosine Kinase Domain of the Epidermal Growth", *Journal of Medicinal Chemistry*, vol. 38, No. 18, pp. 3482–3487 (1995).

Riedy M.C. et al., "Genomic Sequence, Organization, and Chromosomal Localization of Human JAK3", *Genomic*, vol. 37, No. 1, pp. 57–61 (Oct. 1, 1996).

Rolling, C. et al., "JAK3 associates with the human Interleukin 4 receptor and is tyrosine phosphorylated following receptor triggering", *Onogene*, vol. 10, No. 9, pp. 1757–1761 (May 5, 1995).

Rosette, C. et al., "Ultraviolet Light and Osmotic Stress: Activation of the JNK Cascade Through Multiple Growth Factor and Cytokine Receptors", *Science*, vol. 274, pp. 1194–1197 (Nov. 15, 1996).

Sack, J.S., "CHAIN—A Crystallographic Modeling Program", *Journal of Molecular Graphics*, vol. 6, No. 1, p. 224 (Mar. 1988).

Safford, M. et al., "JAK3: A Member of the Jak Family of Non–Receptor Tyrosine Kinases is Expressed in the stem/orgenitor cell fraction of human bone marrow", *Blood*, vol. 84, No. 10 Suppl. 1, Abstract No. 475, 122a.

Safford, M.G. et al., "JAK3: Expression and Mapping to Chromosome 19p13–13.1", *Experimental Hematology*, vol. 25, No. 5, pp. 374–386 (May 1997).

Sharfee, N. et al., "Jak3 Activation in Human Lymphocyte precursor Cells", *Clinical and Experimental Immunology*, vol. 108, No. 3, pp. 552–556 (Jun. 1997).

Sicheri, F. et al., "Crystal Structure of the Src Family Tyrosine Kinae Hck", *Nature*, vol. 385, No. 6617, pp. 603–609 (Feb. 13, 1997).

Smiley, S.T. et al., "Intracellular heterogeneity in mitochondrial membrane potentials revealed by a Jaggregate–forming lipophilic cation JC–1", *Proceedings of the National Academy of Sciences*, vol. 88, No. 9, pp. 3671–3675 (May 1991).

Smith, P.K. et al., "Measurement of Protein Using Bicinchoninic Acid", *Analytical Biochemistry*, vol. 150, pp. 76–85 (1985).

Snyder, D.S. et al., "Intradermal Anti–Prostaglandin Agents and Sunburn", *The Journal of Investigative Dermatology*, vol. 62, No. 1, pp. 47–50 (Jan. 1974).

Snyder, D.S. et al., "Topical indomethacin and sunburn", *British Journal of Dermatology*, vol. 90, No. 1, pp. 91–93 (Jan. 1974).

Snyderman, C.H. et al., "Inhibition of Growth of a Murine Squamous Cell Carinoma by a Cyclooxygenase Inhibitor Increases Leukotriene B4 Production", *Archives of Otolaryngology—Head & Neck Surgery*, vol. 121, pp. 1017–1020 (Sep. 1995).

Sudbeck, E.A. et al., "Structure–based Design of Specific Inhibitors of Janus Kinase 3 as Apoptosis–inducing Antileukemic Agents", *Clinical Cancer Research*, vol. 5, pp. 1569—1582 (Jun. 1999).

Thomis, D.C. et al., "Defects in B Lymphocyte Maturation and T Lymphocyte Activation in Mice Lacking Jak3", *Science*, vol. 270, pp. 794–797 (Nov. 3, 1995).

Tortolani, P.J. et al., "Regulation of JAK3 Expression and Activation in Human B Cells and B Cell Malignancies", *The Journal of Immunology*, vol. 155, No. 11, pp. 5220–5226 (Dec. 1, 1995).

Tuel, Ahlgren, L. et al., "Role of Tyrosine Phosphorylation in Radiation–Induced Cell Cycle–Arrest of Leukemia B–Cell Precursors at the G2–M Transition Checkpoint", *Leukemia and Lymphoma*, vol. 20, No. 5–6, pp. 417–426 (1996).

Uckun, F.M. et al., "Biotherapy of B–Cell Precursor Leukemia by Targeting Genistein to CD 19–Associated Tyrosine Kinases", *Science*, vol. 267, pp. 886–891 (Feb. 10, 1995).

Uckun, F.M. et al., "Cytotoxic Activity of Epidermal Growth Factor–Genistein against Breast Cancer Cells", *Clinical Cancer Research*, vol. 4, No. 4, pp. 901–902 (Apr. 1998).

Uckun, F.M. et al., "Physical and Funcational Interactions between Lyn and p34cdc2 Kinases in Irradiated Human B–cell Precursors", *The Journal of Biological Chemistry*, vol. 271, No. 11, pp. 6389–6397 (Mar. 15, 1996).

Uckun, F.M. et al., "Use of a Novel Colony Assay to Evaluate the Cytotoxicity of an Immunotoxin Containing Pokeweed Antiviral Protein Against Blast Progenitor Cells Freshly Obtained from Patients with Common B–Linkeage Acute Lymphoblastic Leukemia", *The Journal of Experimental Medicine*, vol. 163, pp. 347–368 (Feb. 1986).

Vanderveen, E.E. et al., "Arachidonic Acid Metabolites in Cutaneous Carcinomas", *Archives of Dermatology*, vol. 122, No. 4, pp. 407–412 (Apr. 1986).

Vassilev, A. et al., "Bruton's Tyrosine Kinase as an Inhibitor of the Fas/CD95 Death–inducing Signaling complex", *The Journal of Biological Chemistry*, vol. 274, No. 3, pp. 1646–1656 (Jan. 15, 1999).

Verheij, M. et al., "Requirement for Ceramide–Initiated SAPK/JNK Signaling in Stress–Induced Apoptosis", *Nature*, vol. 380, No. 6569, pp. 75–79 (Mar. 7, 1996).

Witthuhn, B.A. et al., "Differential Substrate Recognition Capabilities of Janus Family Protein Tyrosine Kinases Within the Interleukin 2 Receptor (112R) System: Jak3 as a Potential Molecular Target for Treatment of Leukemias with a Hyperactive Jak–Stat Signaling Machinery", *Leukemia and Lymphoma*, vol. 32, No. 3/4, pp. 289–297 (1999).

Woodward, D.F. et al., "Re–evaluation of the effect of non–steroidal anti–inflammatory agents on u.v.–induced cutaneous inflammation", *Agents and Actions*, vol. 11, No. 6/7, pp. 711–717 (Dec. 1981).

Xiao, J. et al., "Signal Transduction through the Betal Intergrin Family Surface Adhesion Molecules VLA–4 and VLA–5 of Human B–cell Precursors Activates CD19 Receptor–associated Protein–tyrosine Kinases", *The Journal of Biological Chemistry*, vol. 271, No. 13, pp. 7659–7664 (Mar. 29, 1996).

Zhu, D. et al., "Calphostin C Triggers Calcium–dependent Apoptosis in Human Acute Lymphoblastic Leukemia Cells", *Clinical Cancer Research*, vol. 4, No. 12, pp. 2967–2976 (Dec. 1998).

* cited by examiner

B

| Protein Tyrosine Kinase | Residue at Region A | Residue at Region B | Residue at Region C | Residue at Region D | Residue at Region E | Residue at Region F |
|---|---|---|---|---|---|---|
| JAK3 | Pro906 | Tyr904 | Leu905 | Met902 | Ala966 | Asp912 |
| JAK2 | Pro933 | Tyr931 | Leu932 | Met929 | Gly993 | Asp939 |
| JAK1 | Pro948 | Phe946 | Leu947 | Met944 | Gly1008 | Glu954 |
| BTK | Ala478 | Tyr476 | Met477 | Thr474 | Ser538 | Asn484 |
| SYK | Glu342 | Met340 | Ala341 | Met338 | Ser403 | Lys348 |
| HCK | Ala342 | Phe340 | Met341 | Ala342 | Ala403 | Asp348 |
| LYN | Ala323 | Tyr321 | Met322 | Ala323 | Ala384 | Asp329 |
| IRK | Ala1080 | Leu1078 | Met1079 | Met1076 | Gly1149 | Ser1086 |

FIG. 4B

FIG. 7D1
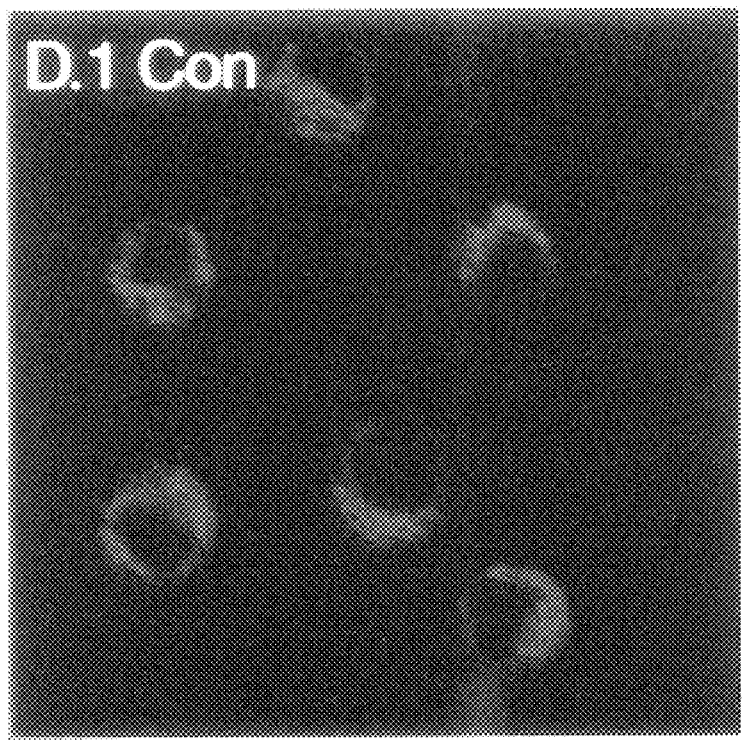
FIG. 7D2

FIG. 8B1
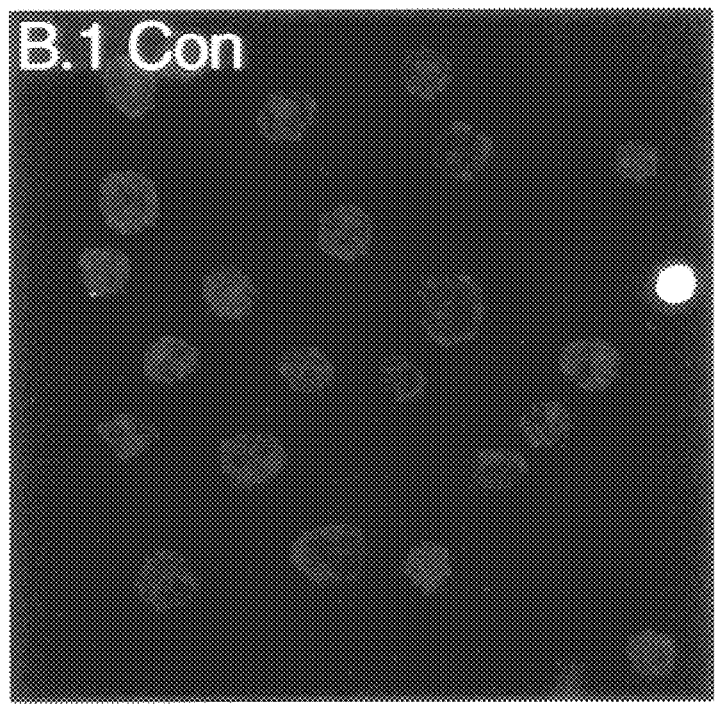
FIG. 8B2
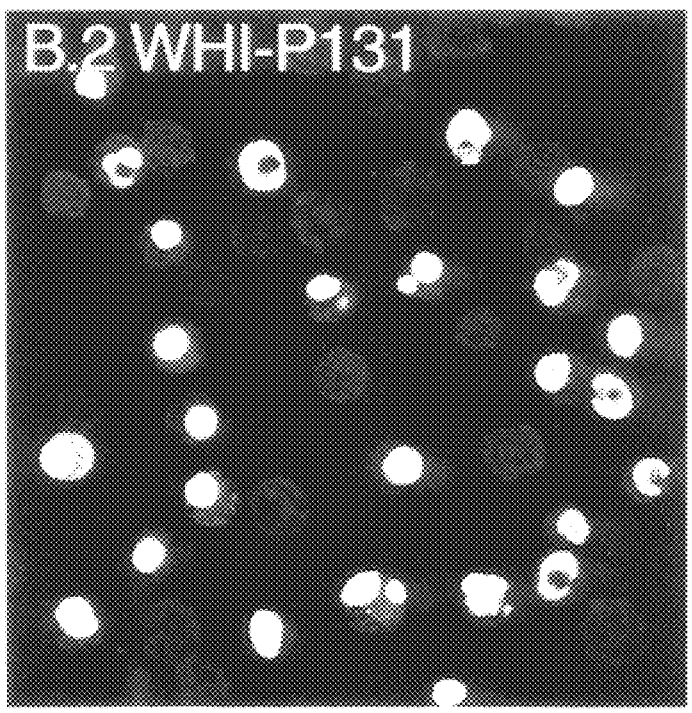

A. Control  B. UVB  C. DDE9501+UVB

WHI-P131 (60 mg/kg/day) - effects on GVHD development

| Group | n | Cumulative proportion surviving | | | | median survival (d) | Logrank p value vs. Control | Logrank p value vs. WHI-P13 |
|---|---|---|---|---|---|---|---|---|
| | | 30 | 60 | 90 | | | | |
| CONTROL | 51 | 90.2 ± 4.2 | 17.6 ± 5.3 | 2.0 ± 1.9 | | 44 | | |
| WHI-P131 | 9 | 100 ± 0 | 77.8 ± 13.9 | 33.3 ± 15.7 | | 82 | 0.0003 | |
| WHI-P132 | 9 | 88.9 ± 10.5 | 11.1 ± 10.5 | 0 ± 0 | | 44 | 0.485 | |
| Methotrexate | 16 | 93.8 ± 6.1 | 56.2 ± 12.4 | 25.0 ± 10.8 | | 63.5 | 0.0009 | 0.356 |
| Methotrexate + WHI-P131 | 13 | 100 ± 0 | 76.9 ± 11.7 | 61.5 ± 13.5 | | 87 | <0.0001 | 0.320 |
| Cyclosporine A | 15 | 73.3 ± 11.4 | 26.7 ± 11.4 | 13.3 ± 8.8 | | 45 | 0.493 | 0.029 |
| Cyclosporine A + WHI-P131 | 15 | 80.0 ± 10.3 | 33.3 ± 12.2 | 20.0 ± 10.3 | | 51 | 0.198 | 0.067 |

Methotrexate vs.
Methotrexate + WHI-P131
0.062

FIG. 26

DIMETHOXY QUINAZOLINES FOR TREATING DIABETES

PRIORITY OF INVENTION

This application is a continuation of application Ser. No. 09/378,093, filed Aug. 20, 1999, which claims the benefit of provisional application Ser. Nos. 60/097,365 and 60/097,359, filed Aug. 21, 1998, which application(s) are incorporated herein by reference.

BACKGROUND OF THE INVENTION

Signal Transducers and Activators of Transcription (STATs) are a family of DNA binding proteins that reside in the cytoplasm until they are activated by tyrosine phosphorylation. This phosphorylation event is catalyzed by members of the Janus family of tyrosine kinases, including JAK3 (Ihle, J. N. *Adv. Immunol.* 60: 1–35, 1995; Witthuhn, B. A., et al., *Leukemia and Lymphoma.* 32: 289–297, 1999).

The dual role of STATs as signaling molecules and transcription factors is reflected in their structure. All STAT proteins contain a DNA binding domain, an SH2 domain, and a transactivation domain necessary for transcriptional induction. In unstimulated cells, latent forms of STATs are predominantly localized in the cytoplasm. Ligand binding induces STAT proteins to bind with their SH2 domains to the tyrosine phosphorylated motifs in the intracellular domains of various transmembrane cell surface receptors (Horvath, C. M. and Darnell, J. E., *Curr. Opin. Cell. Biol.* 9(2): 233–239., 1997; Levy, D. E., *Cytokine Growth Factor Rev.* 8(1): 81–90, 1997).

Once STATs are bound to receptors, the receptor-associated Janus kinases (JAKs) phosphorylate STATs on a single tyrosine residue located near the SH2 domain. Two STATs then dimerize through specific reciprocal SH2-phosphotyrosine interactions. The dimerized STAT proteins can also form complexes with other DNA-binding proteins. The STAT dimers/complexes next translocate to the nucleus and utilize their DNA binding domain to interact with DNA response elements in promoters of target genes (Demoulin, J. B., et al., *Mol. Cell. Biol.* 16: 4710–6, 1996). STATs then interact directly or indirectly, via their transactivation domain, with components of the RNA polymerase II complex to activate transcription of target genes. Different ligands employ specific JAK and STAT family members, thus utilization of this pathway mandates specificity in signaling cascades and contributes to a diverse array of cellular responses. Janus kinases, including JAK3, are abundantly expressed in primary leukemic cells from children with acute lymphoblastic leukemia (ALL), the most common form of childhood cancer, and recent studies have correlated STAT activation in ALL cells with signals regulating apoptosis (Demoulin, J. B., et al., *Mol. Cell. Biol.* 16: 4710–6, 1996; Jurlander, J., et al., *Blood.* 89: 4146–4152, 1997; Kaneko, S., Suzuki, et al., *Clin. Exp. Immun.* 109: 185–193, 1997; and Nakamura, N., et al., *J. Biol. Chem.* 271: 19483–8, 1996).

Thus, JAK-3 is an important enzyme that plays an essential role in the function of lymphocytes, macrophages, and mast cells. Compounds which inhibit JAK-3 would be expected to be useful for treating or preventing diseases or conditions wherein the function of lymphocytes, macrophages, or mast cells is implicated, such as, leukemia, lymphoma, transplant rejection (e.g. pancreas islet transplant rejection, bone marrow transplant applications (e.g. graft-versus-host disease), autoimmune diseases (e.g. diabetes), and inflammation (e.g. asthma, inflammation associated with sun burn, and skin cancer). A continuing need exists for compounds and methods that are useful for the treatment and/or prevention of such conditions and diseases.

SUMMARY OF THE INVENTION

The present invention provides JAK-3 inhibiting compounds that are nontoxic in the administered dosage range. The JAK-3 inhibitors of the invention are useful for treating leukemia and lymphoma. The compounds are also useful to prevent skin cancer, as well as to treat or prevent sunburn and UVB-induced skin inflammation. In addition, the compounds of the present invention prevent the immunosuppressive effects of UVB radiation, and are useful to treat or prevent autoimmune diseases, inflammation, and transplant rejection.

The present invention provides a therapeutic method for treating leukemia or lymphoma comprising administering to the mammal in need thereof an effective amount of a JAK-3 inhibitor.

The present invention also provides a therapeutic method for preventing or reducing UV B radiation-induced inflammatory response in a mammal comprising administering to the mammal in need thereof an effective amount of a JAK-3 inhibitor.

The present invention also provides a therapeutic method for inhibiting the release of prostaglandin $E_2$ in a mammal comprising administering to the mammal in need thereof an effective amount of a JAK-3 inhibitor.

The present invention also provides a therapeutic method for preventing or reducing UVB-induced skin edema or vascular permeability changes in a mammal comprising administering to the mammal in need thereof an effective amount of a JAK-3 inhibitor.

The present invention also provides a therapeutic method for preventing or reducing UV B radiation-induced damage to epithelial cells or mutation frequency in skin in a mammal comprising administering to the mammal in need thereof an effective amount of a JAK-3 inhibitor.

The present invention also provides a therapeutic method for protecting a mammal from tumorigenic effects of UVB light comprising administering to the mammal in need thereof an effective amount of a JAK-3 inhibitor.

Representative JAK-3 inhibitors of the invention have also been found to exhibit significant anti-proliferative activity against T-cells, and have been found to inhibit IL-2 dependent cell proliferation. Thus, the compounds can be used to treat or prevent transplant complications (e.g. rejection of a donor organ transplant by the host immune system), and complications associated with bone marrow transplantation such as graft versus host disease.

In addition, the compounds of the invention are effective in treating and preventing autoimmune diseases, such as insulin dependent diabetes. The compounds are also effective in treating airway inflammation (asthma).

Accordingly, the invention also provides a therapeutic method for treating (or preventing) leukemia, transplant rejection, graft-verses host disease, inflammation, asthma, autoimmune diseases including diabetes, and inflammation related cancer development in the skin, comprising administering to the mammal in need thereof an effective amount of a compound of formula I.

The invention also provides novel compounds of formula I disclosed herein as well as pharmaceutical compositions comprising compounds of formula I.

A specific JAK-3 inhibitor useful in the medicaments and methods of the invention is a compound of formula I:

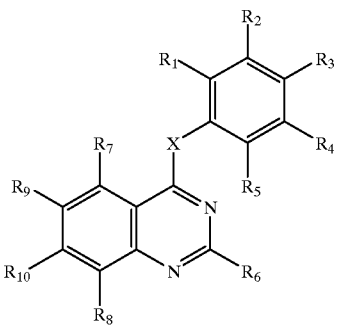

wherein:

X is HN, $R_{11}$N, S, O, $CH_2$, or $R_{11}$CH;

$R_{11}$ is hydrogen, ($C_1$–$C_4$)alkyl, or ($C_1$–$C_4$)alkanoyl;

$R_1$–$R_8$ are each independently hydrogen, hydroxy, mercapto, amino, nitro, ($C_1$–$C_4$)alkyl, ($C_1$–$C_4$)alkoxy, ($C_1$–$C_4$)alkylthio, or halo; wherein two adjacent groups of $R_1$–$R_5$ together with the phenyl ring to which they are attached may optionally form a fused ring, for example forming a naphthyl or a tetrahydronaphthyl ring; and further wherein the ring formed by the two adjacent groups of $R_1$–$R_5$ may optionally be substituted by 1, 2, 3, or 4 hydroxy, mercapto, amino, nitro, ($C_1$–$C_4$)alkyl, ($C_1$–$C_4$)alkoxy, ($C_1$–$C_4$)alkylthio, or halo; and $R_9$ and $R_{10}$ are each independently hydrogen, ($C_1$–$C_4$) alkyl, ($C_1$–$C_4$)alkoxy, halo, or ($C_1$–$C_4$)alkanoyl; or $R_9$ and $R_{10}$ together are methylenedioxy; or a pharmaceutically acceptable salt thereof. Peferably, at least one of $R_2$ and $R_3$ is hydroxy. More preferably, at least one of $R_2$ and $R_3$ is hydroxy, and one of $R_1$ to $R_5$ is halo.

BRIEF DESCRIPTION OF THE DRAWINGS

FIG. 26. shows the effects of compound 6 (60 mg/kg/day) on GVHD development.

DETAILED DESCRIPTION OF THE INVENTION

Figure 1:
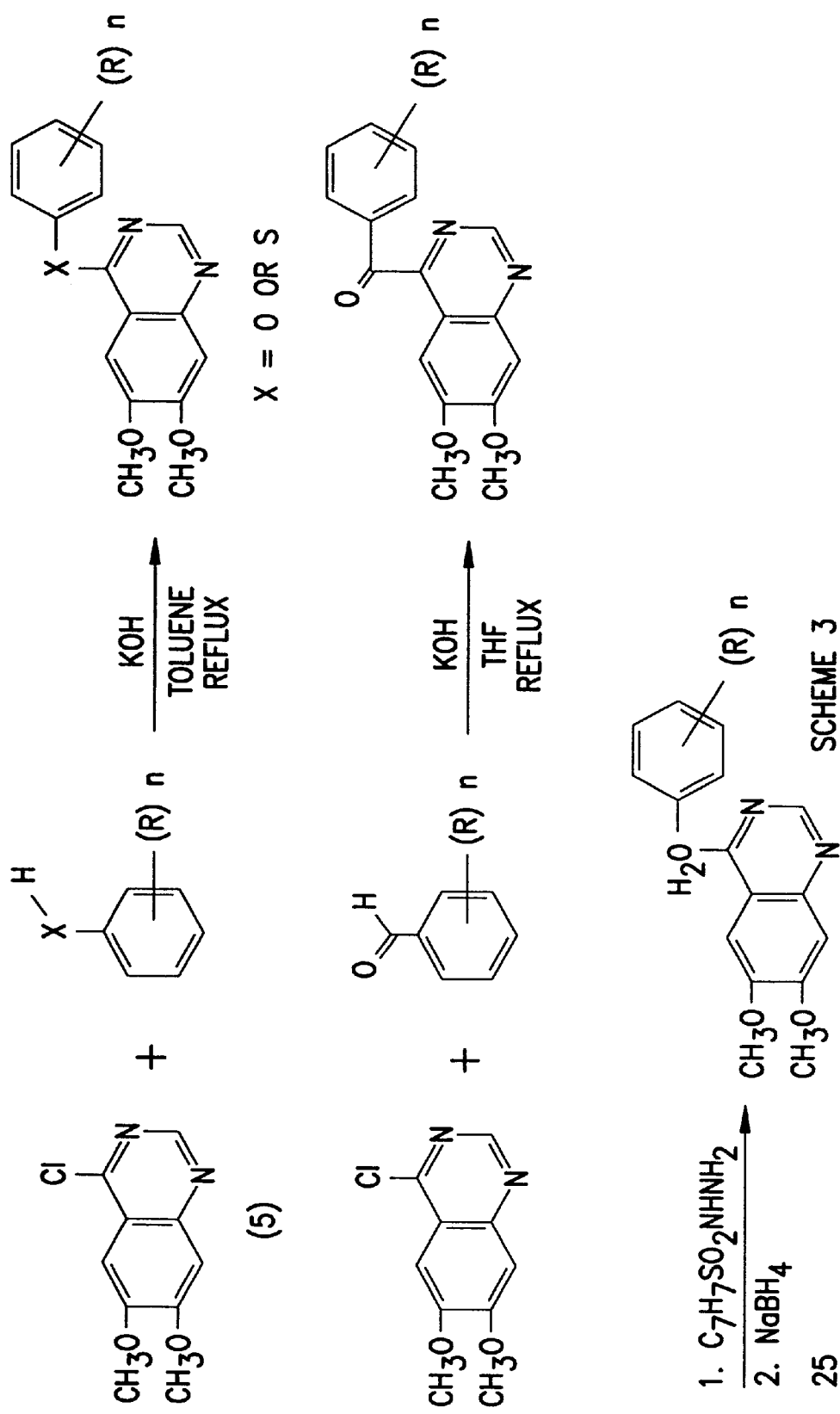
FIG. 1. Illustrates the synthesis of representative compounds of formula I from compound 5.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical and reference to an individual radical such as "isopropyl" embraces only the branched chain radical. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(W) wherein W is absent or is H, O, $(C_1-C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

Specific values listed below for radicals, substituents, and ranges, are for illustration only; they do not exclude other defined values or other values within defined ranges for the radicals and substituents Specifically, $(C_1-C_4)$alkyl can be methyl, ethyl, propyl, isopropyl, butyl, iso-butyl, or sec-butyl; $(C_1-C_4)$alkoxy can be methoxy, ethoxy, propoxy, isopropoxy, butoxy, iso-butoxy, or sec-butoxy; $(C_1-C_4)$alkylthio can be methylthio, ethylthio, propylthio, isopropylthio, butylthio, or isobutylthio; $(C_1-C_4)$alkanoyl can be acetyl, propanoyl, butanoyl, or isobutanoyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine prostaglandin $E_2$ inhibition activity using the standard tests described herein, or using other similar tests which are well known in the art.

A specific group of compounds are compounds of formula I wherein X is $R_{11}N$. Another specific group of compounds are compounds of formula I wherein X is HN.

A specific group of compounds are compounds of formula I wherein $R_1$, $R_2$, $R_4$, $R_5$, $R_6$, $R_7$, and $R_{10}$ are each H.

A specific group of compounds are compounds of formula I wherein $R_3$ is $(C_1-C_4)$alkoxy, hydroxy, nitro, halo, trifluoromethyl, or $NR_{12}R_{13}$ wherein $R_{12}$ and $R_{13}$ are each independently hydrogen, $(C_1-C_4)$alkyl, $(C_1-C_4)$alkenyl, $(C_1-C_4)$alkynyl, $(C_3-C_8)$cycloalkyl, or heterocycle. Another specific group of compounds are compounds of formula I wherein $R_3$ is hydroxy.

A specific group of compounds are compounds of formula I wherein $R_8$ is $(C_1-C_4)$alkoxy. Another specific group of compounds are compounds of formula I wherein $R_8$ is methoxy.

A specific group of compounds are compounds of formula I wherein $R_9$ is $(C_1-C_4)$alkoxy. Another specific group of compounds are compounds of formula I wherein $R_9$ is methoxy.

A preferred compound is 4-(4'-hydroxyl-phenyl)-amino-6,7-dimethoxyquinazoline WHI-P131; or a pharmaceutically acceptable salt thereof.

A preferred compound is 4-(3'-hydroxyl-phenyl)-amino-6,7-dimethoxyquinazoline WHI-P180; or a pharmaceutically acceptable salt thereof.

A preferred compound is 4-(3',5'-dibromo-4'-hydroxyl-phenyl)-amino-6,7-dimethoxyquinazoline WHI-P97; or a pharmaceutically acceptable salt thereof.

A preferred compound is 4-(3'-bromo-4'-hydroxyl-phenyl)-amino-6,7-dimethoxyquinazoline WHI-P154; or a pharmaceutically acceptable salt thereof.

The compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the Substances may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the Substance may be combined with one or more excipients and used in the form of ingestible tablets, buccal tablets, troches, capsules, elixirs, suspensions, syrups, wafers, and the like. Such compositions and preparations should contain at least 0.1% of the Substance. The percentage of the compositions and preparations may, of course, be varied and may conveniently be between about 2 to about 60% of the weight of a given unit dosage form. The amount of Substance in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the Substance may be incorporated into sustained-release preparations and devices.

The Substances may also be administered intravenously or intraperitoneally by infusion or injection. Solutions of the Substance can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the Substance which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the Substance in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the Substances may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the Substances can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the Substances to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the Substance in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the Substance required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The Substance is conveniently administered in unit dosage form; for example, containing 5 to 1000 mg, conveniently 10 to 750 mg, most conveniently, 50 to 500 mg of active ingredient per unit dosage form.

Ideally, the Substance should be administered to achieve peak plasma concentrations of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the Substance, optionally in saline, or orally administered as a bolus containing about 1–100 mg of the Substance. Desirable blood levels may be maintained by continuous infusion to provide about 0.01–5.0 mg/kg/hr or by intermittent infusions containing about 0.4–15 mg/kg of the Substance.

The Substance may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Melting points are uncorrected. $^1$H NMR spectra were recorded using a Varian Mercury 300 spectrometer in DMSO-$d_6$ or CDCl$_3$. Chemical shifts are reported in parts per million (ppm) with tetramethylsilane (TMS) as an internal standard at zero ppm. Coupling constant (J) are given in hertz and the abbreviations s, d, t, q, and m refer to singlet, doublet, triplet, quartet and multiplet, respectively. Infrared spectra were recorded on a Nicolet PROTEGE 460-IR spectrometer. Mass spectroscopy data were recorded on a FINNIGAN MAT 95, VG 7070E-HF G.C. system with an HP 5973 Mass Selection Detector. UV spectra were recorded on BECKMAN DU 7400 and using MeOH as the solvent. TLC was performed on a precoated silica gel plate (Silica Gel KGF; Whitman Inc). Silica gel (200–400 mesh, Whitman Inc.) was used for all column chromatography separations. All chemicals were reagent grade and were purchased from Aldrich Chemical Company (Milwaukee, Wis.) or Sigma Chemical Company (St. Louis, Mo.).

The synthesis of a representative compound of formula I is described in Example 1. Other compounds of formula I can be prepared using procedures similar to those described in Example 1.

Example 1

Chemical Synthesis and Characterization of 4-(4'-hydroxyl-phenyl)-amino -6,7-dimethoxyquinazoline (6)

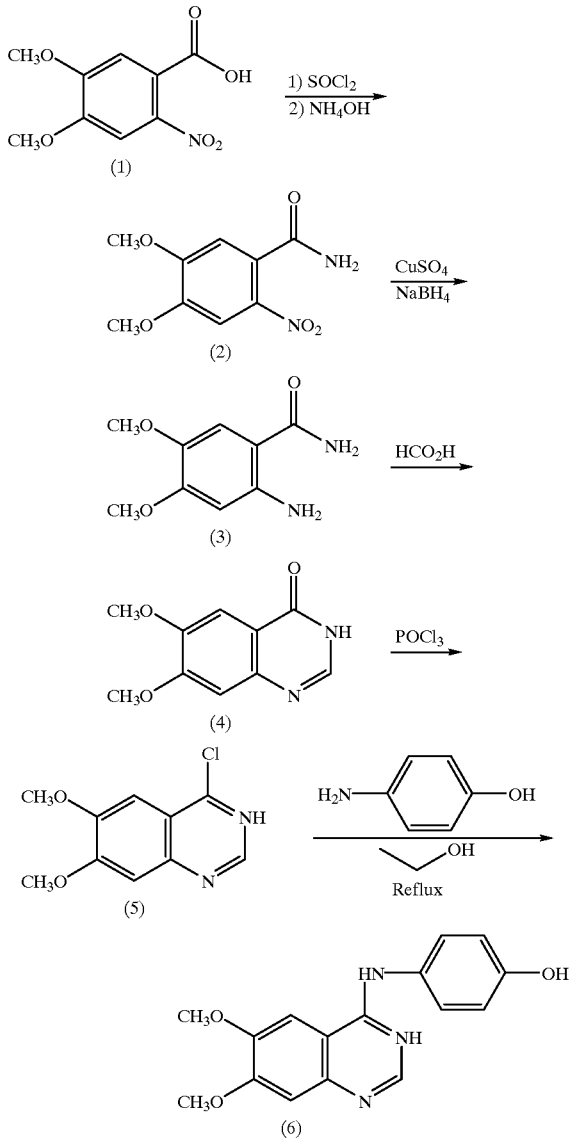

4,5-Dimethoxy-2-nitrobenzoic acid (1) was treated with thionyl chloride and then reacted with ammonia to give 4,5-dimethoxy-2-nitrobenzamide (2) as described by F. Nomoto et al. *Chem. Pharm. Bull.* 1990, 38, 1591–1595. The nitro group in compound (2) was reduced with sodium borohydride in the presence of copper sulfate (see C. L. Thomas *Catalytic Processes and Proven Catalysts* Academic Press, New York (1970)) to give 4,5-dimethoxy-2-aminobenzamide (3) which was cyclized by refluxing with formic acid to give 6,7-dimethoxyquinazoline-4(3H)-one (4). Compound (4) was refluxed with phosphorus oxytrichloride to provide compound (5), which is a useful intermediate for preparing compounds of formula I wherein X is NH. Reaction of compound (5) with the requsite aniline provided the following compounds of formula I:

| Compound | $R_1$ | $R_2$ | $R_3$ | $R_4$ | m.p. °C. |
|---|---|---|---|---|---|
| WHI-P97 | H | Br | OH | Br | >300 |
| WHI-P111 | H | Br | Me | H | 225–228 |
| WHI-P131 | H | H | OH | H | 245–248 |
| WHI-P132 | OH | H | H | H | 255–258 |
| WHI-P154 | H | Br | OH | H | 233–233.5 |
| WHI-P180 | H | OH | H | H | 256–258 |
| WHI-P197 | H | Cl | OH | H | 245 (dec) |
| WHI-P292 | OH | H | * | * | 277–279 |

*R3 and R4 together are benzo

Using a procedure similar to that described above, or using procedures which are known in the art for preparing other quinazoline compounds, compounds of formula I can be prepared. For example, Compounds of formula I wherein X is S, O, or $CH_2$ can be prepared from a compound of formula (5) by reaction with a requsite compound of the formula PhXH as illustrated in FIG. 1.

Example 2

Identification of Selective JAK-3 Inhibitors

Constructing A Homology Model for the JAK3 Kinase Domain. A homology model for JAK-3 was constructed as described by E. A. Sudbeck, et al., *Clinical Cancer Research*, 1999, 5, 1569–1582. Because the three dimensional coordinates of the JAK3 kinase domain are currently unknown, a structural model of JAK3 was required for a docking analysis of JAK3 inhibitors. A homology model of JAK3 was constructed (FIG. 2) by using known coordinates of homologous kinase domains as a reference. The JAK3 homology model was built by first obtaining the protein sequence of JAK3 (Swiss-Prot #P52333, Univ. of Geneva, Geneva, Switzerland) from GenBank (National Center for Biotechnology Information, Bethesda, Md.) and determining the most reasonable sequence alignment for the JAK3 kinase domain relative to some template coordinates (known kinase structures such as HCK, FGFR, and IRK (Sicheri, F., et al., Nature. 385: 602–9, 1997; Mohammadi, M., et al., Cell. 86: 577–587, 1996; Mohammadi, M., et al., Science. 276: 955–960, 1997; and Hubbard, S. R., et al., Nature, 372: 746–754, 1994). This was accomplished by first superimposing the Cα coordinates of the kinase domains of HCK, FGFR, and IRK using the InsightII program to provide the best overall structural comparison (InsightII, Molecular Simulations Inc. . San Diego, Calif., 1996). The sequences were then aligned based on the superimposition of their structures (amino acid sequences were aligned together if their Cα positions were spatially related to each other). The alignment accommodated such features as loops in a protein which differed from the other protein sequences. The structural superimposition was performed using the Homology module of the InsightII program and a Silicon Graphics INDIGO2 computer (Silicon Graphics, Mountain View, Calif.). The sequence alignment was done manually and produced a sequence variation profile for each superimposed Cα position. The sequence variation profile served as a basis for the subsequent sequence alignment of the JAK3 kinase with the other three proteins. In this procedure, the sequence of JAK3 was incorporated into the program and aligned with the three known kinase proteins based on the sequence variation profiles described previously. Next, a set of 3D coordinates was assigned to the JAK3 kinase sequence using the 3D coordinates of HCK as a template and the Homology module within the InsightII program. The coordinates for a loop region where a sequence insertion occurs (relative to HCK without the loop) were chosen from a limited number of possibilities automatically generated by the computer program and manually adjusted to a more ideal geometry using the program CHAIN (Sack, J. S., J. Mol. Graphics. 6: 244–245, 1988). Finally, the constructed model of the JAK3 kinase domain was subjected to energy minimization using the X-PLOR program so that any steric strain introduced during the model-building process could be relieved (Br ünger, A. T. X-PLOR, A System for X-ray Crystallography and NMR). The model was screened for unfavorable steric contacts and if necessary such side chains were remodeled either by using a rotamer library database or by manually rotating the respective side chains. The procedure for homology model construction was repeated for JAK1 (SWISS-PROT #P23458) and JAK2 (Genbank #AF005216) using the JAK3 model as a structural template. The energy minimized homology models of JAK1, JAK2, and JAK3 were then used, in conjunction with energy-minimized structural models of dimethoxyquinazoline compounds, for modeling studies of JAK/dimethoxyquinazoline complexes.

Docking Procedure Using Homology Model of JAK3 Kinase Domain. Modeling of the JAK3/dimethoxyquinazoline complexes was accomplished using the Docking module within the program INSIGHTII and using the Affinity suite of programs for automatically docking an inhibitor into a protein binding site (a similar procedure for EGFR and BTK was previously described, see Ghosh, S., et al., Clin. Can. Res. 4: 2657–2668, 1998; Mahajan, S., et al., J. Biol. Chem. 274: 9587–9599, 1999. The various docked positions of each compound were evaluated using a Ludi (Bohm, H. J. et al., J. Comput. Aided Mol. Des. 8: 243–256, 1994) scoring procedure in INSIGHTII which estimated a binding constant, $K_i$, taking into account the predicted lipophilic, hydrogen bonding, and van der Waals interactions between the inhibitor and the protein. A comparison of the catalytic site residues of several different PTK was made by manually superimposing crystal structure coordinates of the kinase domains of IRK and HCK, and models of JAK1, JAK2, JAK3, BTK, and SYK and then identifying features in the active site which were unique to JAK3 (FIG. 3 and FIG. 4).

Chemical synthesis of quinazoline derivatives. The compounds listed in Table 1 were synthesized and characterized using literature procedures (Rewcastle, G. W., et al., J. Med. Chem. 38: 3482–7, 1995).

Table 1. Predicted interaction of protonated quinazolines with JAK3 kinase active site and measured inhibition values ($IC_{50}$ values) from JAK3 kinase assays.

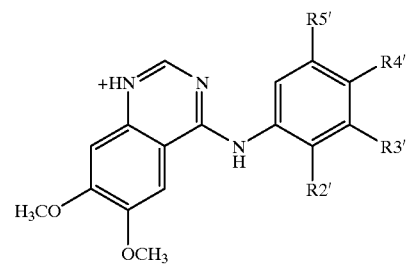

| Cmpd Name | R5' | R4' | R3' | R2' | # H Bonds | H Bond Score | Lipo Score | Contact Score | Total Binding Score | Est. $K_i$ (μM) | Mol. Surf. Area (Å$^2$) | Mol. Vol. (Å$^3$) | $IC_{50}$ (μM) |
|---|---|---|---|---|---|---|---|---|---|---|---|---|---|
| WHI-P131 | H | OH | H | H | 3 | 188 | 476 | 64 | 568 | 2.3 | 276 | 261 | 9.1 |
| WHI-P97 | Br | OH | Br | H | 3 | 156 | 559 | 65 | 622 | 0.6 | 314 | 307 | 11.0 |
| WHI-P154 | H | OH | Br | H | 3 | 171 | 512 | 64 | 587 | 1.4 | 296 | 284 | 27.9 |
| WHI-P79 | H | H | Br | H | 1 | 9 | 531 | 63 | 444 | 36 | 278 | 272 | >300 |
| WHI-P132 | H | H | H | OH | 1 | 82 | 476 | 66 | 462 | 25 | 269 | 264 | >300 |
| WHI-P111 | H | CH$_3$ | Br | H | 1 | 52 | 502 | 58 | 458 | 46 | 309 | 291 | >300 |
| WHI-P112 | Br | H | H | Br | 0 | 0 | 541 | 62 | 445 | 52 | 306 | 297 | >300 |
| WHI-P258 | H | H | H | H | 0 | 0 | 510 | 64 | 414 | 72 | 266 | 252 | >300 |

Immune Complex Kinase Assays. Sf21 (IPLB-SF21-AE) cells (Vassilev, A., et al., J. Biol. Chem. 274: 1646–1656, 1999) derived from the ovarian tissue of the fall armyworm *Spodotera frugiperda,* were obtained from Invitrogen (Carlsbad, Calif.) and maintained at 26–28° C. in Grace's insect cell medium supplemented with 10% FBS and 1.0% antibiotic/antimycotic (GIBCO-BRL). Stock cells were maintained in suspension at 0.2–1.6×10$^6$/ml in 600 ml total culture volume in 1 L Bellco spinner flasks at 60–90 rpm.

Cell viability was maintained at 95–100% as determined by trypan blue dye exclusion. Sf21 cells were infected with a baculovirus expression vector for BTK, SYK, JAK1, JAK2, or JAK3. Cells were harvested, lysed (10 MM Tris pH7.6, 100 nM NaCl, 1% Nonidet P-40, 10% glycerol, 50 mM NaF, 100 $\mu$M $Na_3VO_4$, 50 $\mu$g/ml phenylmethylsulfonyl fluoride, 10 $\mu$g/ml aprotonin, 10 $\mu$g/ml leupeptin), the kinases were immunoprecipitated from the lysates, and their enzymatic activity assayed, as reported (Vassilev, A., et al., J. Biol. Chem. 274: 1646–1656, 1999; Uckun, F. M., et al., Science. 22: 1096–1100, 1996; Goodman, P. A., et al., J. Biol. Chem. 273: 17742–17748, 1998; Mahajan, S., et al., Mol. Cell. Biol. 15: 5304–5311, 1995; and Uckun, F. M., et al., Science. 267: 886–891, 1995). The immunoprecipitates were subjected to Western blot analysis as previously described (Vassilev, A., et al., J. Biol. Chem. 274: 1646–1656, 1999; and Uckun, F. M., et al., Science. 22: 1096–1100, 1996).

For insulin receptor kinase (IRK) assays, HepG2 human hepatoma cells grown to approximately 80% confluency were washed once with serum-free DMEM and starved for 3 hours at 37° in a $CO_2$ incubator. Subsequently, cells were stimulated with insulin (Eli Lilly and Co., Indianapolis, Ind., cat# CP-410; 10 units/ml/10×$10^6$ cells) for 10 minutes at room temperature. Following this IRK activation step, cells were washed once with serum free medium, lysed in NP-40 buffer and IRK was immunoprecipitated from the lysates with an anti-IR$\beta$ antibody (Santa Cruz Biotechnology, Santa Cruz, Calif., Cat.# sc-711, polyclonal IgG). Prior to performing the immune complex kinase assays, the beads were equilibrated with the kinase buffer (30 mM Hepes pH 7.4, 30 mM NaCl, 8 mM $MgCl_2$, 4 mM $MnCl_2$). LYN was immunoprecipitated from whole cell lysates of NALM-6 human leukemia cells as previously reported (Uckun, F. M., et al., Science. 267: 886–891, 1995; and Uckun, F. M., et al., Journal of Biological Chemistry,. 271: 6396–6397, 1996).

In JAK3 immune complex kinase assays (17,22), KL-2 EBV-transformed human lymphoblastoid B cells (native JAK3 kinase assays) or insect ovary cells (recombinant JAK3 kinase assays) were lysed with NP-40 lysis buffer (50 mM Tris, pH 8, 150 mM NaCl, 5 mM EDTA, 1% NP-40, 100 $\mu$M sodium orthovanadate, 100 $\mu$M sodium molybdate, 8 $\mu$g/ml aprotinin, 5 $\mu$g/ml leupeptin, and 500 $\mu$M PMSF) and centrifuged 10 min at 13000×g to remove insoluble material. Samples were immunoprecipitated with antisera prepared against JAK3. The antisera were diluted and immune complexes collected by incubation with 15 $\mu$l protein A Sepharose. After 4 washes with NP-40 lysis buffer, the protein A Sepharose beads were washed once in kinase buffer (20 mM MOPS, pH7, 10 mM $MgCl_2$) and resuspended in the same buffer. Reactions were initiated by the addition of 25 $\mu$Ci [$\gamma$-$^{32}$P] ATP (5000 Ci/mMole) and unlabeled ATP to a final concentration of 5 $\mu$M. Reactions were terminated by boiling for 4 min in SDS sample buffer. Samples were run on 9.5% SDS polyacrylamide gels and labeled proteins were detected by autoradiography. Following electrophoresis, kinase gels were dried onto Whatman 3M filter paper and subjected to phosphorimaging on a Molecular Imager (Bio-Rad, Hercules, Calif.) as well as autoradiography on film. For each drug concentration, a kinase activity index (KA) was determined by comparing the kinase activity in phosphorimager units (PIU) to that of the baseline sample. In some experiments, cold kinase assays were performed, as described by (Uckun, F. M., et al., Clin. Can. Res. 4: 901–912, 1998).

Electrophoretic Mobility Shift Assays (EMSAs). EMSAs were performed to examine the effects of dimethoxyquinazoline compounds on cytokine-induced STAT activation in 32Dc11/IL2R$\beta$ cells (gift from Dr. James Ihle, St. Jude Children's Research Hospital), as previously described (Goodman, P. A., et al., J. Biol. Chem. 273: 17742–17748, 1998).

Mitochondrial Membrane Potential Assessment. To measure the changes in mitochondria, cells were incubated with WHI-P131 at concentrations ranging from 7.4 $\mu$g/ml (25 $\mu$M) to 30 $\mu$g/ml (200 $\mu$M) for 24 h or 48 h, stained with specific fluorescent dyes and analyzed with flow cytometer. Mitochondrial membrane potential ($\Delta\psi$m) was measured using two dyes including a lipophillic cation 5,5',6,6'-tetrachloro-1,1',3,3'-tetraethlybenzimidazolylcarbocyanine iodide (JC-1) and a cyanine dye, 1,1',3,3,3',3'-hexamethylindodicarbocyanine iodide (DiIC1 (27–29)) obtained from Molecular Probes (Eugene, Oreg.). JC-1 is a monomer at 527 nm after being excited at 490 nm; with polarization of $\Delta\psi$m, J-aggregates are formed that shift emission to 590 nm (30). This can be detected on a flow cytometer by assessing the green signal (at 527 nm) and green-orange signal (at 590 nm) simultaneously, creating an index of the number of cells polarized and depolarized mitochondria. DiIC1, a cyanine dye which is amphioatheic and cationic, concentrates in energized mitochondria and has been used in a variety of studies to measure the mitochondrial membrane potential (Fujii, H., et al., Histochem J. 29: 571–581, 1997; Mancini, M., et al., J. Cell Biol. 138. 449–469, 1997; and Petit, P. X., et al., J. Cell Biol. 130: 157–167, 1995). Cells were also stained with DiIC1 at 40 nM concentration for 30 min in the dark as described for JC-1. The cells were analyzed using a Vantage Becton Dickinson (San Jose, Calif.) cell sorter equipped with HeNe laser with excitation at 635 nm and the fluorescence was collected at 666 nm.

Mitochondrial Mass Determination. Relative mitochondrial mass was measured by using Becton Dickinson Calibur flow cytometry and the fluorescent stain 10-n-nonyl-acridine orange (NAO), which binds the mitochondrial phospholipid cardiolipin, that has been extensively used to provide an index of mitochondrial mass (Maftah, A., et al., Biochem. Biophys. Res. Commun. 164: 185–190, 1989).

Results and discussion for Example 2.

Figure 2A:
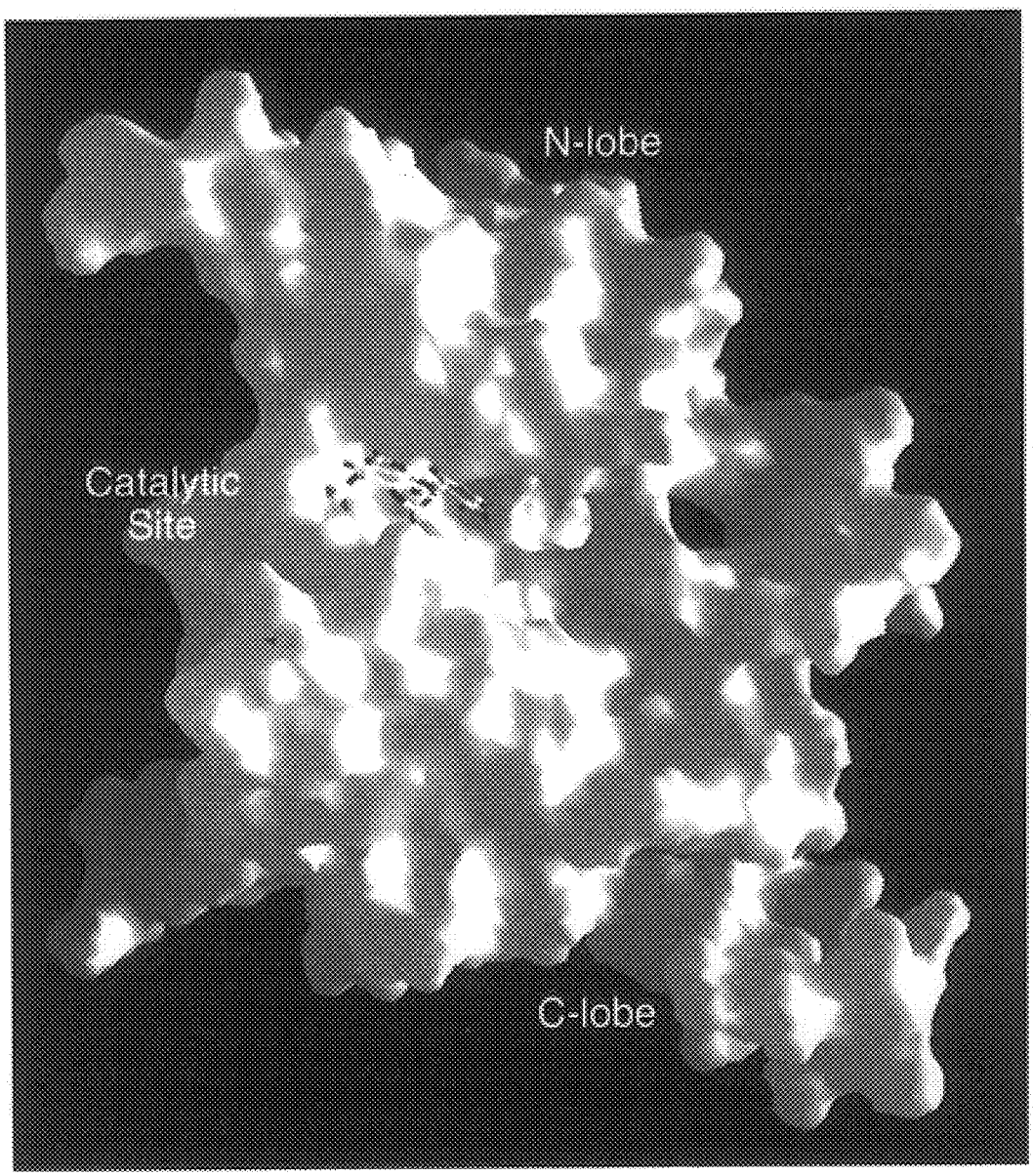
FIG. 2. [A] Model of JAK3 showing molecular surface of protein (blue), and catalytic (ATP binding) site (yellow). [B] Ribbon representation (Cα backbone) of the homology model of the JAK3 kinase domain. The WHI-P131 molecule is shown as a space-filling model in the catalytic site of JAK3. [C] Close-up view of catalytic site of JAK3 model with docked quinazoline inhibitor WHI-P131 (green). Residues and inhibitor are shown as space-filling atoms. The solvent-exposed opening of the catalytic site has dimensions to allow a relatively planar inhibitor to enter and bind to JAK3. The opening of the pocket is defined by residues Pro906, Ser907, Gly908, Asp912, Arg953, Gly829, Leu828, and Tyr904 (blue residues). The far wall deep inside the pocket is lined with Leu905 (Cα backbone), Glu903, Met902, Lys905, and Asp967 (pink residues), and the floor of the pocket is lined by Leu905 (side chain), Val884, Leu956, and Ala966 (yellow residues). Residues defining the roof of the pocket include Leu828, Gly829, Lys830, and Gly831 (uppermost blue residues). Prepared using InsightII program.
Figure 2B:
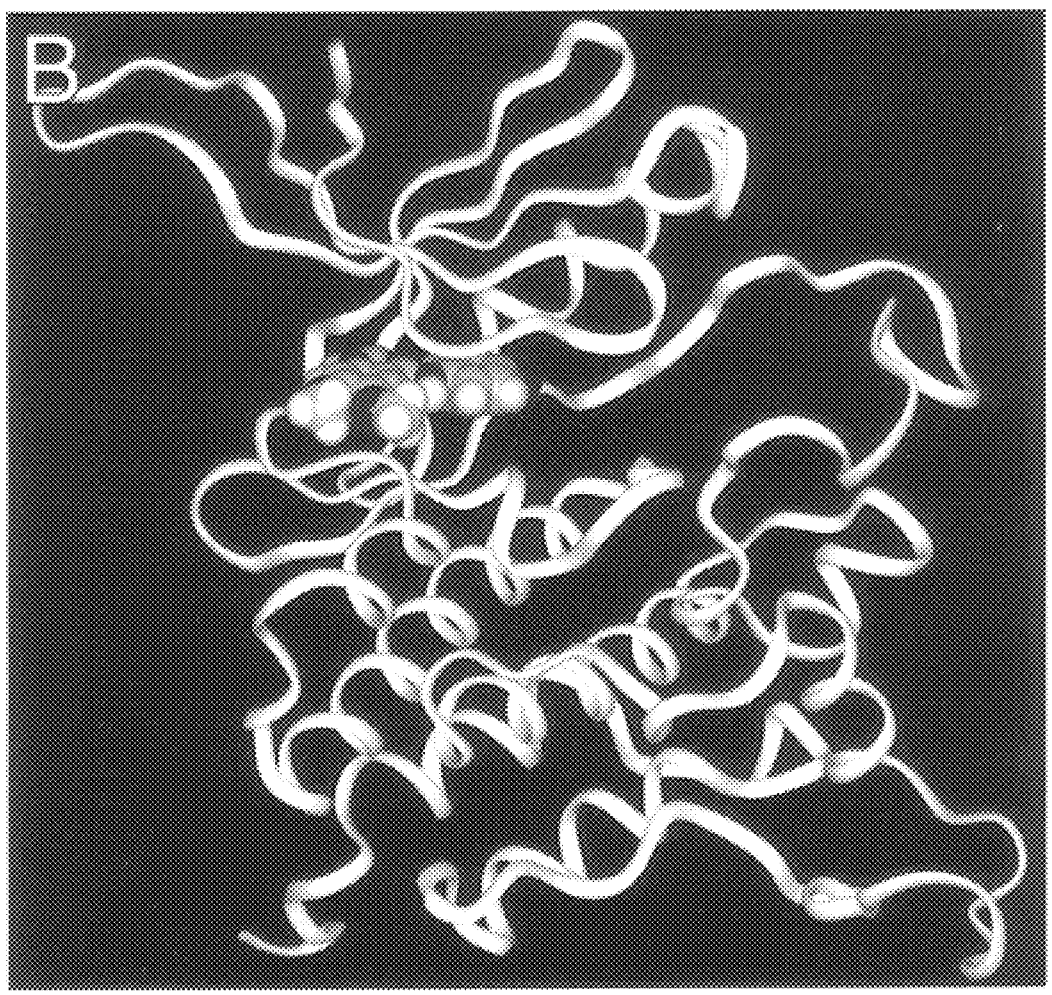
Figure 2C:
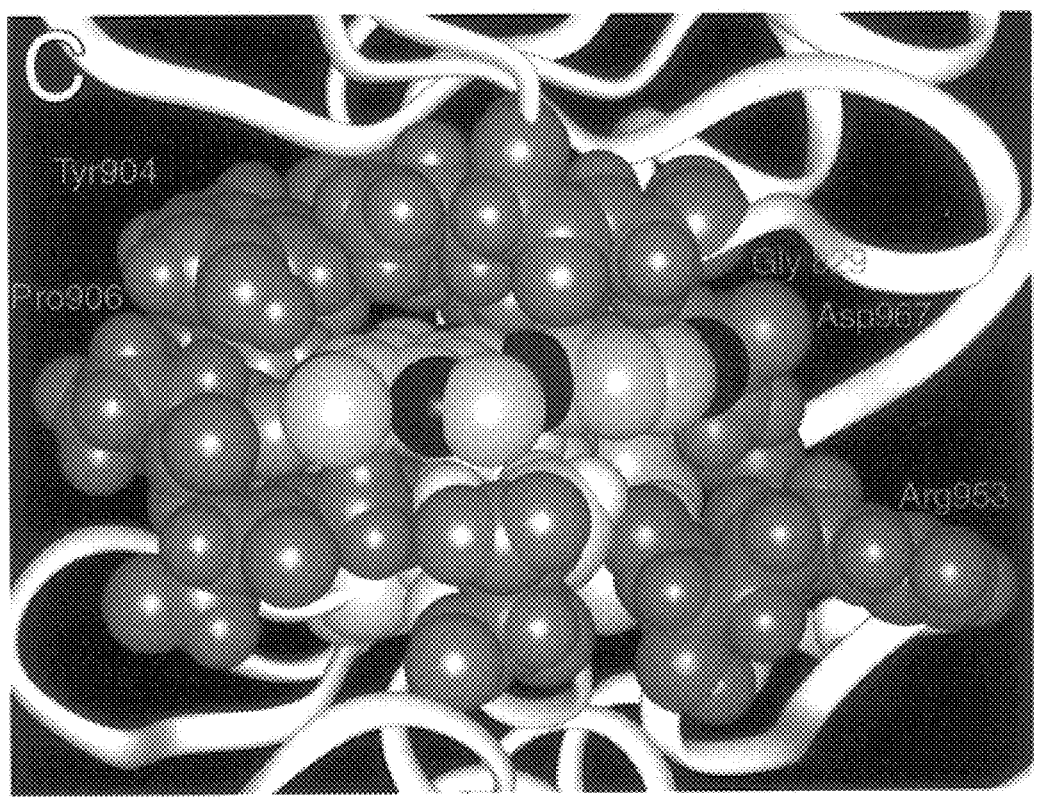
Figure 3A:
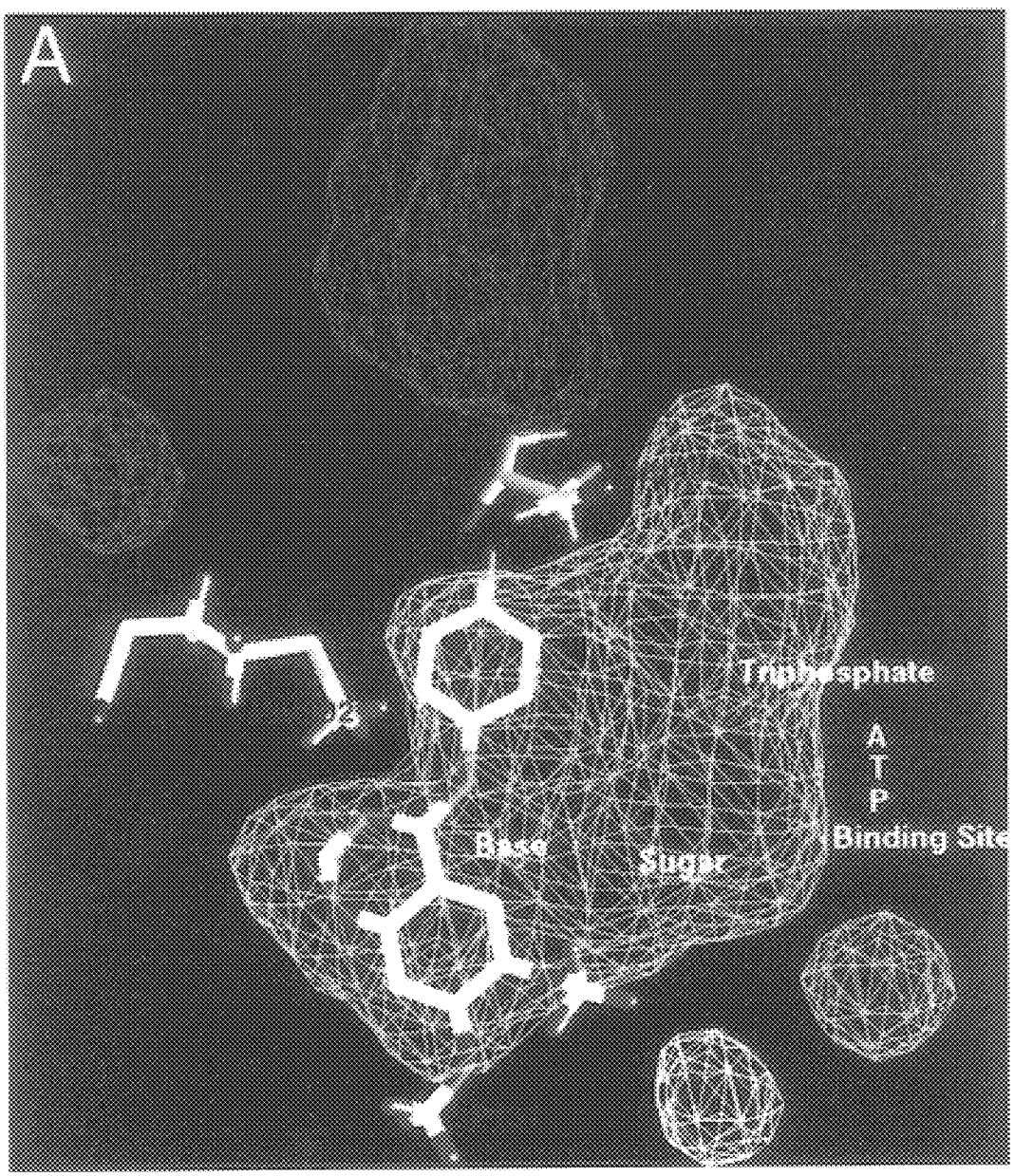
FIG. 3. [A] Model of unoccupied space in the catalytic (ATP binding) site of a JAK3 homology model. Shown in green is the binding site for ATP and the most likely binding site for dimethoxyquinazoline inhibitors. The green kinase active site region represents a total volume of approximately 530 Å. Modeling studies showed that an inhibitor or a portion of an inhibitor with significant binding to this region would occupy a volume less than 530 Å$^3$ and have molecular dimensions compatible with the shape of the binding site region. Other regions near the binding site which show measurable unoccupied volume are shown in royal blue, pink, yellow, and light blue. These binding regions are either unavailable to inhibitor molecules (royal blue) or represent regions just large enough to occupy solvent molecules (pink, yellow, light blue). A model of WHI-P131 docked into the catalytic site is shown in white, superimposed on the green region. [B] Model of the catalytic site of JAK3 with quinazolines WHI-P131 (multicolor), WHI-P132 (pink), and WHI-P154 (yellow). Each compound fits into the binding site but WHI-P132 (shown to be inactive against JAK3 in biological assays) lacks an OH group that is in a location to bind with Asp967. WHI-P131 and WHI-P154, with OH groups at the C4' position of the phenyl ring, are able to form a favorable interaction with Asp967 of JAK3, which may contribute to their enhanced inhibition activity. [C] Features of dimethoxyquinazoline derivatives which are predicted to aid binding to JAK3 catalytic site.

Homology Model of JAK3 Kinase Domain. The three-dimensional coordinates of JAK3 used in the protein/inhibitor modeling studies were constructed based on a structural alignment with the sequences of known crystal structures of the kinase domains of three protein tyrosine kinases (PTKs) (kinase domains of HCK (9), FGFR (11), and IRK (37)), as detailed in Materials and Methods. FIGS. 2A and 1B show the homology model of the JAK3 kinase domain, which is composed of an N-terminal lobe and a C-terminal lobe which are linked by a hinge region near the catalytic (ATP-binding) site. The catalytic site is a pocket located in the central region of the kinase domain, which is defined by two $\beta$-sheets at the interface between the N and C lobes. The opening to the catalytic site is solvent accessible and facilitates binding of ATP. Small molecule inhibitors can also bind to the catalytic site which results in an attenuation of PTK activity by inhibiting ATP binding. An analysis of the JAK3 model revealed specific features of the catalytic site which can be described as a quadrilateral-shaped pocket (FIG. 2C). The opening of the pocket is defined by residues Pro906, Ser907, Gly908, Asp912, Arg953, Gly829, Leu828, and Tyr904 (blue residues, FIG. 2C). The far wall deep inside the pocket is lined with Leu905 (C$\alpha$ backbone), Glu903, Met902, Lys905, and Asp967 (pink residues, FIG. 2C), and the floor of the pocket is lined by Leu905 (side chain), Val884, Leu956, and Ala966 (yellow residues, FIG. 2C). Residues defining the roof of the pocket include Leu828, Gly829, Lys830, and Gly831 (uppermost blue residues, FIG. 2C). FIGS. 2C and 3A illustrate that the catalytic site of the JAK3 model has approximate dimensions of 8×11×20 Å and an available volume for binding of approximately 530 Å$^3$. According to the model, the solvent exposed opening to the binding region would allow inhibitors to enter and bind if the molecule contains some planarity.

Figure 4A:
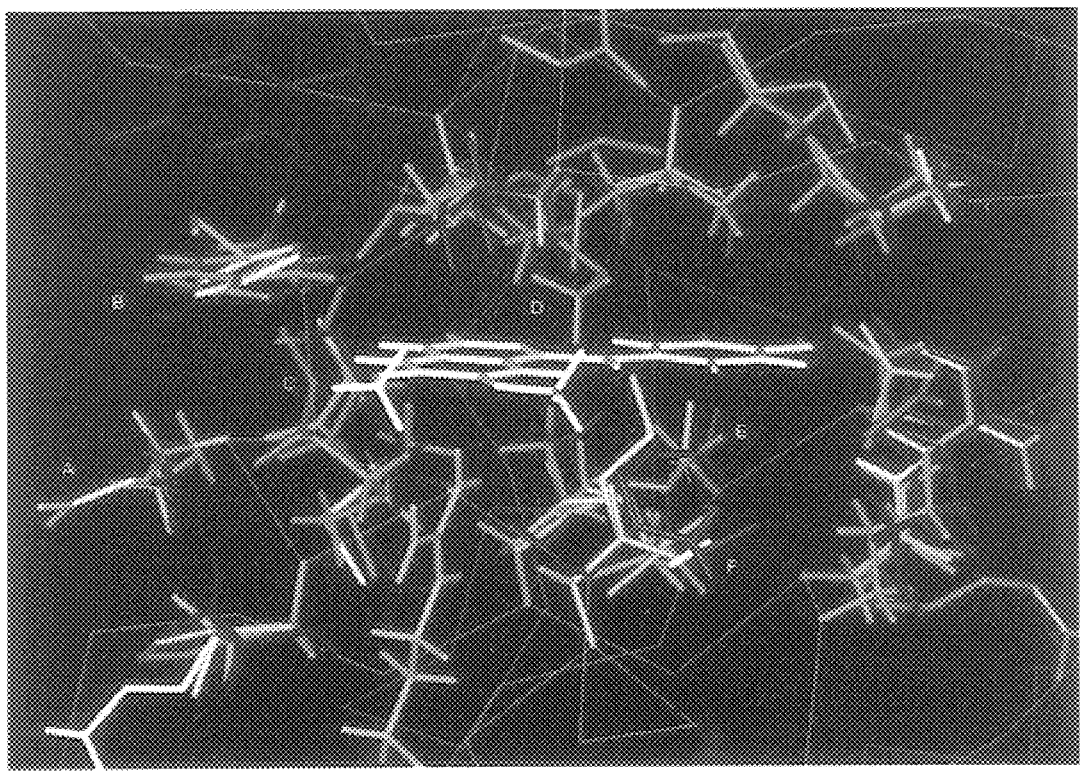
FIG. 4. [A] Structural comparison of nonconserved residues in the catalytic sites of 5 different protein tyrosine kinases: JAK3 (pink), BTK (red), SYK (light blue), IRK (dark blue), and HCK (yellow). Residues within 5 Å of the docked JAK3 inhibitor, WHI-P131 (white), are shown as rod-shaped side chains. The C alpha backbone of JAK3 is shown as a thin pink line, for perspective. Regions A to F correspond to areas containing nonconserved residues in the catalytic site (see B and Results and Discussion). Crystal structure coordinates of HCK and IRK, and homology models of JAK3, BTK, and SYK were used for the structural analysis. [B] Nonconserved residues in the catalytic sites of 8 different protein tyrosine kinases. Regions A–F refer to locations in the catalytic site which are illustrated in A.

While most of the catalytic site residues of the JAK3 kinase domain were conserved relative to other PTKs, a few specific variations were observed FIG. 4). These differences include an alanine residue in BTK, IRK, and HCK/LYN (region A, FIG. 4A) which changes to Glu in SYK and Pro906 in JAK3. At region B, a tyrosine residue is conserved in JAK3 (Tyr904), BTK, and LYN, but changes to Phe in HCK (which is the only apparent residue difference between HCK and LYN relevant to inhibitor binding), Met in SYK, and Leu in IRK. Region C shows a methionine residue which is conserved in BTK, IRK, and HCK/LYN, but changes to Leu905 in JAK3 and to Ala in SYK. Region D shows Met902 in JAK3, which is conserved in SYK and IRK but changes to Thr in BTK and to a much smaller residue, Ala, in LYN and HCK. This Met902 residue in JAK3, which is located on the back wall of the pocket and protrudes in toward the center of the pocket volume, can significantly affect the shape of the binding pocket. At this location, the extended conformation of the Met902 side chain can hinder the close contact of inhibitors with residues lining the back wall of the pocket and with the hinge region, relative to other kinases with smaller residues here such as BTK (Thr) and HCK/LYN (Ala). Ala966 in region E is conserved in HCK/LYN but changes to Gly in IRK and to the more hydrophilic residue Ser in BTK and SYK. Region F, which is farther away from the inhibitor location, is the least conserved region of the catalytic site and contains Asp912 in JAK3, Asn in BTK, Lys in SYK, Ser in IRK, and Asp in HCK/LYN (FIG. 4). These residue identity differences between tyrosine kinases provide the basis for designing selective inhibitors of the JAK3 kinase domain.

Figure 3B:
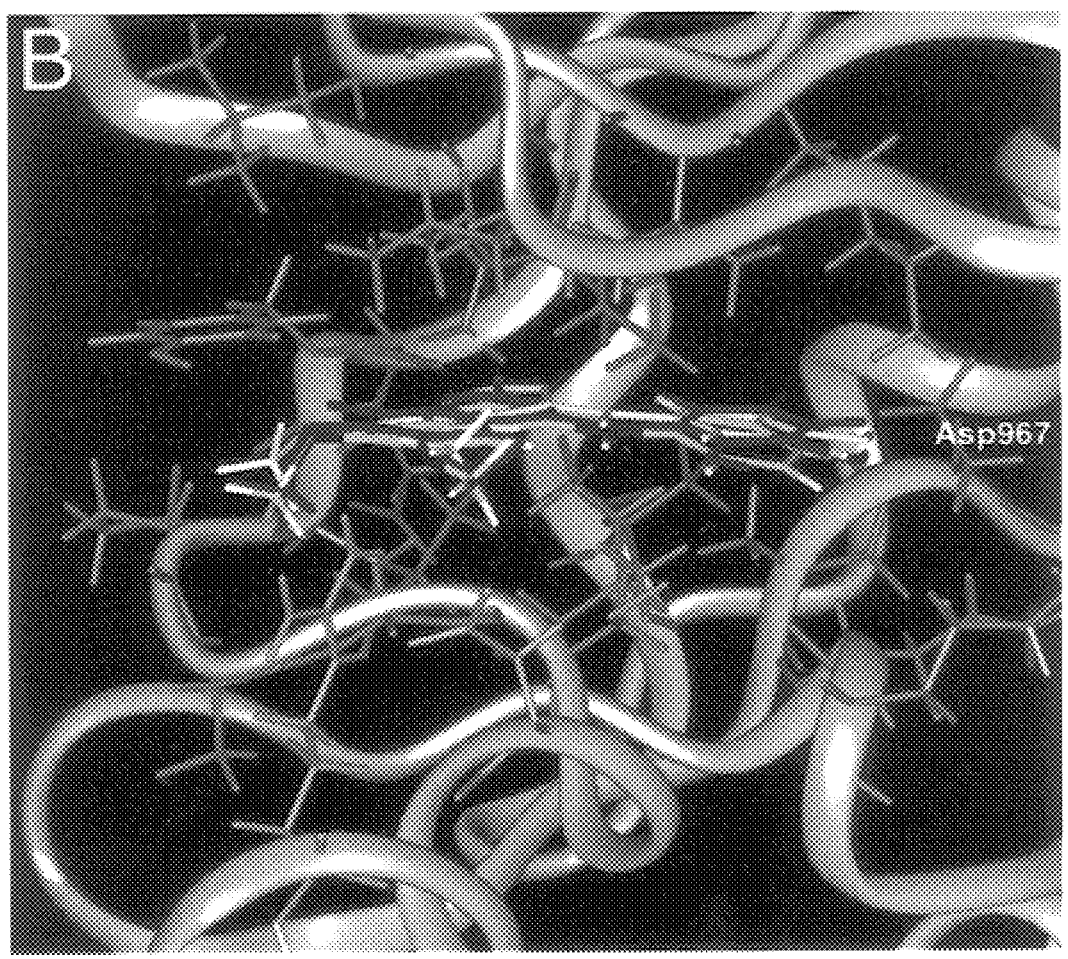

Structure-based Design and Synthesis of JAK3 Inhibitors. A computer docking procedure was used to predict how well potential inhibitors could fit into and bind to the catalytic site of JAK3 and result in kinase inhibition (FIG. 3B). The dimethoxyquinazoline compound WHI-P258 (4-(phenyl)-amino-6,7-dimethoxyquinazoline) contains two methoxy groups on the quinazoline moiety but no other ring substituents. Molecular modeling studies using the homology model of JAK3 kinase domain suggested that WHI-P258 would fit into the catalytic site of JAK3, but probably would not bind very tightly due to limited hydrogen bonding interactions. Asp967, a key residue in the catalytic site of JAK3, can form a hydrogen bond with molecules binding to the catalytic site, if such molecules contain a hydrogen bond donor group such as an OH group. WHI-P258, however, does not contain an OH group and therefore would not interact as favorably with Asp967. We postulated that the presence of an OH group at the 4' position of the phenyl ring of WHI-P258 would result in stronger binding to JAK3 because of added interactions with Asp967. A series of dimethoxyquinazoline compounds were designed and synthesized to test this hypothesis.

An estimation of the molecular volume for the compounds is provided in Table 1.

Figure 3C:
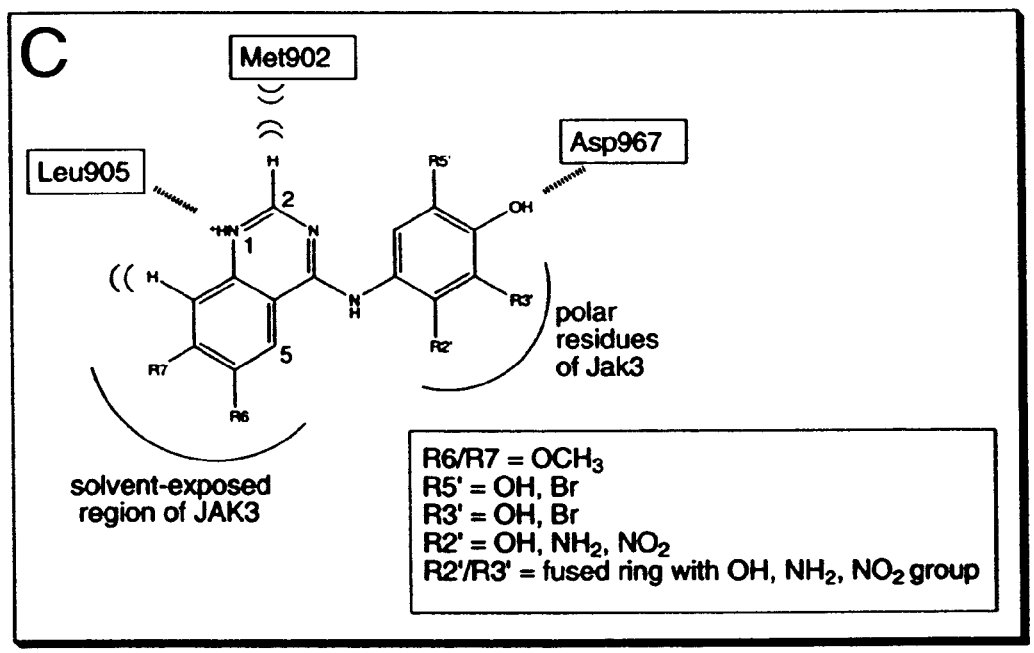

A summary of structural features of the designed dimethoxyquinazoline compounds which were observed to be relevant for binding to the catalytic site of JAK3 is shown in FIG. 3C. The approximate molecular volumes of the compounds in Table 1 range from 252 Å to 307 Å, which are small enough to fit into the 530 Å$^3$ binding site of JAK3 kinase. Table 1 also lists the results of molecular modeling studies including estimated binding constants (i.e., $K_i$ values) for the compounds which were docked into the JAK3 catalytic site. The compounds which were evaluated in docking studies contain substitutions of similar functional groups at different positions on the phenyl ring.

The conformations of the energy-minimized docked models of the compounds listed in Table 1 were relatively planar, with dihedral angles of approximately 4–18° between the phenyl ring and quinazoline ring system. This conformation allows the molecule to fit more easily into the catalytic site of JAK3. All of the listed compounds contain a ring nitrogen (N1), which can form a hydrogen bond with NH of Leu905 in the hinge region of JAK3. When N1 is protonated, the NH can instead interact with the carbonyl group in Leu905 of JAK3. The presence of an OH group at the 4' position on the phenyl ring was anticipated to be particularly important for binding to the catalytic site of JAK3. WHI-P131 (estimated $K_i$=2.3 μM), WHI-P154 (estimated $K_i$=1.4 μM), and WHI-P97 (estimated $K_i$=0.6 μM) shown in Table 1 were predicted to have favorable binding to JAK3 and potent JAK3 inhibitory activity because they contain a 4' OH group on the phenyl ring which can form a hydrogen bond with Asp967 of JAK3, contributing to enhanced binding. However, the 2' OH group of WHI-P132 is not in the right orientation to interact with Asp967 and it probably would form an intramolecular hydrogen bond with the quinazoline ring nitrogen, which may contribute to a significantly lower affinity of WHI-P132 for the catalytic site of JAK3. The relatively large bromine substituents (WHI-P97, WHI-P154) can increase the molecular surface area in contact with binding site residues if the molecule can fit into the binding site. Modeling of WHI-P154 and WHI-P97 showed that there is enough room to accommodate the bromine groups if the phenyl ring is tilted slightly relative to the fused ring group of the molecule. The results from the modeling studies prompted the hypothesis that WHI-P131, WHI-P154, and WHI-P97 would exhibit potent JAK3-inhibitory activity. In order to test this hypothesis and validate the predictive value of the described JAK3 homology model, we synthesized WHI-P131, WHI-P154, WHI-P97, and 5 other dimethoxyquinazoline compounds listed in Table 1.

Figure 5A:
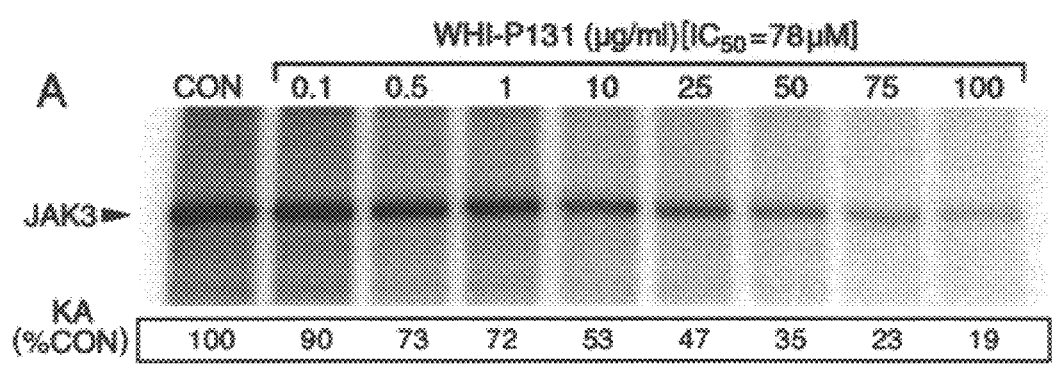
FIG. 5. Effects of WHI-P131 on the Tyrosine Kinase Activity of JAK3. [A]–[D]. JAK3, JAK1, and JAK2 immunoprecipitated from Sf21 insect ovary cells transfected with the appropriate baculovirus expression vectors were treated with WHI-P131, then subjected to in vitro kinase assays as described in Methods. The enzymatic activity of JAKs was determined by measuring autophosphorylation in a 10 min kinase assay, as described in Methods. The kinase activity (KA) levels were expressed as percentage of baseline activity (% CON). [E] EMSAs of 32Dc22-IL-2Rβ cells. WHI-P131 (10 μg/ml=33.6 μM) and WHI-P154 (10 μg/ml=26.6 μM) (but not WHI-P132; 10 μg/ml=33.6 μM) inhibited IL-2 triggered JAK-3-dependent STAT activation but not IL-3-triggered JAK-1/JAK-2-dependent STAT activation in 32Dc11-IL-2Rβ cells.
Figure 5B:
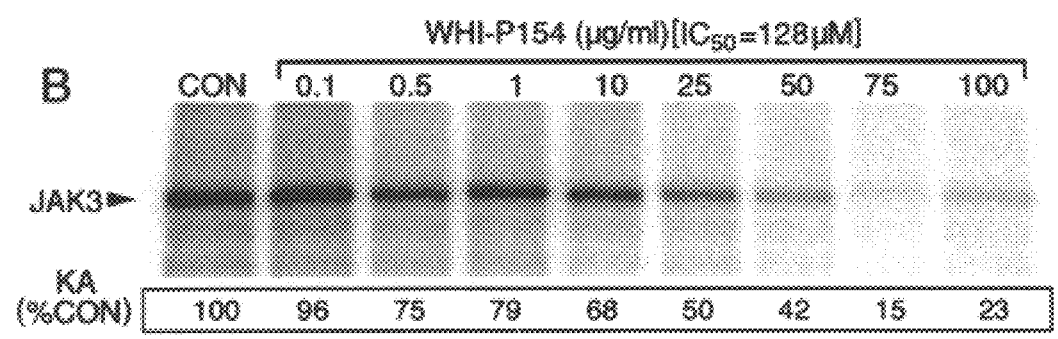

Inhibition of JAK3 by Rationally Designed Dimethoxyquinazoline Compounds. We first used immune complex kinase assays to compare the effects of the synthesized dimethoxyquinazoline compounds on the enzymatic activity of human JAK3 immunoprecipitated from the KL2 EBV-transformed human lymphoblastoid B cell line. WHI-P131, WHI-P154, and WHI-P97, which had very similar estimated $K_i$ values ranging from 0.6 μM to 2.3 μM and were predicted to show significant JAK3 inhibitory activity at micromolar concentrations (which was not the case for the other compounds which had estimated $K_i$ values ranging from 25 μM to 72 μM), inhibited JAK3 in concentration-dependent fashion. The measured IC$_{50}$ values were 9.1 μM for WHI-P131, 11.0 μM for WHI-P97, and 27.9 μM for WHI-P154, but >300 μM for all the other dimethoxyquinazoline compounds (Table 1). WHI-P131 and WHI-P154 were also tested against recombinant murine JAK3 expressed in a baculovirus vector expression system and inhibited JAK3 in a concentration-dependent fashion with an IC$_{50}$ value of 23.2 μg/ml (~78 μM, FIG. 5A) and 48.1 μg/ml (~128 μM, FIG. 5B), respectively. The ability of WHI-P131 and WHI-P154 to inhibit recombinant JAK3 was confirmed in 4 independent experiments. These kinase assay results are consistent with our modeling studies described above.

Figure 5C:
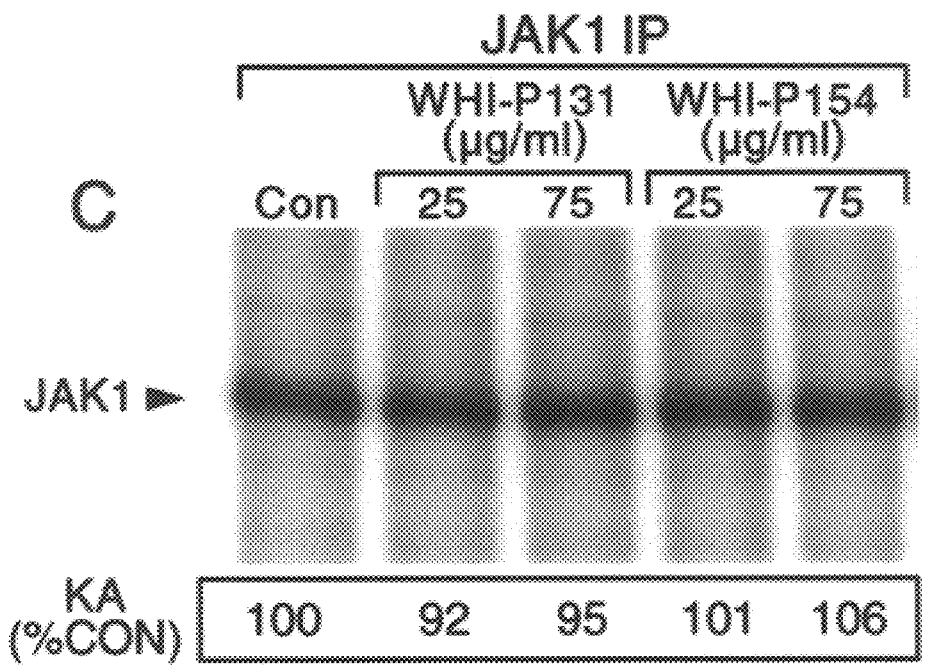
Figure 5D:
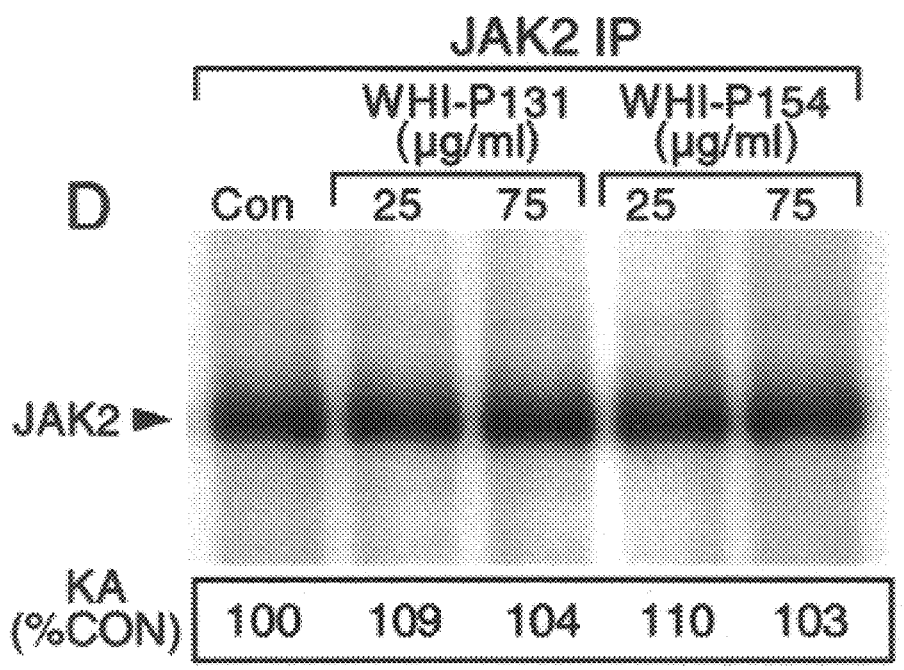
Figure 5E:
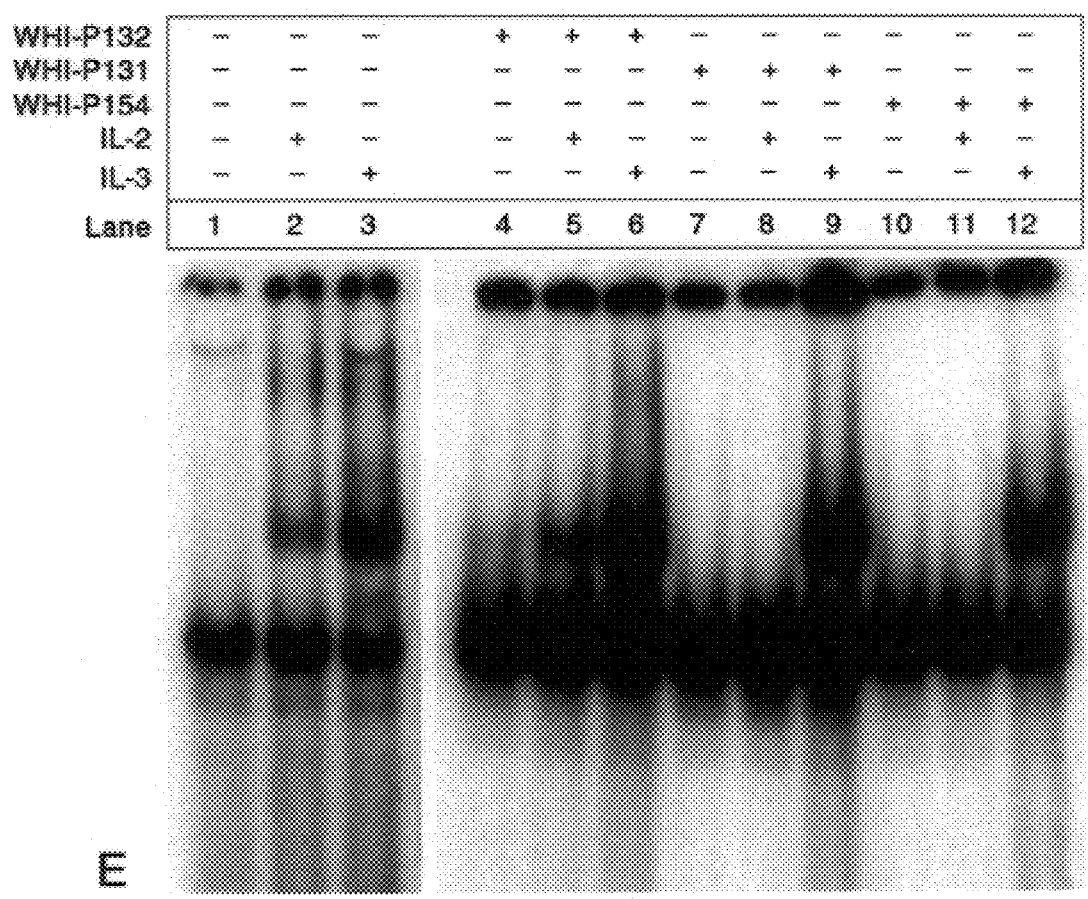

Importantly, WHI-P131 and WHI-P154 did not exhibit any detectable inhibitory activity against recombinant JAK1 or JAK2 in immune complex kinase assays (FIGS. 5C and 5D). Electrophoretic Mobility Shift Assays (EMSAs) were also performed to confirm the JAK3 specificity of these dimethoxyquinazoline compounds by examining their effects on cytokine-induced STAT activation in 32Dc11/IL2Rβ cells. As shown in FIG. 5E, both WHI-P131 (10 μg/ml=33.6 μM) and WHI-P154 (10 μg/ml=26.6 μM) (but not the control compound WHI-P132, 10 μg/ml=33.6 μM) inhibited JAK3-dependent STAT activation after stimulation with IL-2, but they did not affect JAK1/JAK2-dependent STAT activation after stimulation with IL-3. Modeling studies suggest that this exquisite JAK3 specificity could in part be due to an alanine residue (Ala966) which is present in the catalytic site of JAK3 but changes to glycine in JAK1 and JAK2. This alanine group which is positioned near the phenyl ring of the bound dimethoxyquinazoline compounds can provide greater hydrophobic contact with the phenyl group and thus can contribute to higher affinity relative to the smaller glycine residue in this region of the binding site in JAK1 and JAK2. However, an accurate interpretation of these remarkable differences in sensitivity of JAK3 versus JAK1 and JAK2 to WHI-131 and WHI-P154 will need to await the determination of the X-ray crystal structures of these kinases since simple amino acid discrepancies in their catalytic sites could result in pronounced structural differences.

Figure 6A:
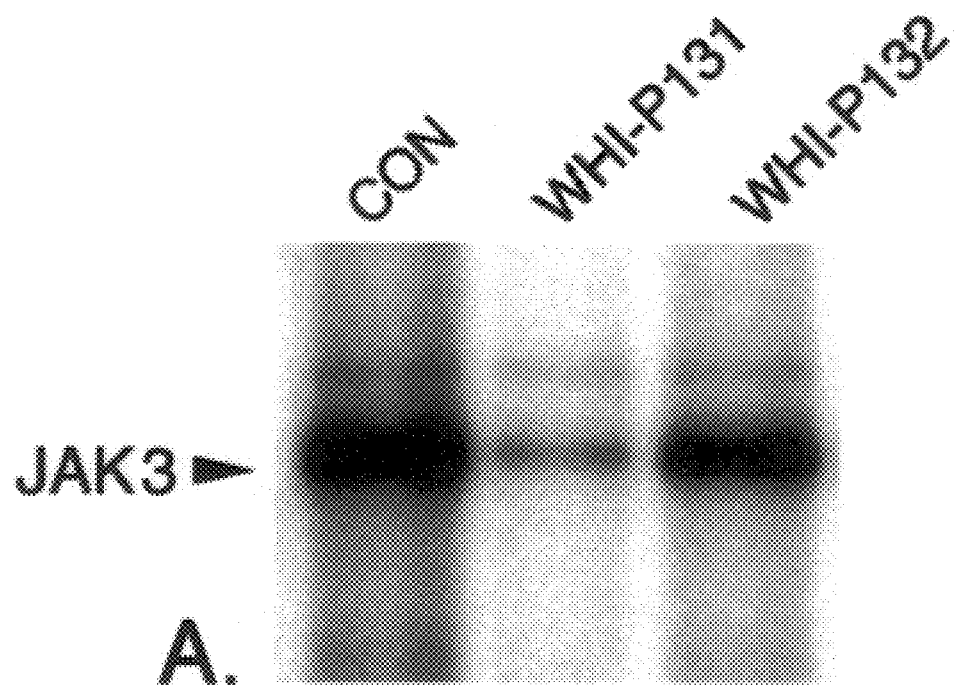
FIG. 6. Specificity of WHI-P131. JAK3, SYK, and BTK immunoprecipitated from Sf21 insect ovary cells transfected with the appropriate baculovirus expression vectors, LYN immunoprecipitated from NALM-6 human B-lineage ALL cells, and IRK immunoprecipitated from HepG2 hepatoma cells were treated with WHI-P131, then subjected to in vitro kinase assays as described in Methods.
Figure 6B:
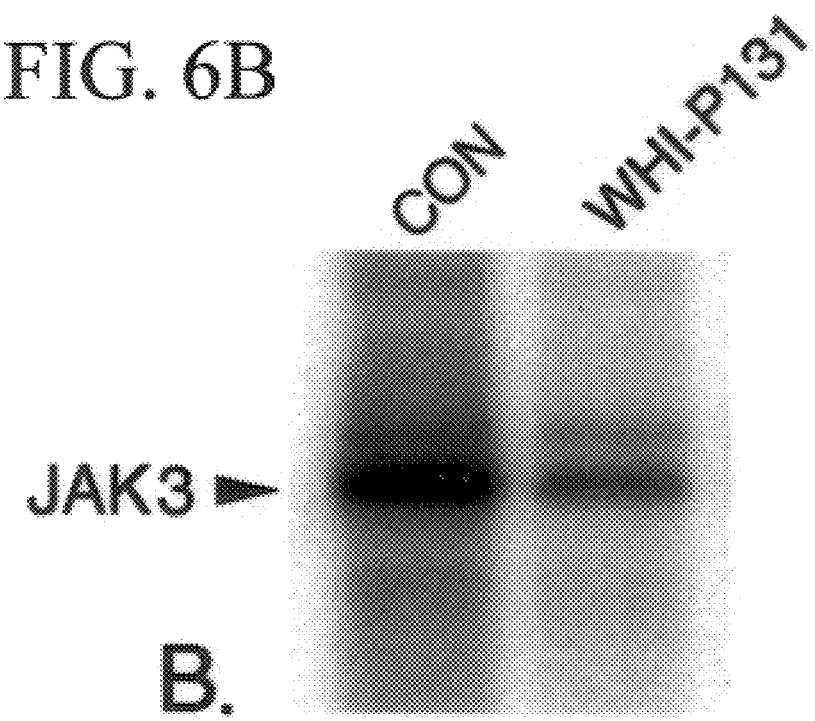
Figure 6C:
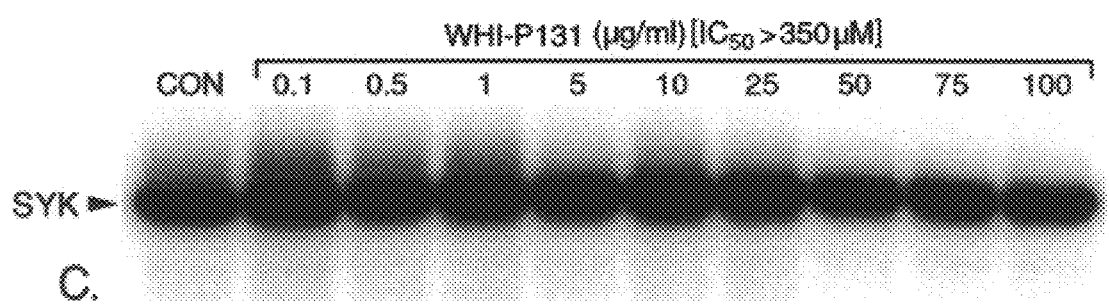
Figure 6D:
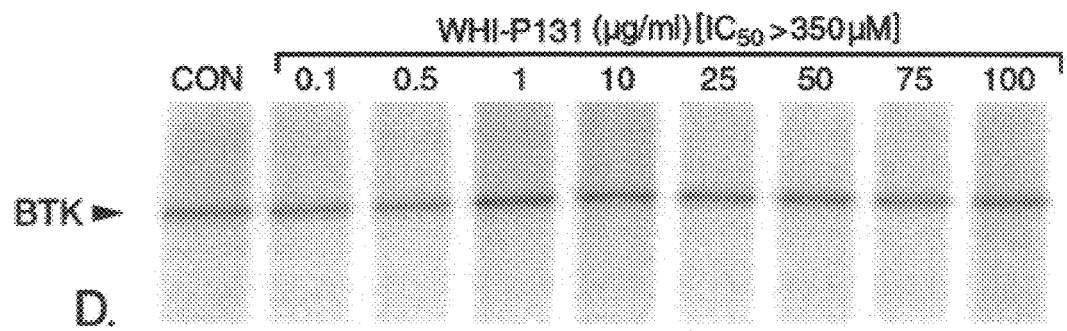

Specificity of WHI-P131 as a Tyrosine Kinase Inhibitor. Compound WHI-P131 was selected for further experiments designed to examine the sensitivity of non-Janus family protein tyrosine kinases to this novel dimethoxyquinazoline class of JAK3 inhibitors. The inhibitory activity of WHI-P131 against JAK3 was specific since it did not affect the enzymatic activity of other protein tyrosine kinases (Table 1, FIG. 6), including the ZAP/SYK family tyrosine kinase SYK (FIG. 6C), TEC family tyrosine kinase BTK (FIG. 6D), SRC family tyrosine kinase LYN (FIG. 6E), and receptor family tyrosine kinase IRK (FIG. 6F) even at concentrations as high as 350 μM.

A structural analysis of these PTKs was performed using the crystal structures of HCK (which served as a homology model for LYN) and IRK, and constructed homology models of JAK3, BTK, and SYK. This analysis revealed some nonconserved residues located in the catalytic binding site of the different tyrosine kinases which may contribute to the specificity of WHI-P131 (FIG. 4). One such residue which is located closest to the docked inhibitors is Ala966 in JAK3 (shown in region E in FIG. 4) which may provide the most favorable molecular surface contact with the hydrophobic phenyl ring of WHI-P131. The fact that WHI-P131 did not inhibit LYN, even though LYN contains the Ala residue conserved in JAK3 (Ala966), suggests that other factors (residue differences) contribute to this selectivity. Other nonconserved residues in the catalytic site of tyrosine kinases are shown in regions A to F (FIG. 4). All of these differences in residues, especially residues which directly contact the bound inhibitor, may play an important role in the observed specificity of WHI-P131 for JAK3.

Example 2 demonstrates that a novel homology model of the JAK3 kinase domain can be used for structure-based design and synthesis of potent and specific inhibitors of JAK3.

Finally, the homology model uniquely indicates that the active site of JAK3 measures approximately 8 Å×11 Å×20 Å with an approximate 530 Å$^3$ volume available for inhibitor binding. Our modeling studies using the constructed homology model of JAK3 kinase also showed that there is significant opportunity for improvement of the quinazoline inhibitors. The JAK3 model shows that there is additional volume in the ATP-binding site which can be better utilized by quinazoline derivatives. The average molecular volume of our dimethoxyquinazoline compounds is 277 Å$^3$, which is well below the estimated total volume of the binding site, 530 Å$^3$. This leaves opportunities for the design of new inhibitors which have slightly larger functional groups at the 2' and 3' positions of the phenyl ring. Structural and chemical features of dimethoxyquinazoline compounds which are proposed to facilitate their binding to the Jak3 catalytic site include the following features which are illustrated in FIG. 3C: 1) The presence of a 4'—OH group on the phenyl ring, 2) the presence of a hydrogen-bond acceptor (N, carbonyl, OH) near Leu905 NH, or a hydrogen-bond donor (NH, OH) near the Leu905 carbonyl, 3) a relatively planar molecular shape to allow access to the binding site, 4) the ability to fit into a 530 Å$^3$ space defined by the residues lining the Jak3 catalytic site. These predicted binding preferences to JAK3 residues in the catalytic site can be used for the design of new and more potent inhibitors of JAK3.

The ability of a compound to act as an anti-leukemic agent can be determined using assays that are known in the art, or can be determined using assays similar to those described in Example 3.

Example 3

Leukemia Assays

The following cell lines were used in various biological assays: NALM-6 (pre-B-ALL), LC1;19 (Pre-B-ALL), DAUDI (B-ALL), RAMOS (B-ALL), MOLT-3 (T-ALL), HL60 (AML), BT-20 (breast cancer), M24-MET (melanoma), SQ20B (squamous cell carcinoma), and PC3 (prostate cancer). These cell lines were maintained in culture as previously reported (16, 17, 20, 24, 32, 33). Cells were seeded in 6-well tissue culture plates at a density of 50×10$^4$ cells/well in a treatment medium containing various concentrations of compound 6 and incubated for 24–48 hours at 37° C. in a humidified 5% $CO_2$ atmosphere.

Figure 7A:
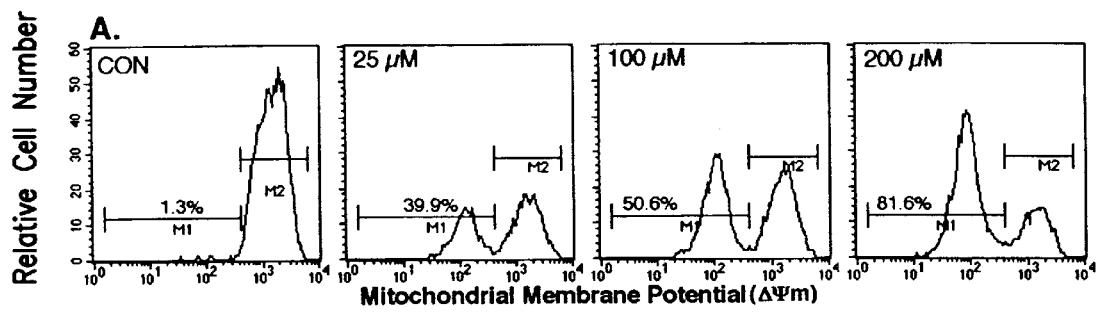
FIG. 7. WHI-P131 Depolarizes Mitochondrial Membranes in a Concentration-Dependent Fashion Without Affecting the Mitochondrial Mass. NALM-6 human leukemic cells were incubated with indicated concentrations of WHI-P131 for 48 h, stained with DiIC1 to assess the mitochondrial membrane potential (Δψm) or NAO to detect the mitochondrial mass and then analyzed with cell sorter equipped with HeNe laser. WHI-P131 caused a progressive increase in depolarized mitochondria (as indicated by M1 in A) with increasing concentrations. At similar concentrations no significant change in mitochondrial mass [B] was detected. [C]: Cells were stained with JC-1 for simultaneous analysis of mitochondrial mass (green fluorescence) and mitochondrial transmembrane potential (red/orange fluorescence). Untreated NALM-6 cells [D.1] as well as NALM-6 cells treated with 50 $\mu$M of WHI-P131 for 24 hr [D.2] were incubated with JC-1 and analyzed by confocal laser scanning microscopy. Mitochondria of control cells showed a higher membrane potential ($\Delta\psi$m), as indicated by brighter JC-1 red fluorescence. Treatment of cells with WHI-P131 reduced mitochondrial membrane $\Delta\psi$m as indicated by a substantial decrease in JC-1 red fluorescence.
Figure 7B:
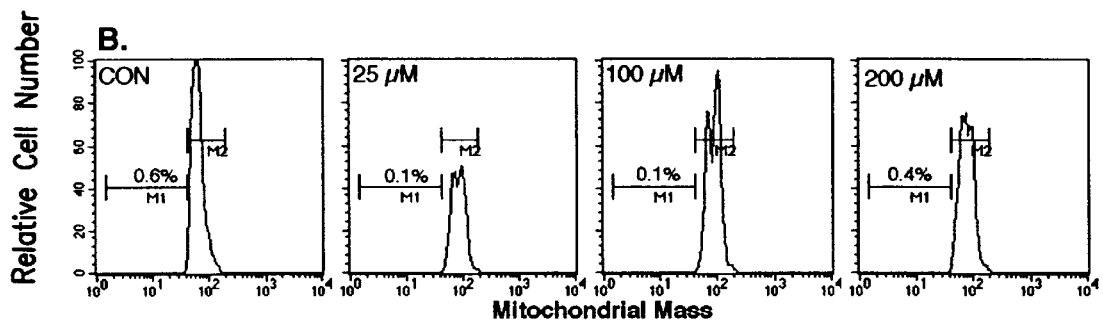

To test the cytotoxicity of compound 6 against JAK-3 expressing human leukemia cells, leukemic cells were exposed to this JAK 3 inhibitor and monitored for apoptosis-associated changes in mitochondrial membrane potential (Δψm) and mitochondrial mass using specific fluorescent mitochondrial probes and multiparameter flow cytometry. To measure changes in Δψm, DiIC1 (which accumulates in energized mitochondria) was used, whereas the mitochondrial mass was determined by staining the cells with NAO, a fluorescent dye that binds to the mitochondrial inner membrane independent of energetic state. Treatment of NALM-6 leukemia cells with compound 6 at 7.4 μg/ml (25 μM) to 60 μg/ml (200 μM) for 24 h or 48 h increased the number of depolarized mitochondria in a concentration—and time—dependent manner as determined by flow cytometry using DiIC1 (27–29) (FIG. 7A). As shown in FIG. 7A, the fraction of DiIC1-negative cells with depolarized mitochondria increased from 1.3% in vehicle treated control cells to 81.6% in cells treated with 200 μM compound 6 for 48 hours. The average $EC_{50}$ values for compound 6 induced depolarization of mitochondria, as measured by decreased DiIC1 staining, were 79.3 μM for a 24 hour treatment and 58.4 μM for a 48 hour treatment. The observed changes in Δψm were not due to loss in mitochondrial mass, as confirmed by a virtually identical staining intensity of NAO in the treated and untreated NALM-6 cells (FIG. 7B). To further confirm this relative change in Δψm, we used JC-1, a mitochondrial dye, which normally exists in solution as a monomer emitting green fluorescence and assumes a dimeric configuration emitting red fluorescence in a reaction driven by mitochondrial transmembrane potential (Smiley, S. T., et al., *Proc. Natl. Acad. Sci. U.S.A.* 88: 3671–3675, 1991). Thus, the use of JC-1 allows simultaneous analysis of mitochondrial mass (green fluorescence) and mitochondrial transmembrane potential (red/orange fluorescence). After treatment of NALM-6 cells with compound 6 at increasing concentrations ranging from 25 μM to 200 μM and with increasing duration of exposure of 24 h or 48 h, we observed a progressive dissociation between Δψm and mitochondrial mass, with decrement in JC-1 red/orange fluorescence without a significant corresponding drop in JC-1 green fluorescence (FIGS. 7C&D).

Figure 7C:
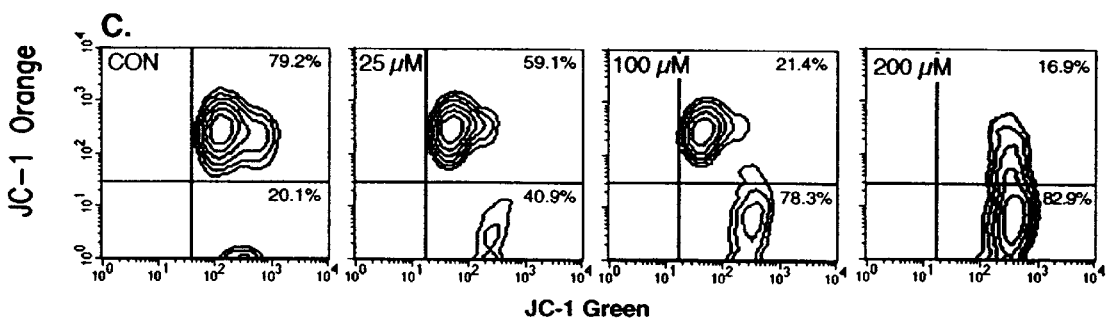

As shown in FIG. 7C, the fraction of JC-1 red/orange fluorescence-negative cells decreased from 79.2% in vehicle-treated control cells to 16.9% in cells treated with 200 μM compound 6 for 48 hours. The corresponding values for JC-1 green fluorescence were 99.3% for vehicle-treated cells and 99.8% for compound 6-treated (200 μM×48 hours) cells. The average $EC_{50}$ values for compound 6 induced depolarization of mitochondria, as measured by decreased JC-1 red/orange fluorescence were 94.2 μM for a 24 hour treatment and 50.4 μM for a 48 hour treatment. FIG. 7D compares the single color (red/orange) fluorescent confocal images of vehicle-treated and compound 6-treated (100 μM×48 hours) NALM-6 cells stained with JC-1. These results collectively demonstrate that compound 6 causes a significant decrease in mitochondrial transmembrane potential in NALM-6 human leukemia cells.

Apoptosis Assays

Cells were examined for apoptotic changes after treatment with compound 6 by the in situ terminal dideoxynucleotidyl transferase-mediated dUTP end-labeling (TUNEL) assay using the ApopTag apoptosis detection kit (Oncor, Gaithersburg, Md.) according to the manufacturer's recommendations, as detailed in our earlier reports (Zhu, D.-M., et al., *Clin. Can. Res.* 4: 2967–2976, 1998; D'Cruz, O., P., G., and Uckun, F. M. *Biology of Reproduction.* 58: 1515–1526, 1998).

To detect apoptotic fragmentation of DNA, cells were harvested after a 24 hour exposure at 37° C. at 1, 3, and/or 10 μM concentrations. DNA was prepared from Triton-X-100 lysates for analysis of fragmentation (21). In brief, cells were lysed in hypotonic 10 mmol/L Tris-HCl (pH 7.4), 1 mmol/L EDTA, 0.2% Triton-X-100 detergent; and subsequently centrifuged at 11,000 g. To detect apoptosis-associated DNA fragmentation, supernatants were electrophoresed on a 1.2% agarose gel, and the DNA fragments were visualized by ultraviolet light after staining with ethidium bromide.

Figure 8A:
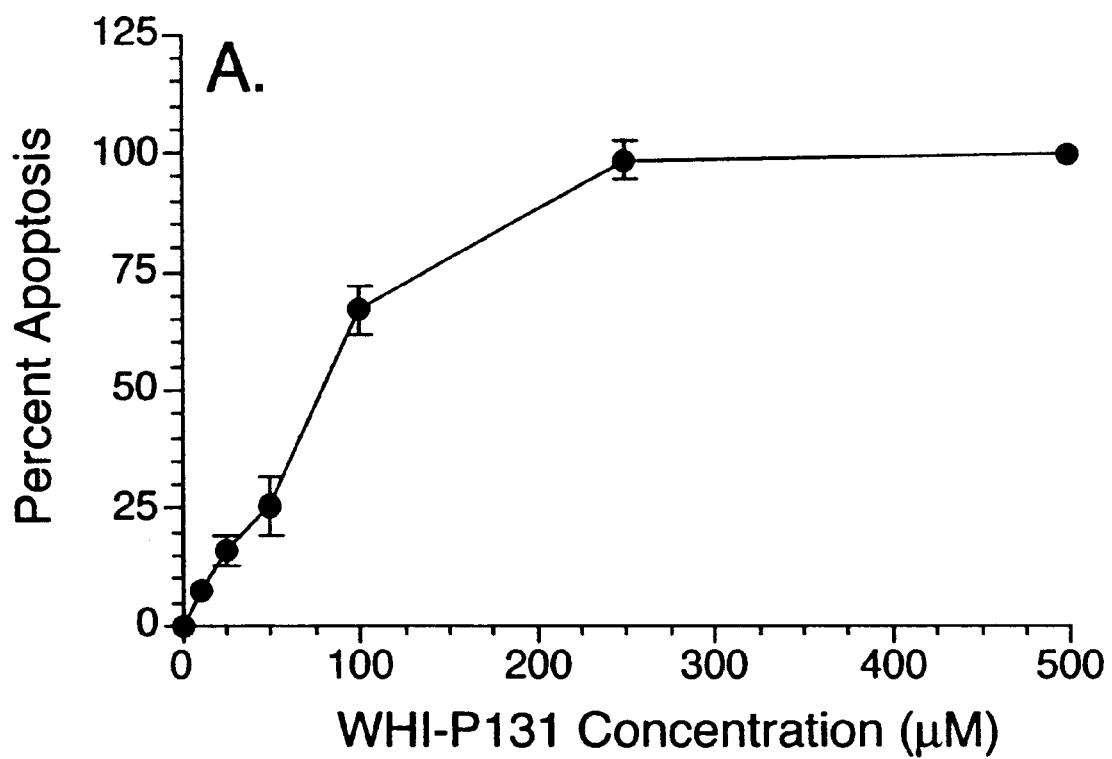
FIG. 8. WHI-P131 Induces Apoptosis in NALM-6 Leukemia Cells. [A]: Cells were incubated with 10 $\mu$M–500 $\mu$M WHI-P131 for 24 hours and then processed for in situ apoptosis assays. The percentage of apoptotic cells was determined by examining an average of 1380 cells/10 fields/sample. Data points represent the mean from duplicate counts obtained in two independent experiments. [B.1], [B.2]: NALM-6 cells were incubated with 100 $\mu$M of WHI-P131 for 48 hr, processed for the in situ apoptosis assay and analyzed with a laser scanning confocal microscope. When compared with controls treated with DMSO (0.1%) [B.1], several of the cells incubated with WHI-P131 [B.2] showed apoptotic nuclei (yellow fluorescence). Red fluorescence represents nuclei stained with propidium iodide.

To confirm that compound 6 can induce apoptosis in leukemia cells, the TdT-mediated labeling of 3'—OH termini with digoxigenin-conjugated UTP using the in situ TUNEL assay method combined with confocal laser scanning microscopy was employed. At 48 hours after treatment with compound 6 at concentrations ranging from 10 μM to 500 μM, NALM-6 cells were examined for digoxigenin-dUTP incorporation using FITC-conjugated anti-digoxigenin (green fluorescence) and propidium iodide counterstaining (red fluorescence). The percentage of apoptotic cells increased in a concentration-dependent fashion with an average $EC_{50}$ value of 84.6 μM (FIG. 8A). FIGS. 8B.1 and 8B.2 depict the two-color confocal microscopy images of vehicle-treated control cells and cells treated with 100 μM compound 6.Compound 6-treated cells showed apoptotic yellow nuclei (=superimposed green and red fluorescence) (FIG. 8B.2). Further evidence for apoptosis was observed in DNA fragmentation assays. Because of their exquisite sensitivity in detecting DNA fragments released from a small percentage of apoptotic cells, the DNA gel assays of apoptosis are uniquely suited to examine the nonspecific toxicity of new antileukemic agents.

Figure 9A:
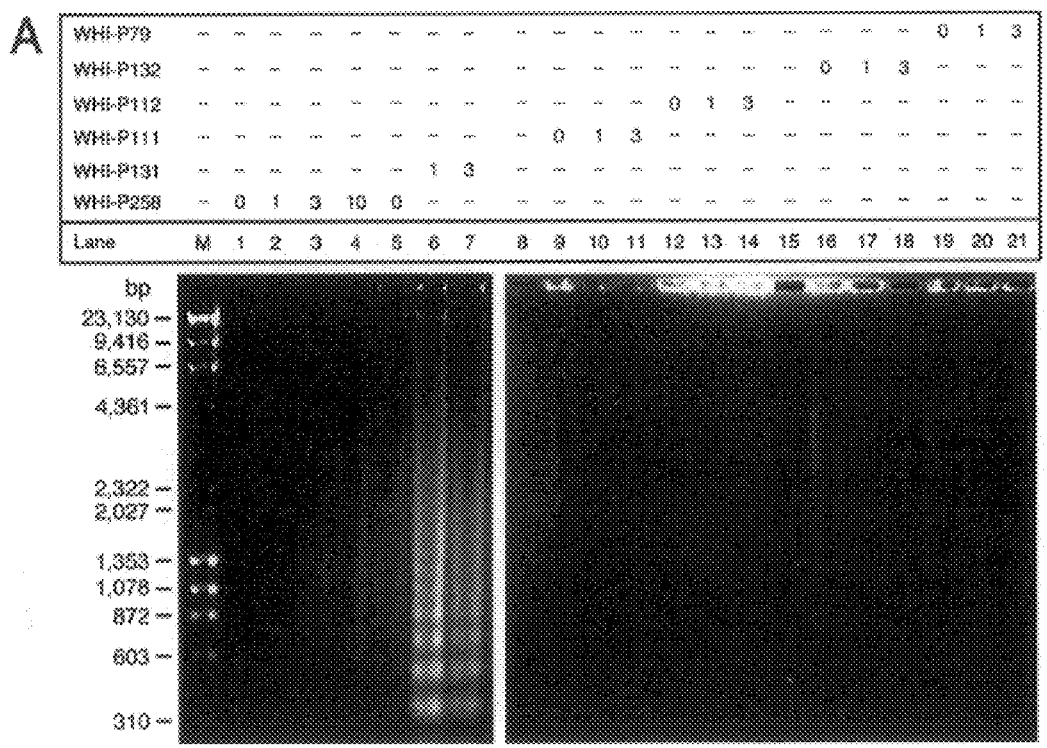
FIG. 9. WHI-P131 Induces Apoptotic DNA Fragmentation in Human Leukemia Cells. DNA from Triton-X-100 lysates of control and drug treated cells was analyzed for fragmentation, as described (21). [A] NALM-6 human B-lineage ALL cells were treated for 24 hours at 37° C. with the listed dimethoxyquinazoline compounds at 1, 3, or 10 $\mu$M final concentrations. WHI-P131 was used as the lead JAK3 inhibitory compound and all other compounds were included as controls which lacked JAK3 inhibitory activity. [B] LC1; 19 human B-lineage ALL cells and the control cell lines SQ20B and M24-MET were treated for 24 hours at 37° C. with WHI-P131 at 1 or 3 $\mu$M final concentrations.
Figure 9B:
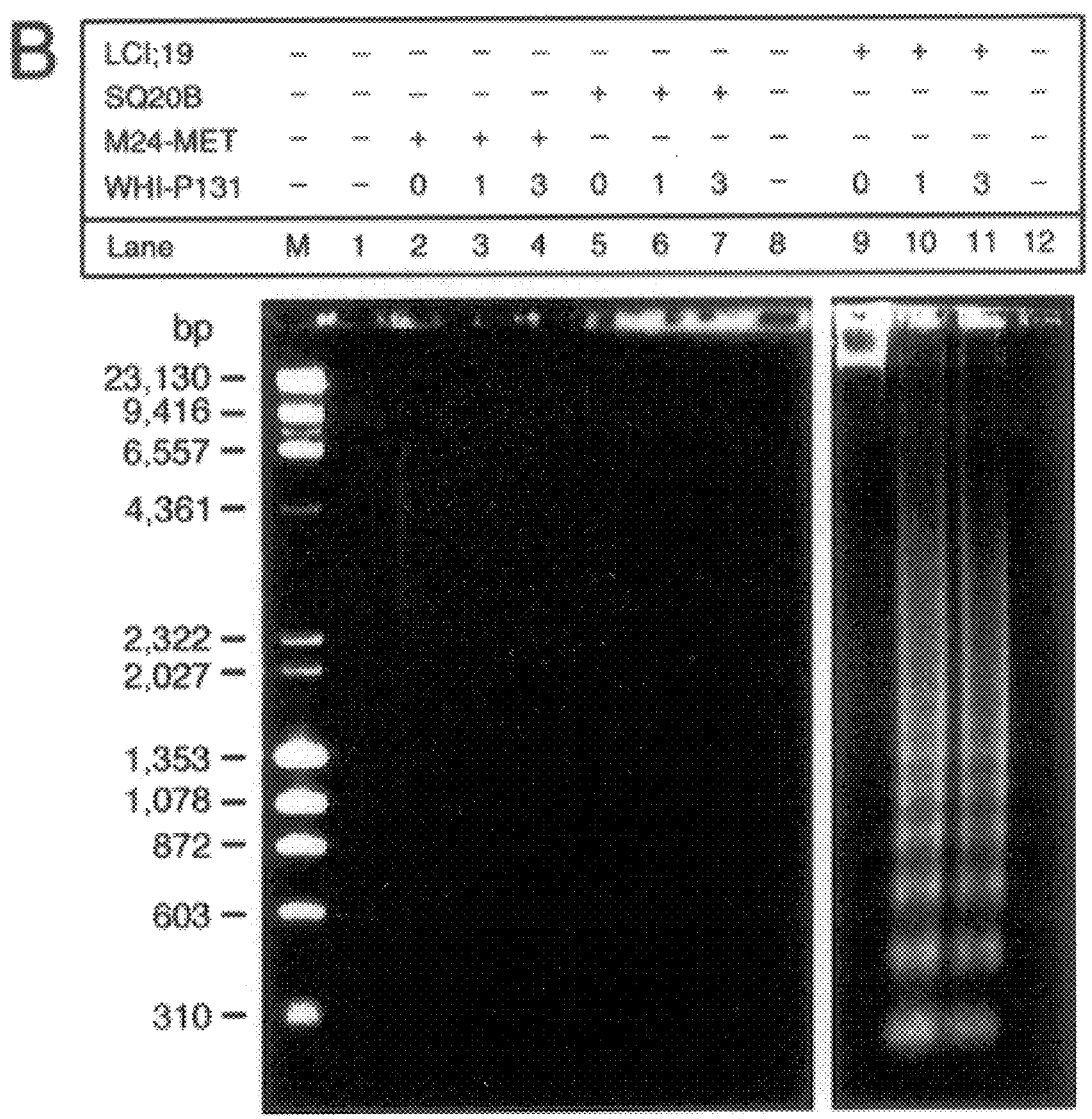

FIG. 9A demonstrates that supernatants from NALM-6 leukemia cells, treated with 1 μM or 3 μM COMPOUND 6, contained oligonucleosome-length DNA fragments with a "ladder-like" fragmentation pattern consistent with apoptosis, whereas no DNA fragments were detected in supernatants of NALM-6 cells treated with structurally similar dimethoxyquinazoline compounds which lacked JAK 3 inhibitory activity. Unlike JAK 3-positive leukemia cells (NALM-6 cells in FIG. 9A and LC 1; 19 cells in FIG. 9B), JAK 3 negative SQ20B squamous carcinoma cells and M24-MET melanoma cells did not show any evidence of apoptotic DNA fragmentation after treatment with compound 6 (FIG. 9B).

Taken together, these results provided experimental evidence that the JAK 3 specific tyrosine kinase inhibitor compound 6 results in depolarization of the mitochondrial membrane and triggers apoptotic death in human B-lineage ALL cells, as evidenced by the ladder-like fragmentation pattern of nuclear DNA and digoxigenin-11-UTP labeling of the exposed 3'-hydroxyl end of the fragmented nuclear DNA in the presence of TdT.

Clonogenic Assays

The antileukemic activity of compound 6 against clonogenic tumor cells was examined using a methylcellulose colony assay system (Uckun, F. M., et al., *J. Exp. Med.* 163: 347–368, 1986; Messinger, Y., et al., *Clin Cancer Res.* 4: 165–70, 1998). In brief, cells ($10^5$/ml in RPMI-10% FBS) were treated overnight at 37° C. with compound 6 at varying concentrations. After treatment, cells were washed twice, plated at $10^4$ or $10^5$ cells/ml in RPMI-10% FMS-0.9% methylcellulose in Petri dishes, and cultured for 7 days at 37° C. in a humidified 5% $CO_2$ incubator. Subsequently, leukemic cell (or tumor cell) colonies were enumerated using an inverted phase-contrast microscope. The percent inhibition of colony formation was calculated using the following formula:

$$\% \text{ Inhibition} = 1 - \frac{\text{mean number of colonies in test culture} \times 100}{\text{mean number of colonies in control culture}}$$

The antileukemic activity of compound 6 was measured by determining its ability to inhibit the in vitro clonogenic growth of the ALL cell lines NALM-6, DAUDI, LC1; 19, RAMOS, MOLT-3, and the AML cell line HL-60. As detailed in Table 1, compound 6 inhibited clonogenic growth in a concentration-dependent fashion with $EC_{50}$ values of 24.4 μM for NALM-6 cells and 18.8 μM for DAUDI cells. At 100 μM, compound 6 inhibited the in vitro colony formation by these leukemia cell lines by >99%. In contrast, compound 6 did not inhibit the clonogenic growth of JAK3-negative M24-MET melanoma or SQ20B squamous carcinoma cell lines

TABLE 1

Effects of Compound 6 Against Clonogenic Leukemic Cells.

| Experiment Number | (6) Concn. ($\mu$M) | Mean No. of Colonies/$10^5$ Cells | % Inhibition | Mean No. of Colonies/$10^5$ Cells | % Inhibition |
|---|---|---|---|---|---|
| | | NALM-6 (pre-B ALL) | | BT20 (Breast Cancer) | |
| 1 | 0 | 2890 (2660, 3120) | N.A. | 2676 (2712, 2640) | N.A. |
| | 0.1 | 2970 (2756, 3184) | 0 | N.D. | N.D. |
| | 1 | 3180 (3080, 3136) | 0 | N.D. | N.D. |
| | 10 | 1932 (1864, 2000) | 33.2 | 3298 (2940, 3656) | 0 |
| | 100 | 2 (2,2) | >99.9 | 2190 (1632, 2748) | 18.2 |
| | | DAUDI (B-ALL) | | M24-MET (Melanoma) | |
| 2 | 0 | 3950 (3100, 4800) | N.A. | 177 (120, 235) | N.A. |
| | 0.3 | 2030 (1700, 2360) | 48.6 | 312 (238, 386) | 0 |
| | 1 | 2136 (1568, 2704) | 45.9 | 287 (157, 418) | 0 |
| | 3 | 1406 (988, 1824) | 64.4 | 390 (280, 500) | 0 |
| | 10 | 1149 (1054, 1244) | 70.9 | 301 (249, 353) | 0 |
| | 30 | 29 (12, 46) | 98.0 | 599 (534, 664) | 0 |
| | | RAMOS (B-ALL) | | SQ20B (Squamous Carcinoma) | |
| 3 | 0 | 1286 (1164, 1408) | N.A. | 754 (452, 1056) | N.A. |
| | 30 | 2 (0, 4) | 99.8 | 838 (600, 1076) | 0 |
| | | MOLT-3 (T-ALL) | | HL-60 (AML) | |
| | 0 | 1322 (1252, 1392) | N.A. | 1854 (1648, 2060) | N.A. |
| | 100 | 1 (1, 1) | >99.9 | 1 (1, 1) | >99.9 |

*Cells were treated with COMPOUND 6 and then assayed for colony formation as described in Methods.
N.A. = not applicable,
N.D. = not determined In other studies, compound 6 was shown to inhibit JAK 3, but not other protein tyrosine kinases, including JAK 2, SYK, BTK, LYN, and IRK. ALL cells express JAK 2. Similarly, the Src family PTK LYN, Zap/Syk family PTK SYK, and Tec family PTK BTK are expressed in ALL cells and affect their adhesion, proliferation, and survival (Vassilev, A., et al., *J. Biol. Chem.* 274: 1646–1656, 1999; Uckun, F. M., et al., *Science.* 267: 886–91, 1995; Kristupaitis, D., et al., *J. Biol. Chem.* 273 (15): 9119–9123, 1998; and Xiao, J., et al., *J. Biol. Chem.* 271: 7659–64, 1996). IRK is the only member of the receptor PTK family that has been detected in leukemic cells, especially pre-B ALL cells with a t(1; 19) translocation (41–43). Since compound 6 does not inhibit these tyrosine kinases, its ability to kill ALL cells cannot be attributed to a nonspecific inhibition of JAK 2, LYN, SYK, BTK, or IRK in these cells (Kaplan, G. C., et al., *Biochem. Biophys. Res. Commun.* 159(3): 1275–82, 1989; Newman, J. D., et al., *Int. J. Cancer.* 50 (3): 500–4, 1992; Bushkin, I. and Zick, Y., *Biochem. Biophys. Res. Commun.* 172(2): 676–82, 1990).

The above shows that a representative JAK-3 inhibitor of formula I (Compound 6) is a useful therapeutic agent for treating acute lymphoblastic leukemia, and demonstrates that compound 6 triggers apoptosis in leukemia cells. Thus, potent and specific inhibitors of JAK 3, such as dimethoxyquinazolines of formula I are useful for treating acute lymphoblastic leukemia, which is the most common form of childhood cancer.

The ability of a compound to prevent or treat skin cancer can be determined using assays that are known in the art, or can be determined using assays similar to those described in Example 4.

Example 4

Skin Cancer Assays

Female, 6–7 weeks old, hairless albino mice (skh-1) were purchased from Charles River Laboratories (Wilmington, Mass.) and were housed in a controlled environment (12-h light/12-h dark photo period, 22±1° C., 60±10% relative humidity), which is fully accredited by the USDA (United States Department of Agriculture). Animals were caged in groups of five in a pathogen free environment in accordance with the rules and regulations of U.S. Animal Welfare Act, and National Institutes of Health (NIH). All mice were housed in microisolator cages (Lab Products, Inc., N.J.) containing autoclaved bedding. The mice were allowed free access to autoclaved pellet food and tap water throughout the experiments. Animal care and the experimental procedures were carried out in agreement with institutional guidelines.

Buffered formalin phosphate (10%) was obtained from Fisher scientific (Springfield, N.J.). Dimethyl sulfoxide (DMSO) and Phosphate buffered saline (PBS) were purchased from Sigma (St. Louis, Mo.).

Ultraviolet lamps (8-FSX24T12/HO/UVB) that emit light predominantly in the UVB range (280–320 nm) were obtained from National Biological Corporation, Twinsburg, Ohio. The irradiance of the UVB lamps was determined before each irradiation, using a UVB meter (model - 500C obtained from National Biological Corporation, Twinsburg, Ohio). For exposure to UV light, three mice were placed in an open 28 cm×10 cm plastic box that was divided in three compartments (one mouse per compartment). The plastic box was placed in the center, under the bank of UVB light, and the mice were irradiated with 35 mj/cm² dose of UVB. The exposure time for a 35 mj/cm² dose of UVB varied from 30–34 s. The distance between UVB lamps and the surface receiving irradiation was 20 cm.

Tumorigenesis Protocol: Mice were divided into three groups containing 5–14 mice per group as shown in Table 1. The mice were treated topically with a single application of Compound 6 (1.0 mg/cm², dissolved in DMSO) over a 2 cm² area on the dorsal surface before each UVB exposure. After 15 min. following Compound 6 application the mice were irradiated with UVB (35 mj/cm²). UVB exposure of mice was performed three times a week for a total of 20 weeks. Control mice were treated with vehicle prior to UVB light exposure.

TABLE 1

Experimental Design and Treatment Regimen

| Group | No. of Mice | Treatment | UVB (35 mj/cm²) |
|---|---|---|---|
| A | 5 | Vehicle | – |
| B | 10 | Vehicle | + |
| C | 14 | Compound 6 (1 mg/cm²) | + |

The skin thickness of mice, and papillary skin lesions greater than 1 mm in diameter were measured and recorded twice every week and the average of the two measurements was used in the calculations. Skin thickness, lesion number and lesion diameter measurements were limited only to the 2 cm² area on the dorsal surface of mice that was being treated either with compound 6 or vehicle. Lesion volume were calculated using the formula:

$$Volume = 4/3\pi r^3$$

At the end of the study, 5–19 lesions from each group were randomly biopsied, and fixed in 10% buffered formalin. Formalin-fixed specimens were embedded in paraffin blocks, sectioned at 4 μm thickness, and stained in haematoxylin-eosin. The pathological evaluation of skin sections was performed by a Certified Veterinary Pathologist who was unaware of the identity of specimens.

Pathological classification of tumors: The pathological classification of tumors was as follows: 1) Cutaneous papilloma: a tumor papillomatous growth of acanthotic epidermis without invasive growth of tumor cells into the dermis. Tumor cells do not appear atypical. 2) Actinic keratosis: a hyperplastic, orthokeratotic, mildly to moderately acanthotic epithelium. 3) Florid actinic keratosis: actinic keratosis with mild to moderately acanthotic ridges extending into the superficial dermis, resembling superficially invasive squamous cell carcinoma. 4) Keratoacanthoma: a papillary growth with a central keratin filled crater surrounded by hyperplastic, acanthotic stratified squamous epithelium. The leading edge of the tumor pushes into the underlying dermis. 5) Squamous cell carcinoma (SCC): a tumor with atypical cell nests invading into superficial and mid dermis.

Results for Example 4.

Figure 10:
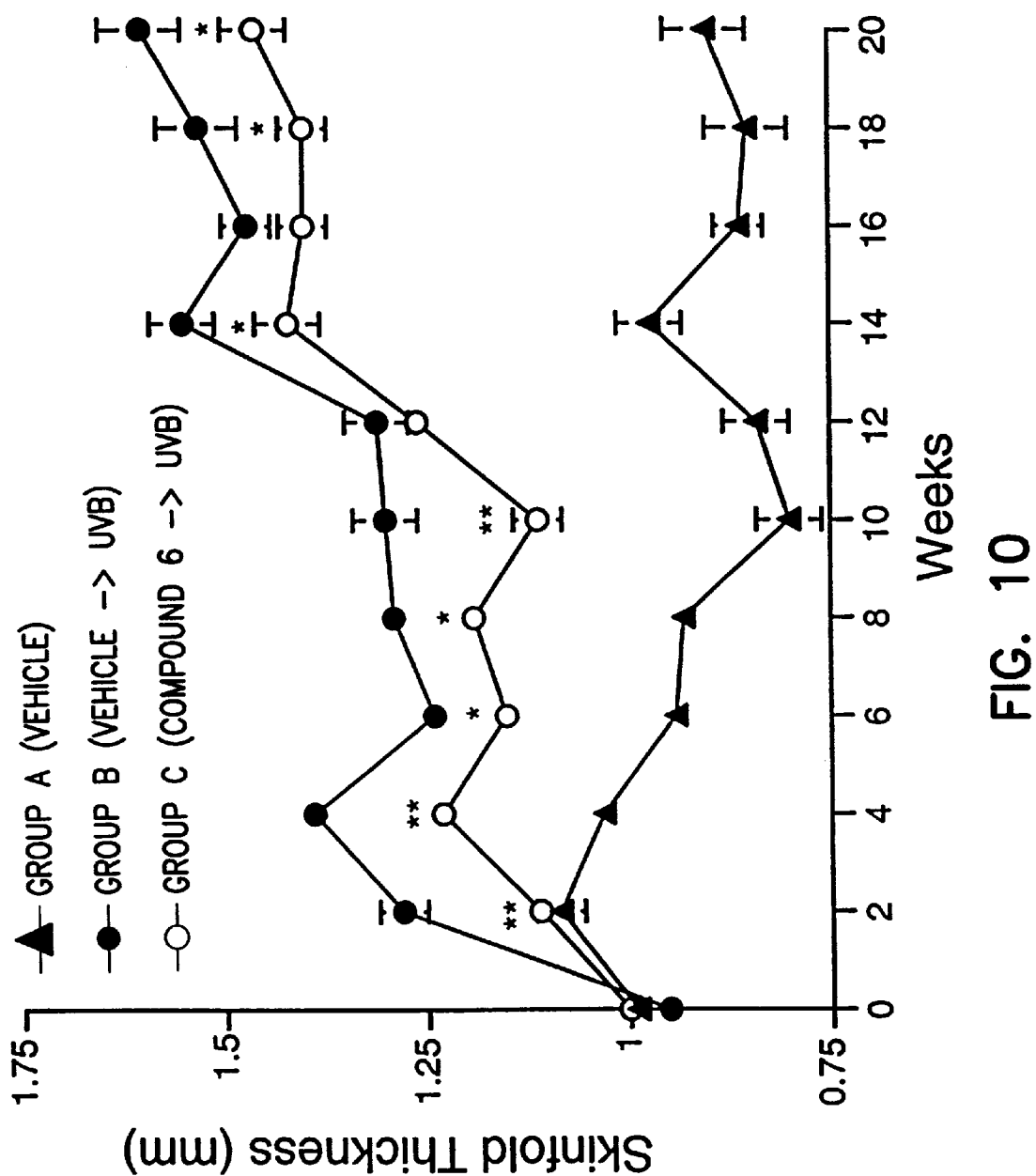
FIG. 10. Inhibitory effect of compound 6 on UVB-induced skin thickness in skh-1 mice. Female skh-1 mice were treated topically with 1 mg/cm$^2$ of compound 6 prior to each UVB light exposure with 35 mj/cm$^2$. Skinfold thickness of each mouse was recorded twice weekly and the average of the two measurements was used in calculations. Data represent mean±SEM (n=5–14). * P$\leq$0.05 and ** P$\leq$0.005 as compared to vehicle treated control.

Sunburn is a UV induced inflammatory reaction that is characterized by cutaneous vasodilatation (erythema), and an increase in vascular permeability with exudation of fluid (edema) in the affected skin. The UVB-induced increase in plasma exudation can be detected as an increase in skinfold thickness at 24 h following irradiation (Berg, R. J., et al., 1998, *J Invest Dermatol* 110:405–9). Exposure of mice to UVB light (group B) induced an increase in skinfold thickness as compared to the skin thickness of control group mice (FIG. 10). In the compound 6 treated group (group C) there was an increase in skin thickness as compared to the control (group A); however, the increase in skin thickness was significantly less as compared to UVB-irradiated and vehicle-treated group of mice indicating the anti-inflammatory effect of compound 6. Since the mice were irradiated chronically three times a week, a sustained increase in skin edema was observed during the course of the study in UVB-irradiated mice (groups B & C). However, at any given time point the increase in skin edema was partially inhibited by compound 6 in the drug treated mice.

Figure 11:
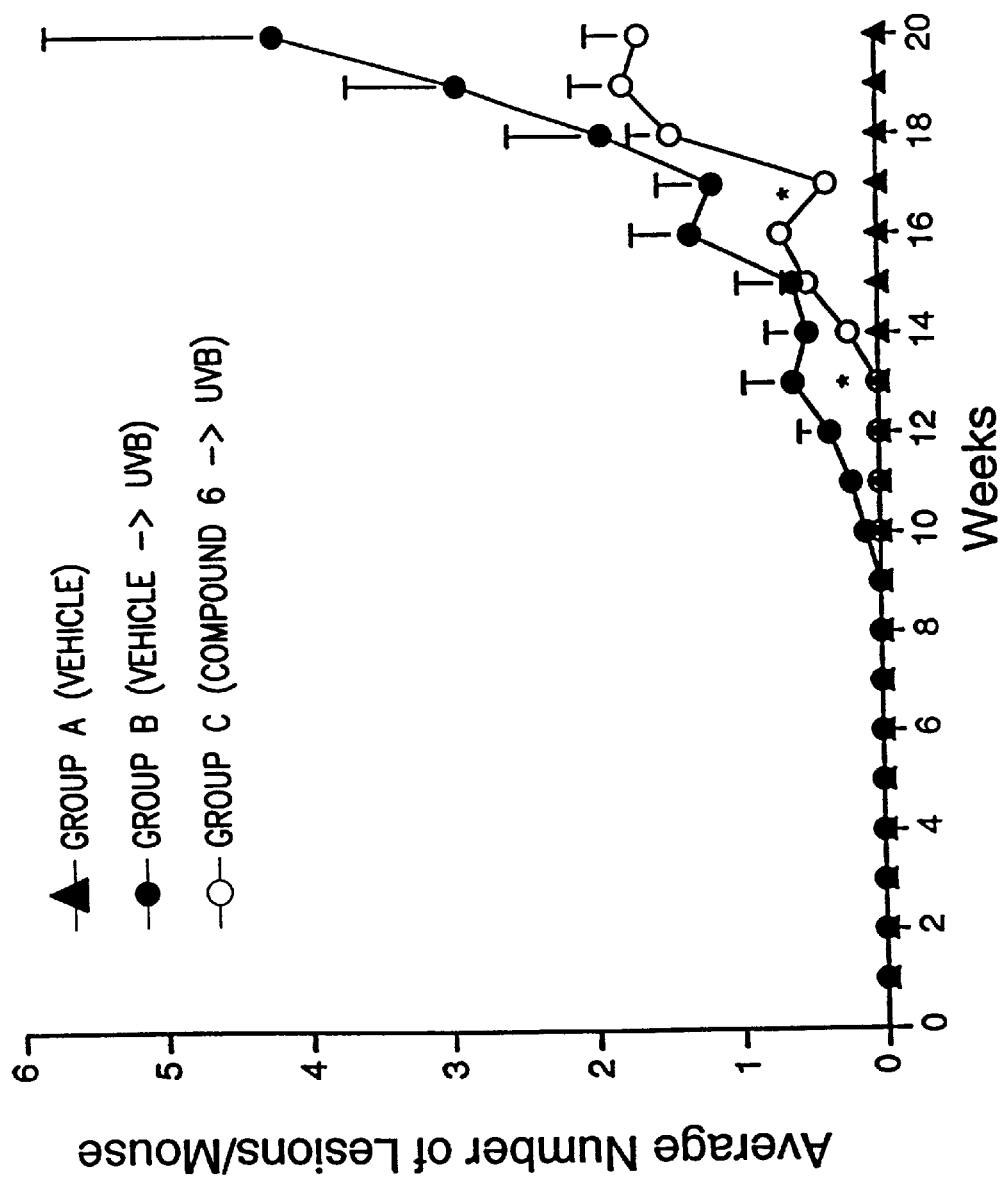
FIG. 11. Inhibitory effect of compound 6 on the average number of lesions per mouse. Female skh-1 mice were treated topically with 1 mg/cm$^2$ of compound 6 prior to each UVB light exposure with 35 mj/cm$^2$. The number of lesions was recorded twice weekly and the average of the two measurements was used in calculations. Data represent mean±SEM (n=5–14). * P<0.05 as compared to vehicle treated control.

Chronic exposure of skin to UVB radiations primarily leads to the development of fine skin lesions that can grow both in number as well as size with further exposures to such radiations. As shown in FIG. 11, the chronic UVB exposure of mice induced the appearance of fine lesions in the affected skin that first appeared around 10 weeks of irradiation in the vehicle-treated and UVB-irradiated group of mice (group B). The total number of skin lesions increased exponentially with increasing numbers of UVB-exposure in the UVB-irradiated group of mice (group B). However, in COMPOUND 6-treated mice (group C), the onset of lesions was delayed; the first lesion was observed after 14 weeks of UVB-irradiation. Although the average number of lesions per mouse in this group also increased with increasing numbers of UVB exposures as in group B, at any given time point, the average number of lesions per mouse was always less as compared to its untreated control (group B).

This data indicate that application of compound 6 prior to UV exposure (a) delays the onset of tumor from 10 weeks of UVB treatment (group B) to 14 weeks, and (b) it inhibits the total number of lesions resulting from repeated UVB exposure.

Figure 12:
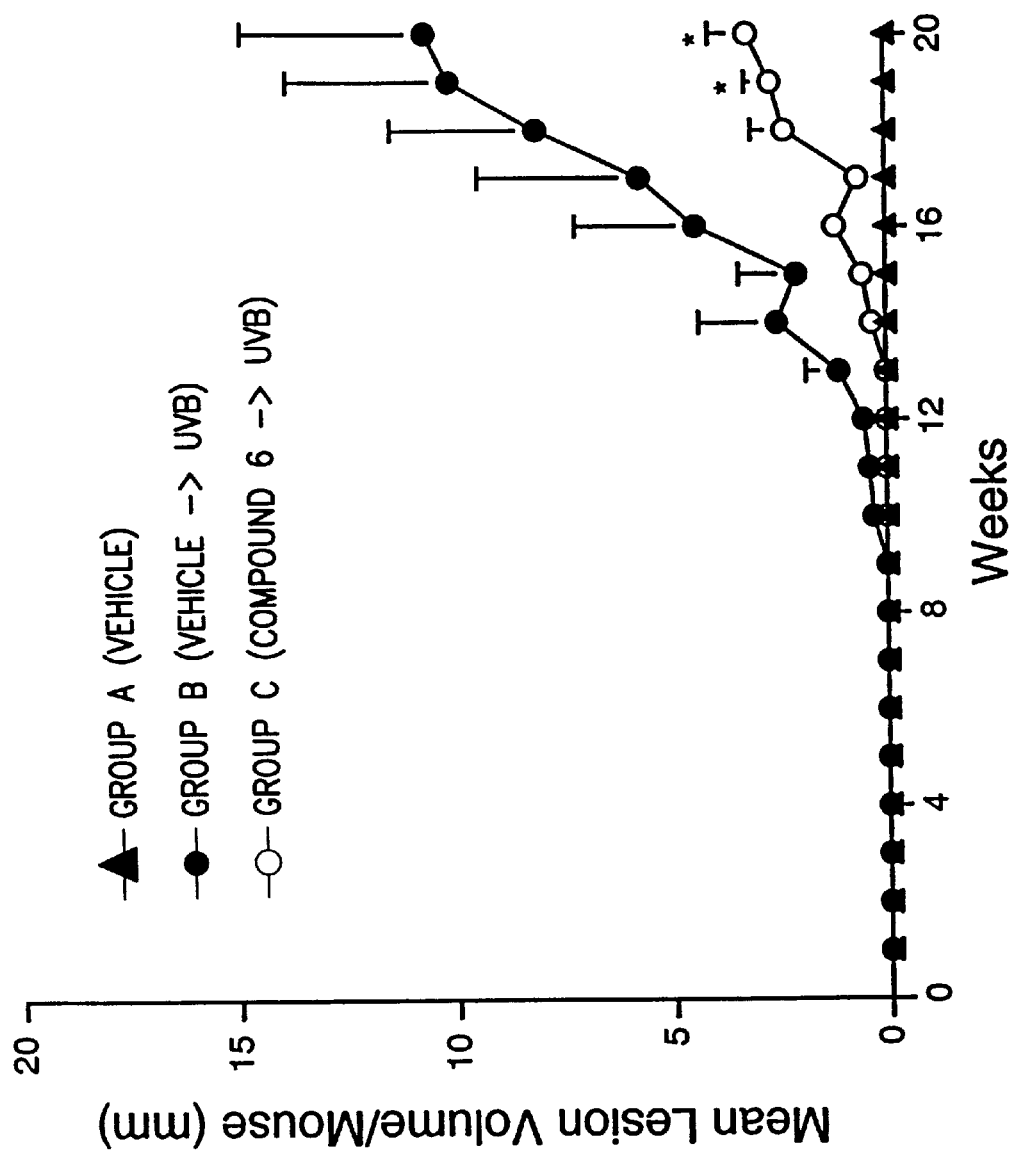
FIG. 12. Inhibitory effect of Compound 6 on the average lesion volume per mouse. Female skh-1 mice were treated topically with 1 mg/cm$^2$ of compound 6 prior to each UVB light exposure with 35 mj/cm$^2$. The lesions greater than or equal to 1 mm in diameter were measured and recorded twice weekly and an average of the two measurements was used in calculations. Lesion volume was calculated using the formula described in Material and Methods. Data represent mean±SEM (n=5–14). * P$\leq$0.05 as compared to vehicle treated control.

Following the first appearance around 10–14 weeks of UVB irradiation, the skin lesions increased both in total number as well as in size with increasing number of UVB exposures. In order to compare the size of skin lesions, lesion diameter was converted to lesion volume using the formula described in Materials and Methods, and average lesion volume per mouse was compared. FIG. 12 shows the effect of compound 6 treatment on average lesion volume per mouse. It is observed from the figure that the average lesion volume increased with time in both of the UVB-irradiated groups of mice (groups B & C) but compound 6 treatment of mice inhibited the increase in lesion volume (group C, FIG. 12 and Table 2). In addition, we also compared the average volume per lesion in compound 6-treated and -untreated groups of mice after 20 weeks of irradiation. As observed before, with average skin lesion volume per mouse, the average volume per lesion was also inhibited by compound 6 treatment (Table 2).

TABLE 2

Inhibitory effect of topical administration of Compound 6 on UVB-induced tumorigenesis in skh-1 mice

| Group | No of mice | No. of lesions/ mouse | Skin lesion volume/ mouse | Avg. Vol/ lesion |
|---|---|---|---|---|
| A | 5 | 0 | 0 | 0 |
| B | 10 | 4.2 ± 1.6 | 10.6 ± 4.3 | 2.5 ± 0.5 |
| C | 14 | 1.6 ± 0.4 | 3.2 ± 0.9* | 1.9 ± 0.5 |

Female skh-1 mice (7–8 weeks old) were treated topically either with compound 6 (1 mg/cm²) or vehicle before each UVB irradiation (Irradiation Dose: 35 mj/cm²). The mice were exposed to UVB three times a week for 20 weeks. The data represent the mean ± SEM from 5–14 mice at 20 weeks.
*P < 0.05 as compared to vehicle treated control.

Figure 13A:
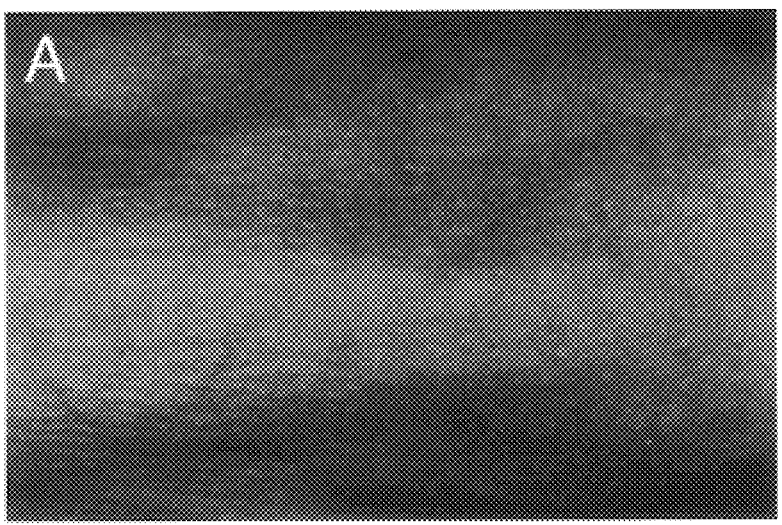
FIG. 13. Morphological appearance of dorsal surface of mice after 20 weeks of UVB irradiation. Female skh-1 mice were treated topically with 1 mg/cm$^2$ of compound 6 prior to each UVB light exposure with 35 mj/cm$^2$. Mice were irradiated three times per week for a total of 20 weeks. At 20 weeks the mice were anaesthetized, and a picture of their dorsal surface was taken. Panel A, Unirradiated and vehicle treated control. Panel B, UVB irradiated and vehicle-treated mouse. Panel C, UVB irradiated and compound 6-treated mouse. Magnification 2×.
Figure 13B:
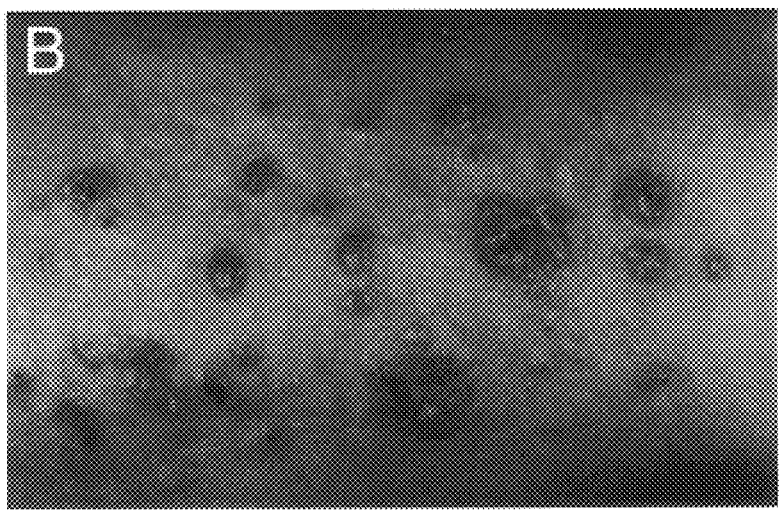
Figure 13C:
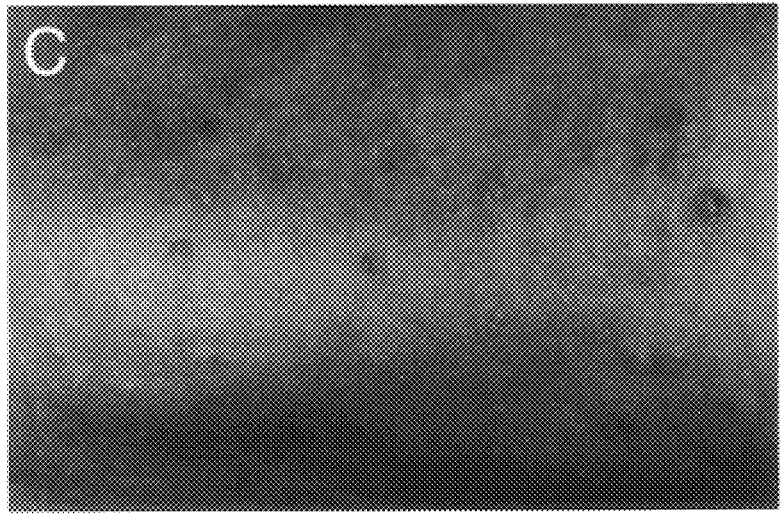

Morphological and Histopathological Data. The morphological appearance of mouse skin after 20 weeks of irradiation from all three groups of mice has been compared. The FIG. 13 shows that repeated exposure with UVB light induced the growth of a number of lesions on the affected skin (FIG. 13, Panel B) whereas treatment with compound 6 inhibited the growth of such lesions.

Histopathological findings of skin biopsies in mice after 20 weeks of UVB irradiation are presented in Table 3.

TABLE 3

Inhibitory effect of topical administration of Compound 6 on UVB-induced keratoacanthoma and squamous cell carcinomas in skh-1 mice

| Group | No of mice | Percentage of mice with Actinic keratosis | Percentage of mice with Keratoaca-nthomas | Percentage of mice with Papilloma | Percentage of mice with SCC/ Florid actinic keratosis |
|---|---|---|---|---|---|
| A | 5 | 0 | 0 | 0 | 0 |
| B | 10 | 60 | 10 | 10 | 80 |
| C | 14 | 53 | 0 | 7 | 57 |

Female skh-1 mice (7–8 weeks old) were treated topically either with compound 6 (1 mg/cm$^2$) or vehicle before each UVB irradiation (Irradiation Dose: 35 mj/cm$^2$). The mice were exposed to UVB three times a week for 20 weeks. The data represent the percentage of total no. of mice per group at 20 weeks.

A mild to moderate dermatitis was observed in all three groups including the unirradiated group of mice (group A) which could be induced by topical application of the vehicle (DMSO) three times a week during the course of the study. Actinic keratosis, which represents a hyperplastic and mild to moderately acanthotic epidermis, was present in most of the biopsies from both of the UVB irradiated groups (groups B &C). A single lesion of keratoacanthoma was observed in the UVB-irradiated and vehicle treated group of mice (group B). No such lesion was observed in any of the 14 mice in compound 6 treated group (group C). The occurrence of superficially invasive squamous cell carcinoma (Florid actinic keratosis and a precursor to SCC) and SCC was noted in both of the UVB irradiated groups (Group B &C), but in COMPOUND 6 treated mice (group C) it was inhibited by about 23% (Table 3). Similarly, the incidence of cutaneous papilloma was also partially inhibited by compound 6.

The results of Example 4 indicate that the topical application of compound 6 prior to UV irradiation protects skin from the harmful consequences of skin cancer in chronic exposure. Specifically, a topical application of compound 6 on skin before UVB light exposure markedly inhibited the formation of skin lesions, decreased tumor size and inhibited the development of tumors in skh-1 mice. Extensive documentation has validated the role of UVB radiations in skin tumor formation (Devary, Y., et al., 1992, *Cell* 71:1081–1091; Ley, R. D., et al., 1989, *Photochem Photobiol* 50: 1–5; Hall, E. J., et al., 1988, *Am J Clin Oncol* 11:220–252; and Marks, R. 1995, *Cancer* 75:607–612). UVB-irradiation of skin cells triggers the release of increased amounts of arachidonic acid and its metabolites (Konger, R. L., et al., 1998, *Biochim Biophys Acta* 1401:221–234. (12–15). Prostaglandins, which are the oxygenation product of arachidonic acid, are produced abundantly following UVB irradiation of skin cells (Hawk, J. L. M., and J. A. Parrish. 1993. *Responses of Normal Skin to Ultraviolet Radiations.* Plenum Medical Book Publishers, New York; Hruza, L. L., and A. P. Pentland. 1993, *J Invest Dermatol* 100:35–S41S; Kang-Rotondo, et al., 1993, *Am J Physiol* 264:C396–401; and Grewe, M., U. et al., 1993, *J Invest Dermatol* 101:528–31) and have been implicated in various models for tumorigenesis (Vanderveen, E. E., et al., 1986, *Arch Dermatol* 122:407–12; Cerutti, P. A., and B. F. Trump. 1991, *Cancer Cells* 3:1–7). Evidences also indicate that in addition to stimulating tumor growth, prostaglandins have a tendency to suppress hosts' immune surveillance (Plescia, O. J., et al., 1975, *Proc Natl Acad Sci USA* 72:1848–1851; Goodwin, J. S. 1984. *Am J Med* 77:7–15 and thus, assist in tumor promotion. Elevated levels of PGE$_2$ have been observed in squamous and basal cell carcinomas of skin and may be correlated with the increased metastatic activity and invasive behavior (Vanderveen, E. E., et al., 1986, *Arch Dermatol* 122:407–12; Klapan, I., V. et al., 1992, *J Cancer Res Clin Oncol* 118:308–313 of these tumors. Various chemical compounds which inhibit the production of prostaglandins have been observed to inhibit the growth of tumors (Snyderman, C. H., et al., 1995, *Arch Otolaryngol Head Neck Surg* 121:1017–1020; Hial, V., et al., 1976, *Eur J Pharmacol* 37:367–376; Lynch, N. R., et al., 1978, *Br J Cancer* 38:503–512.

The ability of compound 6 to inhibit the UVB induced skin tumorigenesis combined with our previous observations that it inhibits acute skin inflammation indicate that compound 6 is a useful chemopreventive agent against some forms of human cancers induced by environmental agents, such as ultraviolet light.

The ability of a compound to prevent or treat skin cancer can be determined using assays that are known in the art, or can be determined using assays similar to those described in Example 5.

Example 5

UVB-Induced Skin Carcinogenesis Assays

Compound 6 is able to significantly inhibit the UVB light induced inflammatory mediator release in epidermal cells and thus it prevents the inflammatory responses of UVB exposed skin.

Female, 6–7 weeks old, hairless albino mice (skh-1) were purchased from Charles River Laboratories (Wilmington, Mass.). The transgenic BigBlue mice carrying multiple copies of the BigBlue (LIZ shuttle vector which contains substrate for detection of mutations in vivo were obtained from Stratagene (La Jolla, Calif.). Mice were caged in groups of five in a pathogen free environment in accordance with the rules and regulations of U. S. Animal Welfare Act, and National Institutes of Health (NIH). Animal care and the experimental procedures were carried out in agreement with institutional guidelines.

HaCaT, which is a spontaneously transformed human epidermal cell line (16) was maintained in Dulbecco's modified Eagle's medium (DMEM) supplemented with 10% fetal bovine serum (Summit Biotech, Ft. Collins, Colo.).

A bank of 8-FSX24T12/HO/UVB lamps (National Biological Corporation, Twinsburg, Ohio) that emits light predominantly in the UVB range, 280–320 nm was used to irradiate mice and cell cultures. The irradiance of UVB lamps was always measured before irradiation using a UVB meter (model - 500C obtained from National Biological Corporation, Twinsburg, Ohio). The dose of UVB light used to irradiate cultures was 25 mj/cm$^2$. Anesthetized mice received UVB radiations to a 2.0 cm$^2$ area on their dorsal surface. This area was painted either with the test compound (1.5 mg/cm$^2$) in drug receiving mice, or with vehicle in control mice fifteen minutes before irradiation. The distance between UVB lamps and surface receiving irradiation was 20 cm. The final radiation dose received by skh-1 hairless mice was 250 mj/cm$^2$ which is approximately seven times higher than the minimal erythema dose (MED) (17) in these mice. BigBlue mice were shaved on their back before irradiation and then exposed to 400 mj/cm$^2$ UVB light either in the presence or absence of compound 6.

Prostagland E$_2$ Assay. Confluent HaCaT cells cultured in 24-well culture dishes were washed three times with serum-free DMEM containing 1% bovine serum albumin (BSA) (Cayman chemicals, Ann Arbor, Mich.) and incubated with 3–30 μM compound compound 6 for 1 hour at 37° C. After incubation the cells were washed twice with PBS, and either exposed to 25 mj/cm$^2$ UVB light or stimulated with 50 ng/ml rhEGF, and fed with serum-free DMEM containing 1% BSA. compound 6 was readministered and the cells were incubated for 6 h at 37° C. At 6 h following stimulation the cell supernatant was collected and PGE$_2$ released in cell supernatants was measured by a competitive EIA using an acetylcholine esterase-PGE$_2$ tracer and anti-PGE$_2$ antibody supplied with the ELISA kit (Cayman chemicals, Ann Arbor, Mich.). Cellular protein was determined using the Pierce's BCA protein assay method (Smith, P. K., et al., 1985, Anal Biochem. 150 (1):76–85).

Compound 6 was initially dissolved in dimethyl sulfoxide (DMSO) (Sigma, St. Louis, Mo.) at a concentration of 10 mg/ml and diluted to 1 mg/ml concentration with Phosphate buffer saline (PBS) before injection. The mice were treated daily with 16 mg/kg i.p. bolus injection of compound 6 from day −2 (i. e. 2 days prior to UVB exposure) until the termination of the experiment. Drug receiving mice were also painted with 1.5 mg/cm$^2$ of Compound 6, 15 min before irradiation. The control mice received vehicle alone.

Figure 14:
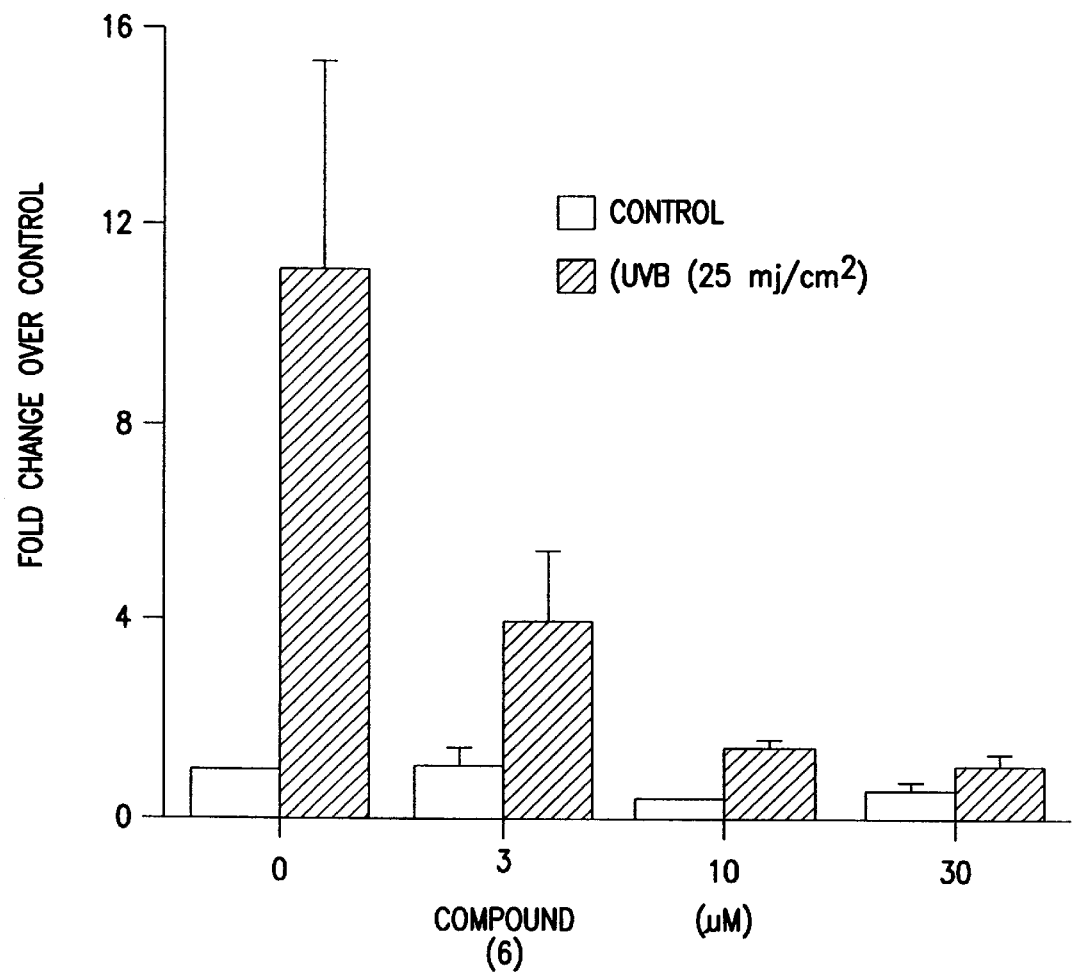
FIG. 14. Compound 6 inhibits UVB-induced PGE$_2$ synthesis. HaCaT cell cultures were either irradiated with UVB (25 mj/cm$^2$) or sham irradiated. COMPOUND 6 (3–30 (M) was added 60 min prior to irradiation and was readministered after UVB exposure. Cumulative PGE$_2$ released during subsequent 6 h incubation was determined by EIA. Data represent mean (SEM (n=3).

One of the major arachidonic acid metabolite in Ultraviolet light B-irradiated keratinocytes is prostaglandin E$_2$ which can be detected as early as 6 h, peaks between 24–48 h following UVB exposure, and induces edema and erythema in skin (Gilchrest, B. A., et al., 1981, J Am Acad Dermatol. 5 (4):411–22; Konger R. L., et al., 1998, Biochim. et Biophys. Acta (1401):221–34; Woodward, D. F., et al., 1981, Agents Actions. 11 (6–7):711–7; Snyder, D. S., and W. H. Eaglstein. 1974. Br J Dermatol. 90 (1):91–93; Snyder, D. S., and W. Eaglstein. 1974. J Invest Dermatol. 62:47–50; and Gupta, N., and L. Levy. 1973, Br J Pharmacol. 47 (2):240–8). We determined the effect of compound Compound 6 on PGE$_2$ release in UVB irradiated epidermal cells. The human epidermal cells, HaCaT, were exposed to UVB light and incubated both in the presence or absence of Compound 6 and cumulative PGE$_2$ released in cell supernatants during 6 h incubation was determined. Analysis of PGE$_2$ release (FIG. 14) showed that an exposure of HaCaTs to 25 mj/cm$^2$ UVB induced about eleven (11.11 ( 4.23) fold increase in PGE$_2$ level at 6 h post irradiation as compared to non-UVB irradiated control. The UVB light induced prostaglandin release was inhibited by Compound 6 in a concentration dependent manner and about 90% inhibition in prostaglandin release was observed at 30 μM dose of Compound 6. This data indicated that Compound 6 is able to inhibit prostaglandin E$_2$ release in UVB light-stimulated epidermal cells.

Figure 15:
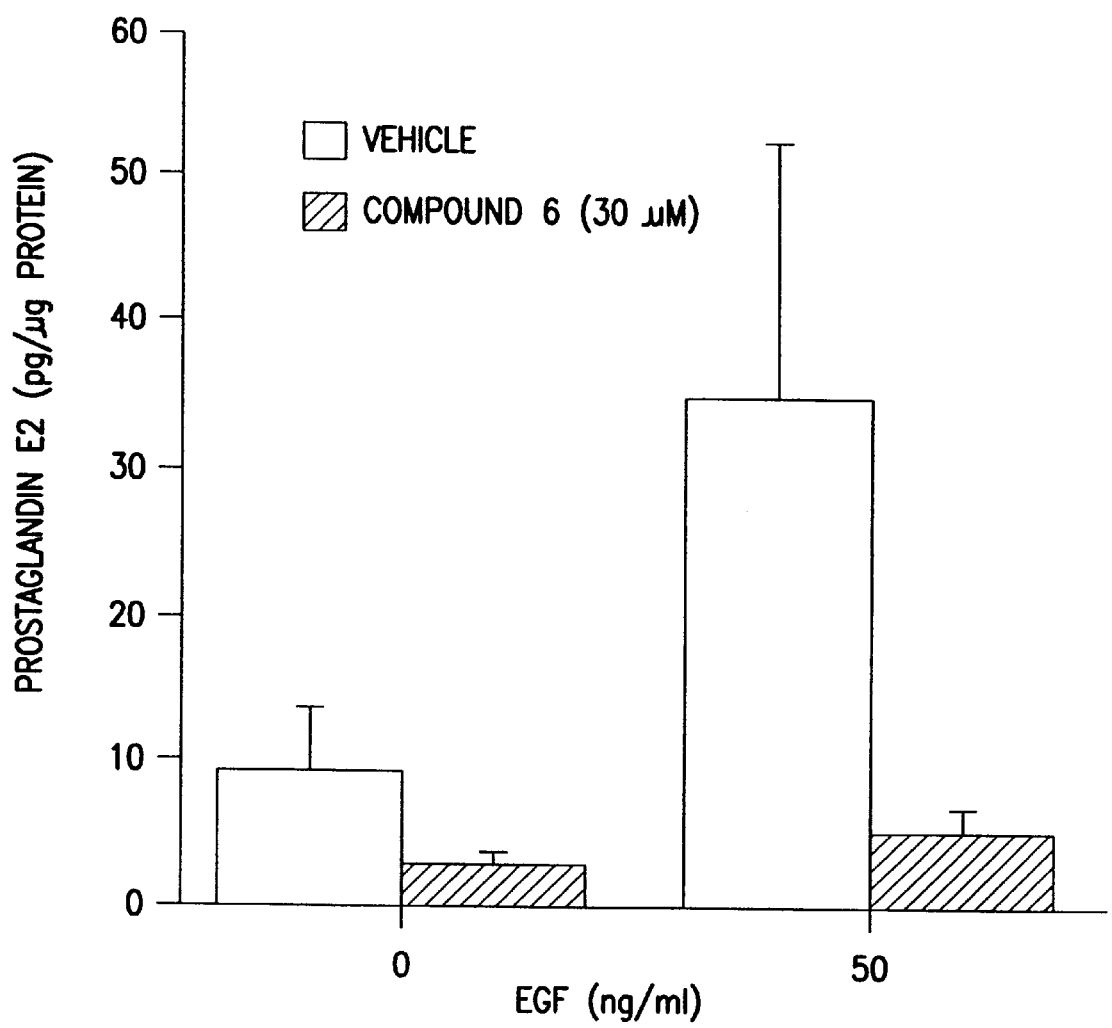
FIG. 15. Compound 6 inhibits EGF-stimulated PGE$_2$ release in epidermal cells. 50 ng/ml EGF was used to stimulate confluent HaCaT cell cultures both in the absence and presence of compound 6 and the cells were incubated for 6 h at 37 (C. Following incubation the supernatant was collected, and PGE$_2$ released during incubation was determined by EIA. Data represent mean ( SEM (n=5).

Primary human keratinocytes as well as HaCaTs express significantly high number of functional EGF-receptors on their cell surface (). Upon stimulation the EGF-receptors present on the epidermal cells participate in transmembrane signaling and induce the formation of prostaglandins. To determine that the previously observed inhibition in prostaglandin release by Compound 6 was due to the inhibition of EGF-R activation, we studied the effect of Compound 6 on EGF-stimulated prostaglandin formation in epidermal cells. Stimulation of the HaCaT cells with 50 ng/ml rhEGF for 6 h induced about 4 fold increase in prostaglandin release over unstimulated control, (FIG. 15) and the observed increase in prostaglandin release was inhibited in the presence of 30 μM Compound 6, indicating that (i) epidermal growth factor receptors mediate prostaglandin formation in epidermal cells, and (ii) Compound 6 inhibits the prostaglandin release in UVB light stimulated cells through the inhibition of EGF-R activation.

Morphology and Skin edema measurement. Morphological appearance of the UVB irradiated skin was monitored visually and compared with the control mice skin. Skinfold thickness of the dorsal surface of the mice was recorded before, and everyday after UVB exposure for five days with a digital thickness gauge (Mitutoyo, So. Plainfield, N.J.) which measures thickness in 0–10 mm range with an accuracy of 0.015 mm.

Figure 16:
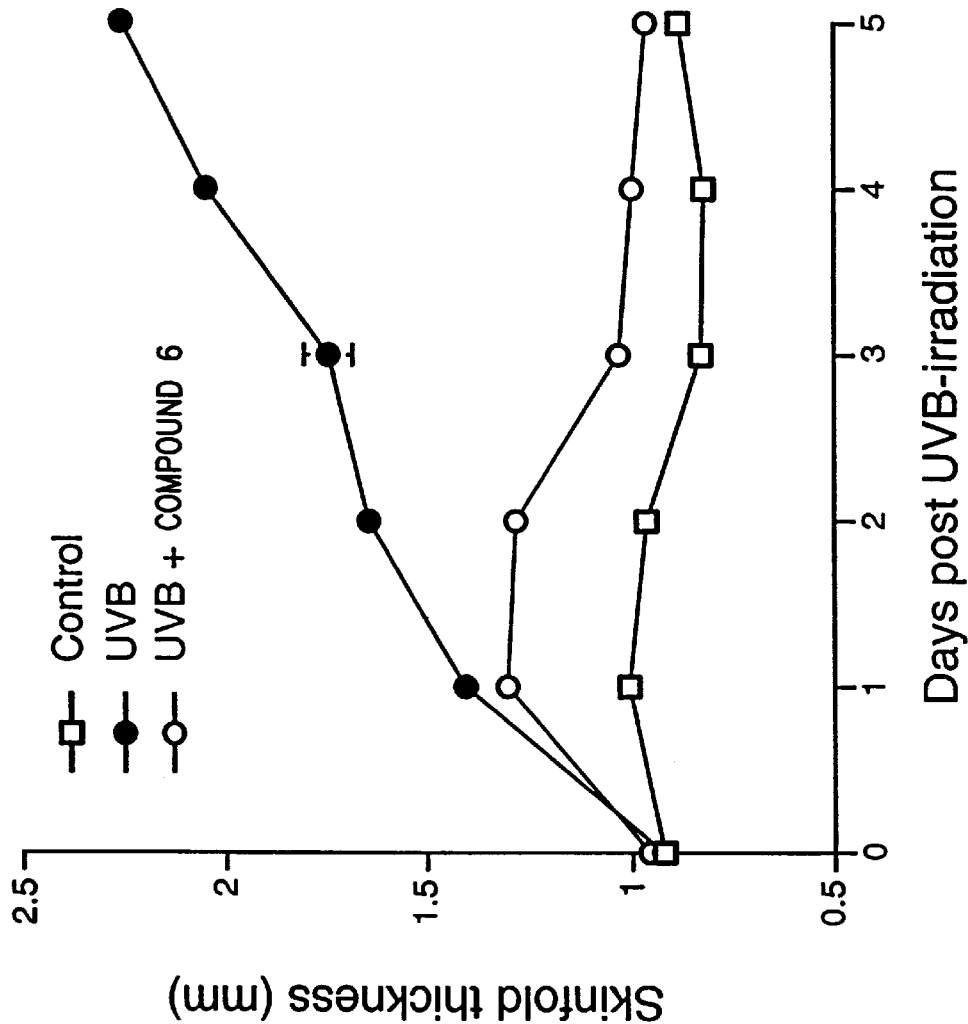
FIG. 16. Effect of Compound 6 on skinfold thickness of skh-1 mice following UVB light injury. Skh-1 mice were pretreated with compound 6 (16 mg/kg; i.p. bolus injection) for 2 days. On the day of UVB irradiation the mice were anaesthetized and painted with 1.5 mg/cm$^2$ compound 6 on dorsal surface 15 minutes before UVB exposure, and irradiated with UVB light (250 mj/cm$^2$). The skinfold thickness was measured on day 1 through 5 post-irradiation. The data are expressed as mean (SEM (n=5–34).

As mentioned earlier, Prostaglandin E$_2$ is a potent inflammatory mediator and is well known to induce vasodilation and potentate edema in skin following injury. Since our in vitro study using epidermal cells showed that compound Compound 6 inhibits the release of PGE$_2$ in UVB stimulated cells, we were interested to determine if Compound 6 is able to inhibit the harmful inflammatory responses of skin following UVB light exposure in vivo. For these studies we used female, hairless, albino skh-1 mice and exposed their dorsal surface with 250 mj/cm$^2$UVB light. The skinfold thickness of the dorsal surface of the mice was determined as a measurement of skin edema from day 1 through day 5 following irradiation. FIG. 16 shows that a single exposure of mice to 250 mj/cm$^2$ UVB induced a time dependent increase in skinfold thickness. Compound 6 was not able to effectively inhibit the skin edema at 24 h post irradiation. However, it blocked further increase in skin thickness by 48 h post-UVB exposure in irradiated group of mice. In contrast, the skin thickness increased to about 70% of the control mice skin thickness at the same time point. At 72 h post irradiation, a significant decrease in skin edema was observed in Compound 6 treated mice and by day five post irradiation, the skinfold thickness in drug treated mice was almost back to control level. In contrast, in vehicle treated group the skin thickness increased to a total of 2.5 fold of control mice skin thickness over five day period. Similar results were obtained with P131 dissolved in polyethylene glycol-200 (PEG-200) (data not shown). These observations indicated that Compound 6 is able to inhibit UVB light-induced skin edema in mice.

Figure 18A:
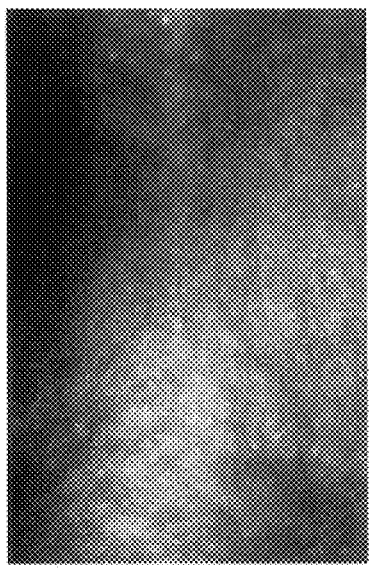
FIG. 18. Effect of compound 6 on skin morphology at day 4 post UVB-irradiation. Skh-1 mice were pretreated with compound 6 (16 mg/kg; i.p. bolus injection) for 2 days, painted with 1.5 mg/cm$^2$ compound 6 on dorsal surface 15 minutes before UVB exposure, and irradiated with UVB light (250 mj/cm$^2$). On day 4 mice were anaesthetized and a picture of their dorsal surface was taken. Magnification 2×.
Figure 18B:
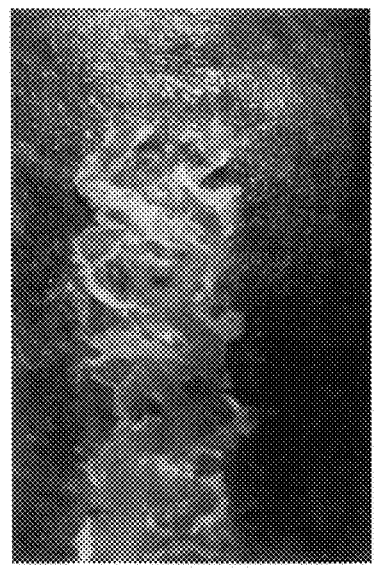
Figure 18C:
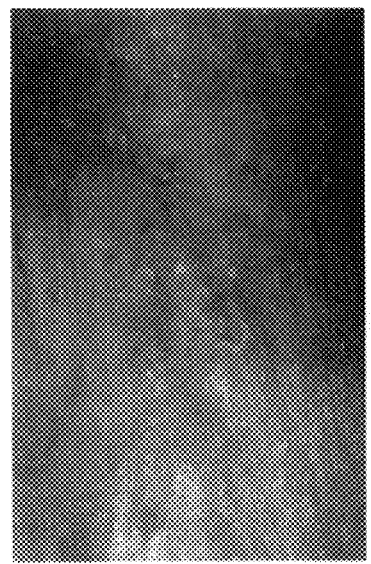

We also monitored the morphological changes in skin appearance following UVB light exposure in Compound 6 treated and vehicle treated groups of mice. Sunburn damage to the skin in first 24–48 h following UVB exposure was visible as an "elephant skin" appearance of the skin surface. The UVB light irradiated skin of mice appeared pink in color, leathery and thick. On day 1 and day 2 following the induction of inflammation, no significant difference was noted in skin appearance of drug treated and vehicle treated groups of mice. However, in UVB irradiated, vehicle treated mice, starting at day 3 many flakes of desquamating skin could be seen peeling off the skin surface and by day 5 the skin of this group of mice had become tough, leathery, and had developed scars on the surface. In contrast, in Compound 6 treated group, the skin appearance of mice improved following day 3 and by day 5 post-UVB, the signs of skin inflammation had diminished and the skin appearance resembled to that of control group mice (FIG. 18).

Figure 19A:
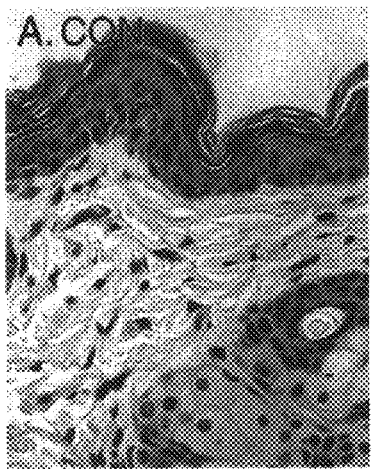
FIG. 19. Inhibition of UVB-induced histological changes in skin of skh-1 mice by compound 6. Mice were treated with drug and exposed to UVB (250 mj/cm$^2$) following the same procedure as described in Figure legend 3. At 48 h post-irradiation mice were sacrificed, skin was biopsied and paraffin sections of the tissue were stained with hematoxylin and eosin. (a) control, (b) UVB (250 mj/cm$^2$), and (c) COMPOUND 6+UVB (250 mj/cm$^2$). Magnification 40×.
Figure 19B:
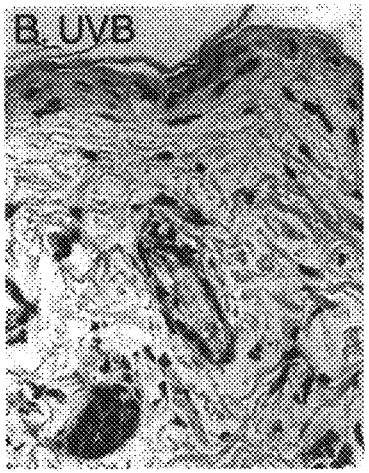
Figure 19C:
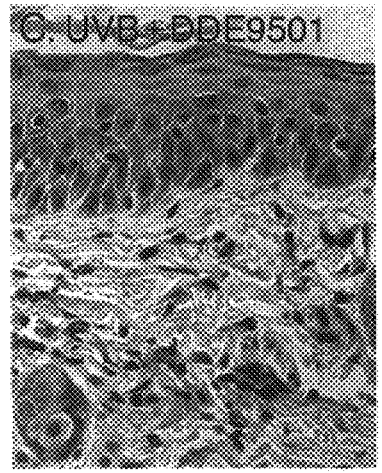

UVB light-induced histological changes of the skin were also studied. The normal epidermis typically has a 2–3 cell layer and contains scattered inflammatory cells especially around hair follicles (FIG. 19A). The UVB-irradiated skin showed thickened epidermis with 3–5 cell layers. Large number of neutrophils were also accumulated in the dermis (FIG. 19B). In contrast, the skin of mice treated with Compound 6 looked very much like the skin of unirradiated controls (FIG. 19C), with 1–2 cell layers of epidermis and normal dermis. Thus, Compound 6 prevented development of edema and neutrophil influx in UVB irradiated skin of mice.

Vascular permeability. Vascular permeability was quantitatively assayed by leakage from vessels of an albumin bound anionic dye, Evans blue (Sigma, St. Louis, Mo.). Evans blue (1%, 200 (l/mouse) was injected via the tail vein, 4 h later the mice were killed and the dorsal irradiated skin was biopsied. From the biopsies the dye was extracted in formamide (Sigma, St. Louis, Mo.) by warming the samples at 80° C. for 2 h and the optical absorbance of the formamide was measured at 620 nm.

Figure 17:
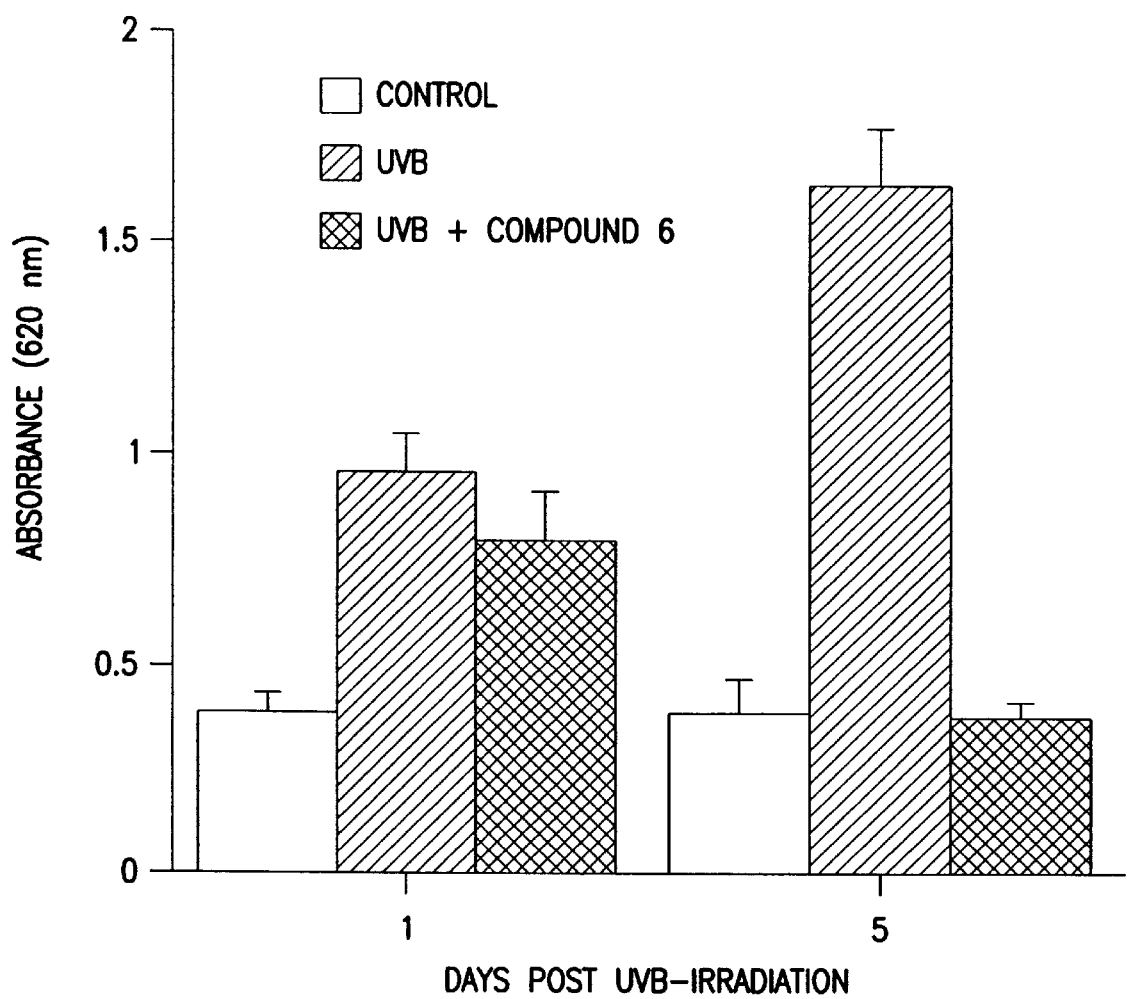
FIG. 17. Inhibition of UVB-induced plasma exudation in skin of skh-1 mice. Plasma exudation was evaluated at the times indicated after UVB exposure (250 mj/cm$^2$) by measuring the absorbence of Evans blue in skin extracts following the method described in Materials and Method. Data represent mean (SEM (n=5–17).

Since edema is associated with increased plasma exudation, we determined the effect of Compound 6 on UVB induced skin vascular permeability. The data on vascular permeability changes following the UVB irradiation has been presented in FIG. 17. Consistent with the skin edema findings there was an increase in vascular permeability of the skin in UVB irradiated mice. The effect of Compound 6 was minimal at 24 and 48 h post irradiation. However, at day 5 post-UVB, in Compound 6 treated group the vascular permeability was back to control level whereas a five fold increase in vascular permeability was observed in UVB exposed, vehicle treated group of mice.

Sun burn cell staining and histological studies. After the mice were killed by cervical dislocation, the skin was removed and spread on a sheet of dental wax. One punch (8 mm) was taken and fixed in buffered formalin. 4–5 $\mu$m thick sections were cut from paraffin blocks. Sunburn cell staining was done using ApopTag Plus In situ Detection kit (Oncor, Gaithersburg, Md.) which detects sunburn cells by direct fluorescence of digoxigenin-labelled genomic DNA. Briefly, the residues of digoxigenin-nucleotides were catalytically added to 3'—OH ends of double or single stranded DNA in presence of terminal deoxynucleotidyl transferase enzyme and the bound nucleotides were detected using anti-digoxigenin antibody conjugated with fluorescein.

To study the histological changes following irradiation the tissue sections were stained with hematoxylin and eosin and the stained slides were examined microscopically.

Figure 20A:
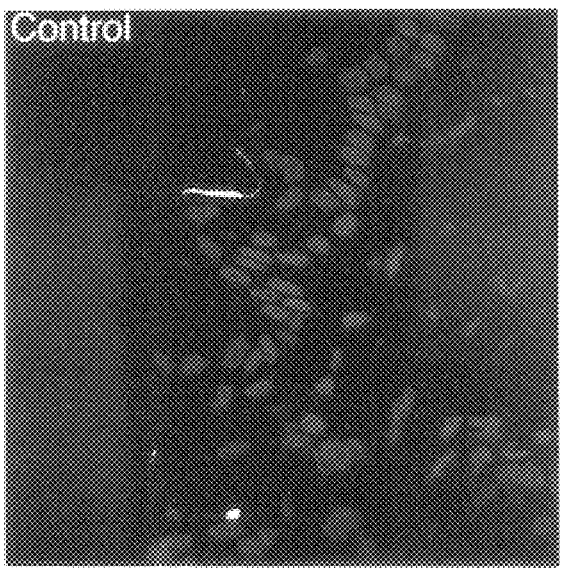
FIG. 20. Apoptosis of epidermal cells in UVB irradiated skin in skh-1 mice and its inhibition by compound 6. Skin biopsies from the irradiated and sham irradiated mice with or without drug treatment were taken out at 48 h post UVB-irradiation and paraffin sections obtained were stained for apoptotic cells. The figure shows images captured by confocal microscope using 60× magnification. Green stain in the picture shows apoptotic cells.
Figure 20B:
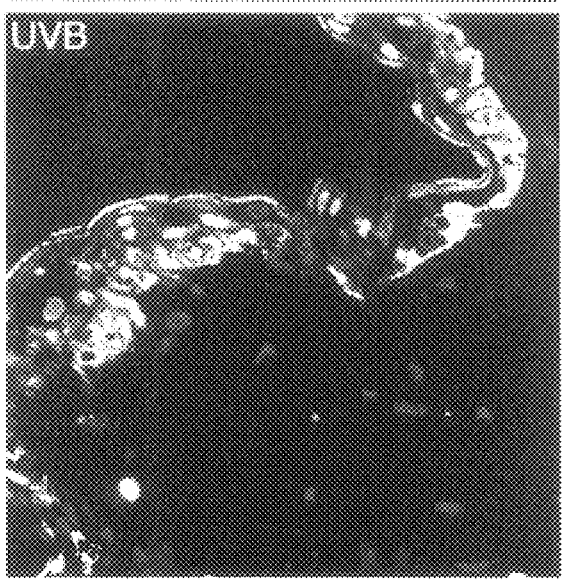
Figure 20C:
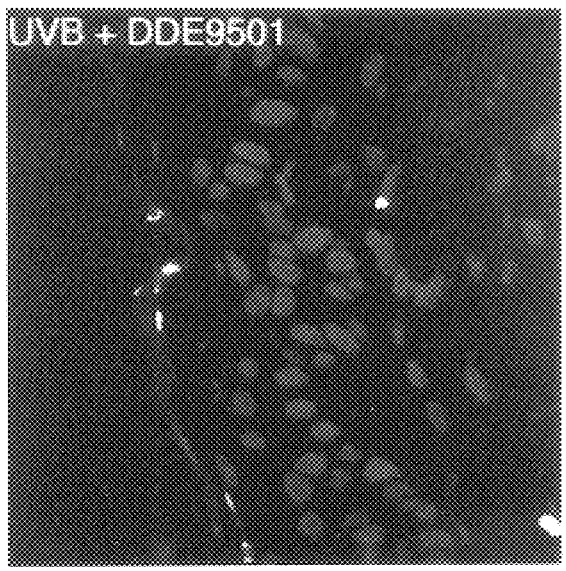

An acute exposure to UVB light induces sunburn in skin cells. The presence of sunburn cells in UVB-irradiated mice skin was detected using In Situ apoptosis detection kit as stated earlier. A significant number of sunburnt cells (FIG. 20) were observed in the skin of UVB-irradiated mice at 48 h after light exposure. In contrast, in Compound 6 treated mice significantly less or no sunburnt cells were observed at the same time point. Thus, the data suggest that Compound 6 inhibits the UVB induced cell death in mouse skin.

The ability of a compound to prevent or treat transplant complications can be determined using assays that are known in the art, or can be determined using assays similar to those described in Example 6.

Example 6

Transplant Complications

Proliferation assays. Splenocytes ($4 \times 10^5$/100 $\mu$l) from 9-wk-old C57BL6 males were used as responders in phytohemagglutinin (PHA)- and concanavalin A (Con A)-induced proliferation assays. The cells were applied in triplicates per group to a 96-well microplate in a final volume of 200 $\mu$l of RPMI 1640 medium, supplemented by 10% fetal calf serum. PHA or Con A (Sigma, St. Louis, Mo.) were added in the concentration of 5 or 2 $\mu$g/ml, respectively. Compound 6 was added in the concentration of 0.1, 1, 10 and 50 $\mu$g/ml. Cells were cultured in 5% CO2 with humidified air in an incubator at 37° C. for 3 days. Then, a colorimetric assay for the quantification of cell proliferation, based on the cleavage of the tetrazolium salt WST-1 by mitochondrial dehydrogenases in viable cells (Boehringer Mannheim, Indianapolis, Ind.), was performed following manufacturer's instructions. The absorbance was measured at 450/690 nm on a Multiskan MS microplate scanner. The value of cell proliferation was obtained by diminishing O.D. value of PHA- or Con A-stimulated cell proliferation by O.D. value of non-stimulated cells (negative control).

Mixed lymphocyte reaction (MLR). For MLR assay, responder cells (splenocytes obtained from 9-wk-old C57BL6 males) were plated in triplicates in 96-well-plates in the concentration of $4 \times 10^5$/100 $\mu$l and mitomycin-treated stimulators (splenocytes obtained from 10–12-wk-old BALB/c males) were added in the concentration of $8 \times 10^4$ in 50 $\mu$l. Compound 6 was added in the concentrations descried above to a final volume of 200 $\mu$l. Cells were cultured for 5 days and a calorimetric WST-1 assay was performed, as described above.

Apoptosis detection. C57BL6 splenocytes ($3 \times 10^6$/ml) were cultured in 24-well plate for 24 h in 500 $\mu$l of RPMI 1640 under the conditions described above. Compound 6 was added in the concentrations of 0.1, 1, 10 and 100 $\mu$g/ml. Apoptotic cell death was detected by TUNEL, using InSitu Cell Detection Kit, Fluorescein (Boehringer Mannheim, Indianapolis, Ind.). After the culture period, cells were washed, fixed, permeabilised and stained following manufacturer's instructions and apoptosis was analyzed by flow cytometry, using FACS Calibur (Becton Dickinson, San Jose, Calif.).

Mice. Bone marrow transplant recipients were 8–10 week old C57BL/6 ($H-2^b$) male mice and donors were 6–8 week old BALB/c ($H-2^d$) males (both strains purchased at Taconic, Germantown, N.Y.). Mice were kept in Animal care facility at The Hughes Institute, under the specific-pathogen-free condition (SPF). Free access to standard mouse diet (Harlan Teklad LM-485) and water was allowed. Recipients were given antibiotic-supplemented water (sulfamethoxazolel trimethoprim, Hi-Tech Pharmacal, Amityville, N.Y.) starting the day before transplantation.

Irradiation. Recipient mice, positioned in a pie shaped Lucite holder, were treated one day prior to bone marrow transplantation with a lethal dose (7.5 Gy) of Cesium (JL Sheppard Labs, 47.08 rad/min).

Bone marrow transplantation (BMT). Donor BALB/c bone marrow was collected into RPMI 1640 with L-glutamine (Cellgro) (Mediatech, Hendon, Va.) by flushing the shafts of the femur and tibia. At the same time, donor single cell suspension of splenocytes, eliminated from red blood cells by lysis buffer (ACK lysis buffer—0.15M $NH_4Cl$, 1.0M $KHCO_3$, 0.01M$Na_2$EDTA) was prepared, as well. BM cells were suspended by agitation with a pasteur pipette and separated from debris by passing through a fine pore nylon cell strainer. Red blood cells were eliminated by lysis buffer and clumps of debris were allowed to settle out. The cells were washed and were resuspended for i.v. injection via the caudal vein. The standard inoculum consisted of $25 \times 10^6$ BM cells and $25 \times 10^6$ splenocytes in 0.5 ml of RPMI 1640).

Graft-versus-host disease (GVHD) monitoring. BMT recipeints were monitored daily for the onset of clinical evidence of GVHD (determined by weight loss, manifestations of skin erythema, allopecia, hunching, diarrhea) and survival during the 90-day observation period. Survival times were measured from the day of BMT (day 0). Deaths occurring within 11 days of transplantation were considered to be radiation-induced and were excluded.

Drug Treatments. For GVHD prophylaxis—daily intraperitoneal (i.p.) injections of Compound 6 (WHI-P131), 4-(3'-hydroxyl-phenyl)-amino-6,7-dimethoxyquinazoline (WHI-P132, Compound 7), Cyclosporine (Sandimmune® Sandoz Pharmaceuticals Ltd, Basle, Switzerland), Methylprednisolone (Depo-Medrol® Pharmacia & Upjohn Company, Kalamazoo, Mich.), Methotrexate (Immunex Corporation, Seattle, Wash.) and vehicle control were administered to mice starting the day before BMT (−1) or on the day of BMT (day 0). Compound 6 was administered in a dose of 25 mg/kg/day and 60 mg/kg/day (divided in three doses), Compound 7–50 mg/kg/day day (divided in three doses), from the day 0 of BMT; cyclosporine, methylprednisolone and methotrexate were injected in a doses according the Children cancer group (CCG) protocol: 3 mg/kg/day (divided in two doses), 10 mg/kg/day (divided in two doses) and 10 mg/m$^2$/day (once daily), respectively. The treatments with cyclosporine and methylprednisolone started the day before BMT (−1) and lasted till the end of experimental period, while methotrexate was administered on days 1, 3, 6 and 11 post BMT.

Statistical analysis. Statistical analysis of data obtained in proliferation assays, MLR and apoptosis data was done by Student's t-test, while survival data were analyzed by lifetable methods using the Mantel-Cox test.

Data from the above assays is presented in FIGS. 21–26

Figure 21A:
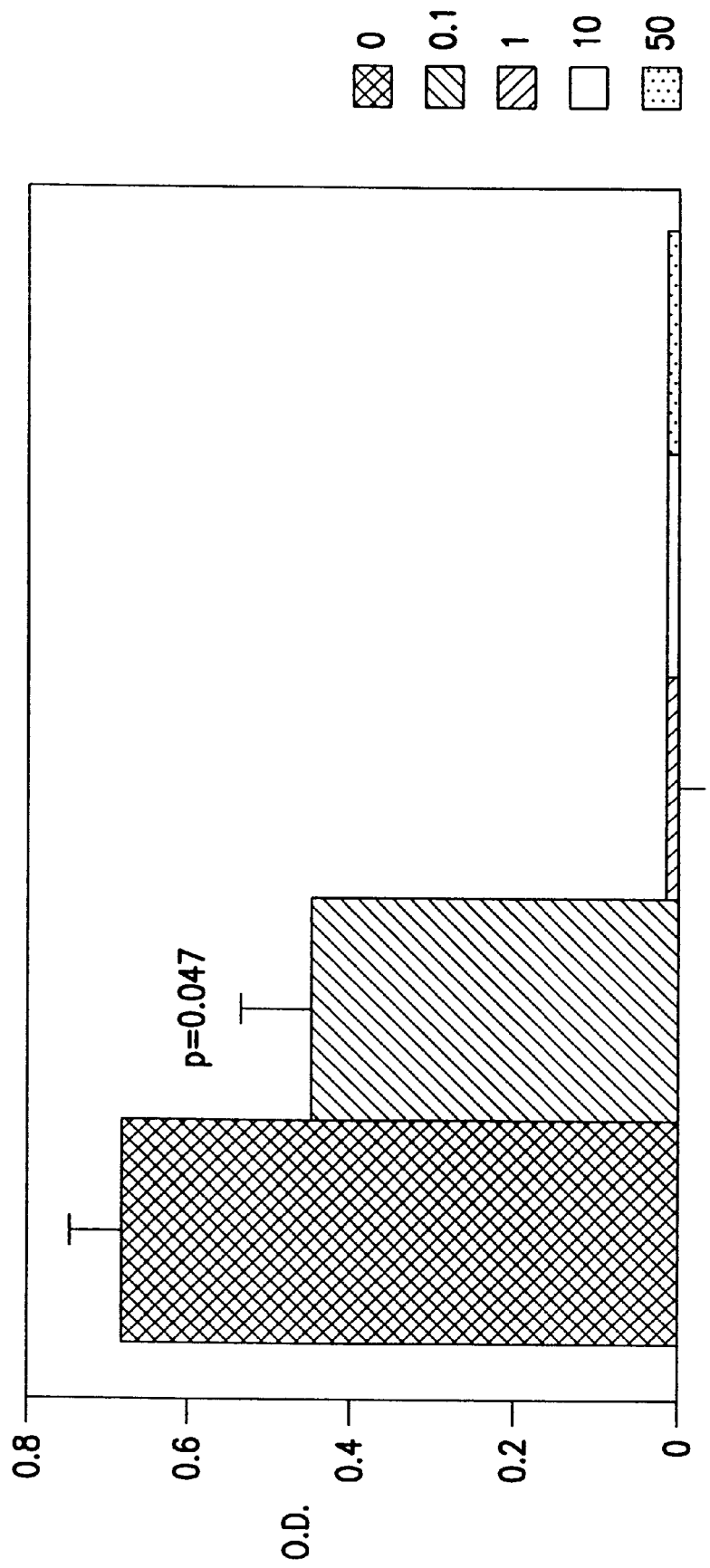
FIG. 21. Dose-dependent supression of MLR (A), PHA-induced (B) and ConA-induced (C) proliferation of splenocytes by WHI-P131. WHI-P131 was added in the concentration of 0.1, 1.0, 10, and 50 $\mu$g/mL during the 5-day culture (MLR). or 3-day culture period (PHA and ConA). Proliferation was measured by WST-1 colorimetric assar. Results are presented as mean O.D.±SEM of 3–7 separate experiments. Statistical differences between the groups analyzed by Student's t-test.
Figure 21B:
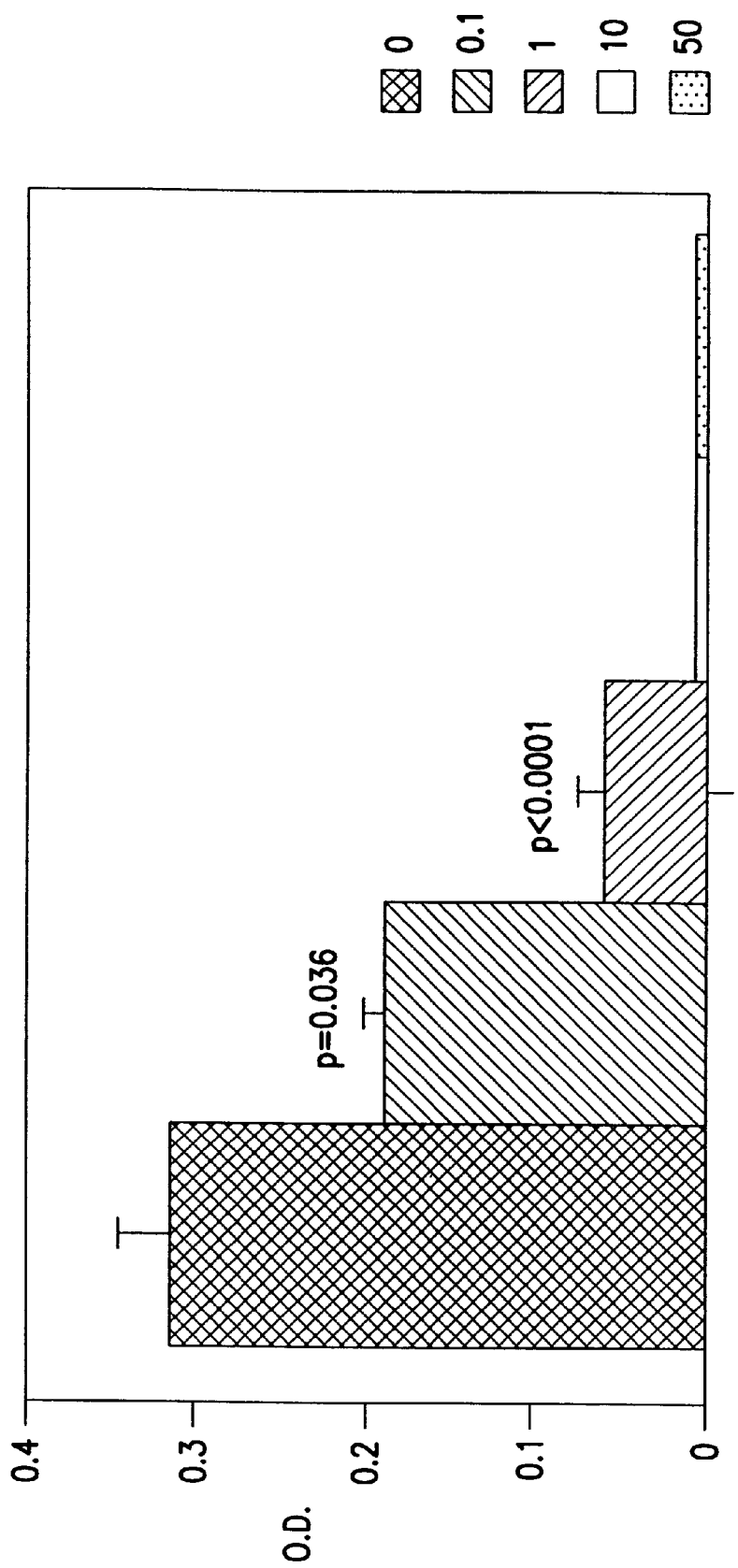
Figure 21C:
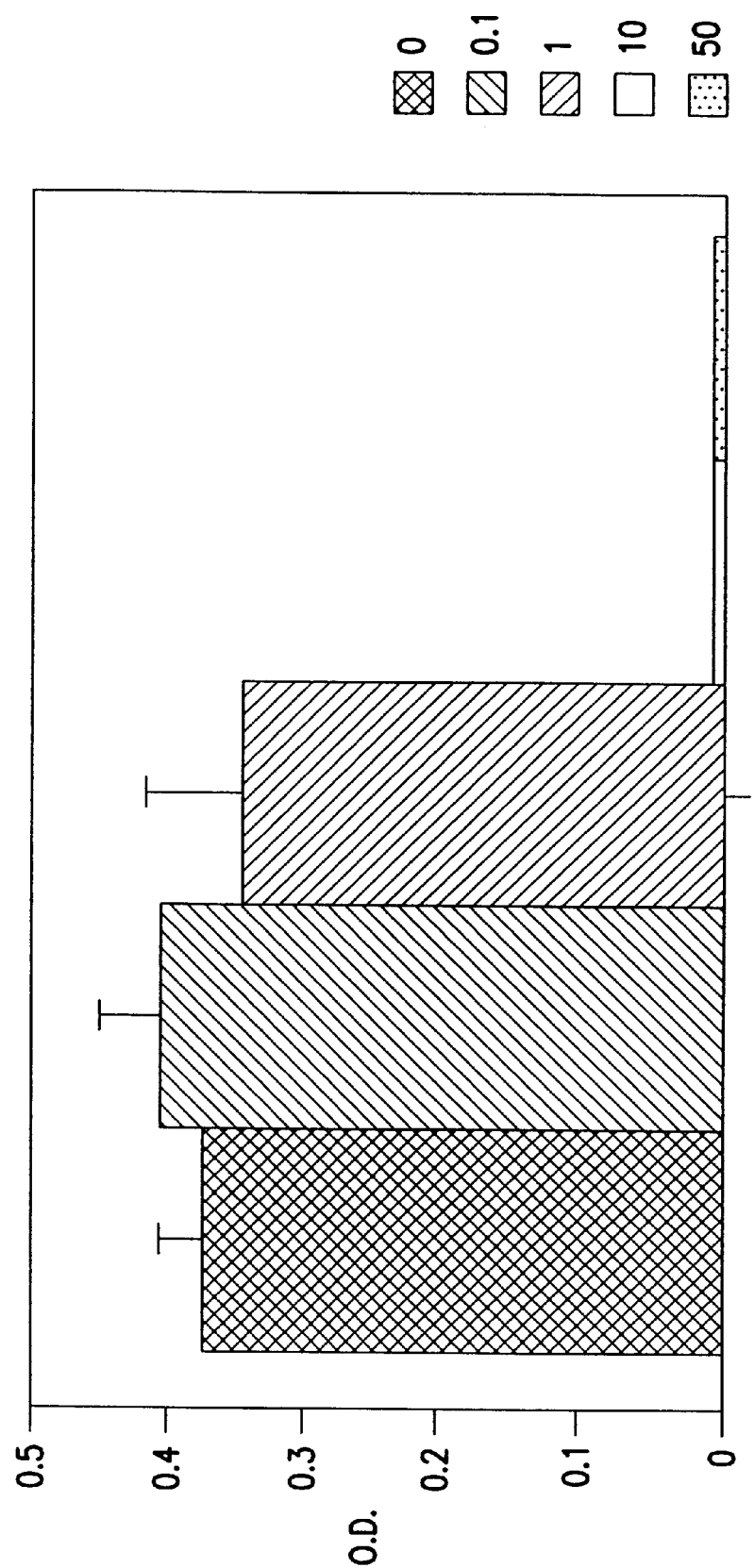
Figure 22:
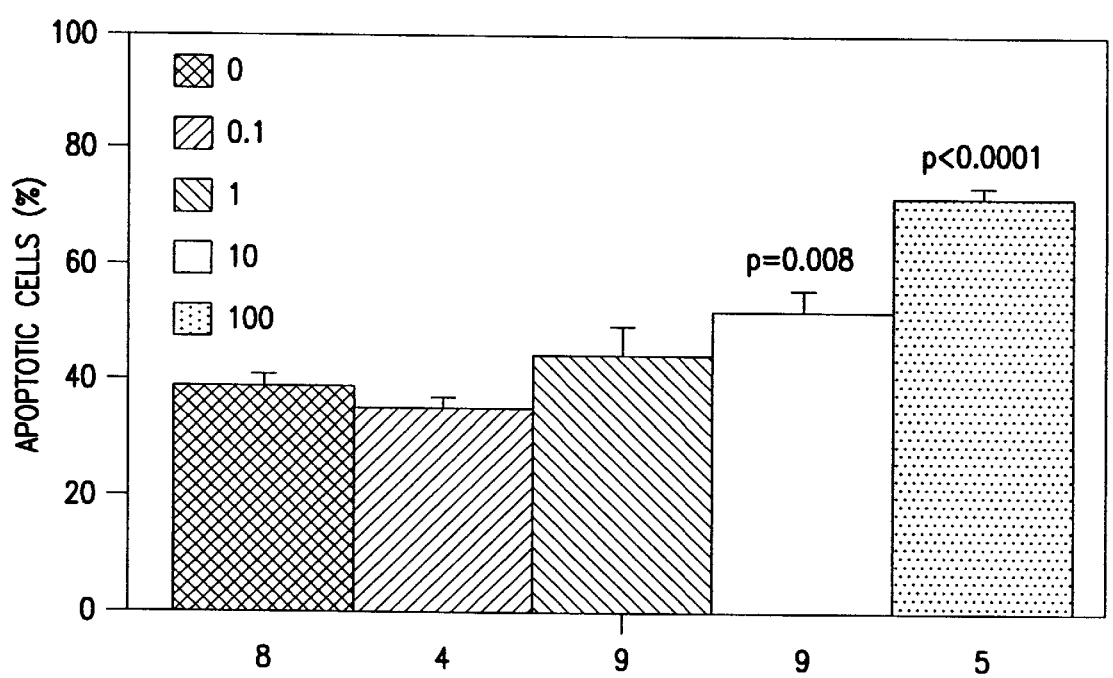
FIG. 22. Flow cytometry analysis of the percentage of apoptotic splenocytes (TUNEL-positive) obtained after the 24-h-culture period with addition of 0.1, 1, 10 and 100 $\mu$g/ml of WHI-P131. Results are presented as mean±SEM. Statistical differences between the groups analyzed by Student's t-test.
Figure 23:
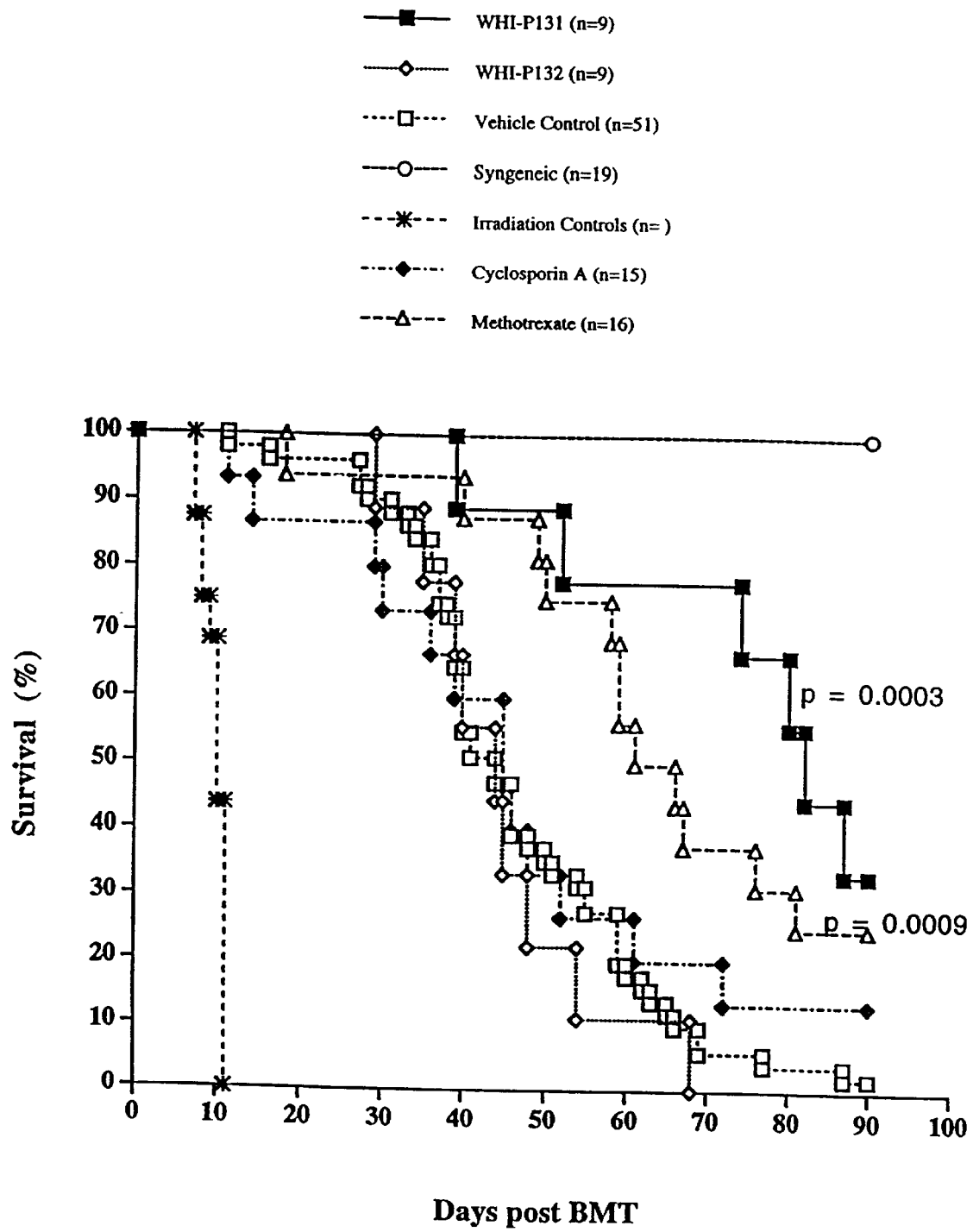
FIG. 23. The in vivo prophylactic effect of WHI-P131 administration on GVHD induced across the major histocompatibility barrier in C57BL6 (H-$2^b$) recipients with BALB/c (H-$2^d$) BM/splenocyte grafts. Irradiated (7.5 Gy) recipients were given BM and splenocytes ($25 \times 10^6$ of each). Some recipients received syngeneic BM, while others were treated daily with 25 mg/kg of WHI-P131, 50 mg/kg of WHI-P132, 3 mg/kg of Cyclosporine A, 10 mg/m$^2$ of Methotrexate or vehicle control, as described in Material and Method section. Differences in survival between the groups were analyzed by life-table analysis, Mantel-Cox test.
Figure 24:
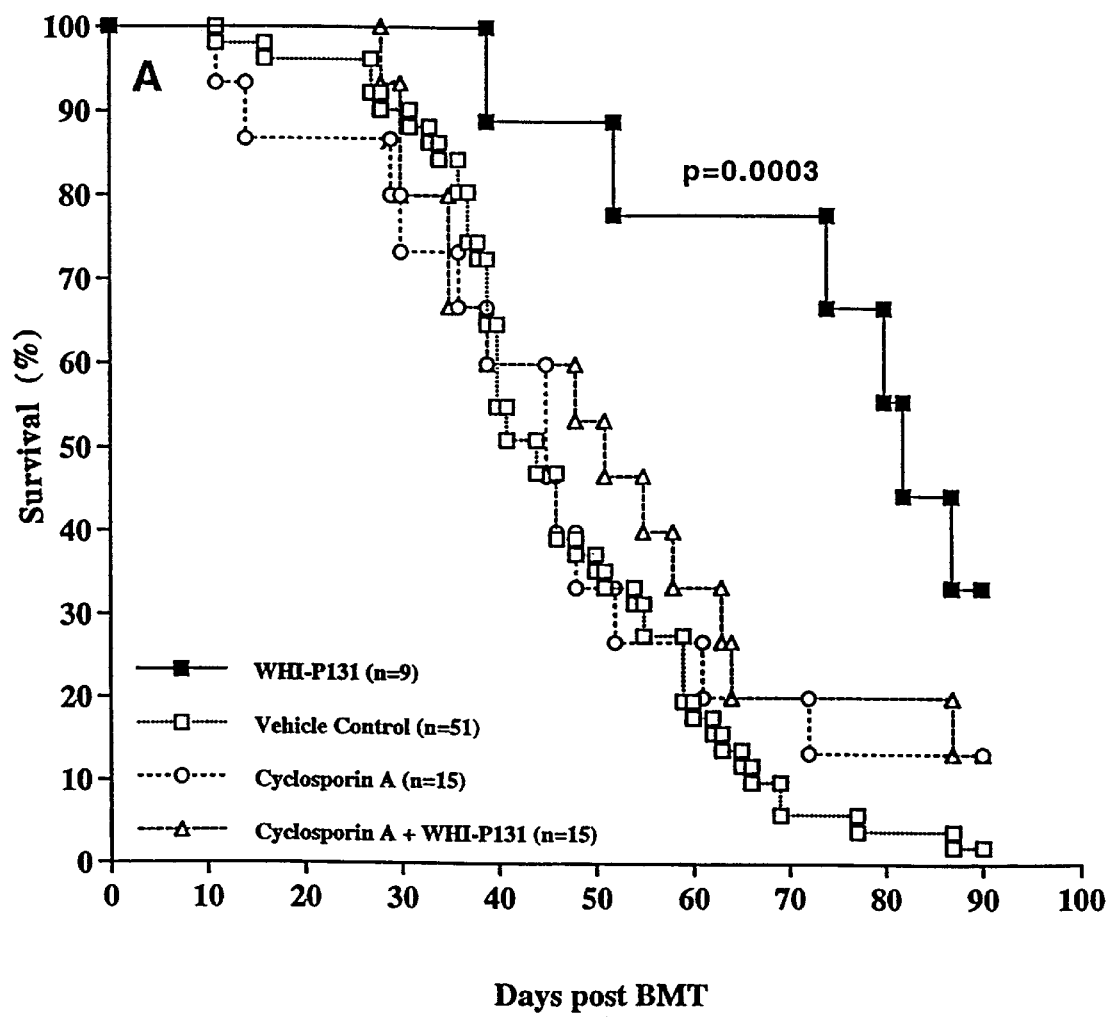
FIG. 24. The in vivo prophylactic effect of administration of drug combinations presented in FIG. 23 on GVHD induced across the major histocompatibility barrier in C57BL6 (H-$2^b$) recipients with BALB/c (H-$2^d$) BM/splenocyte grafts. WHI-P131 (25 mg/kg), cyclosporine A (3 mg/kg) or combination of cyclosporine A and WHI-P131 (A); were administered i.p. Differences-in survival between the groups were analyzed by life-table analysis, Mantel-Cox test.
Figure 25:
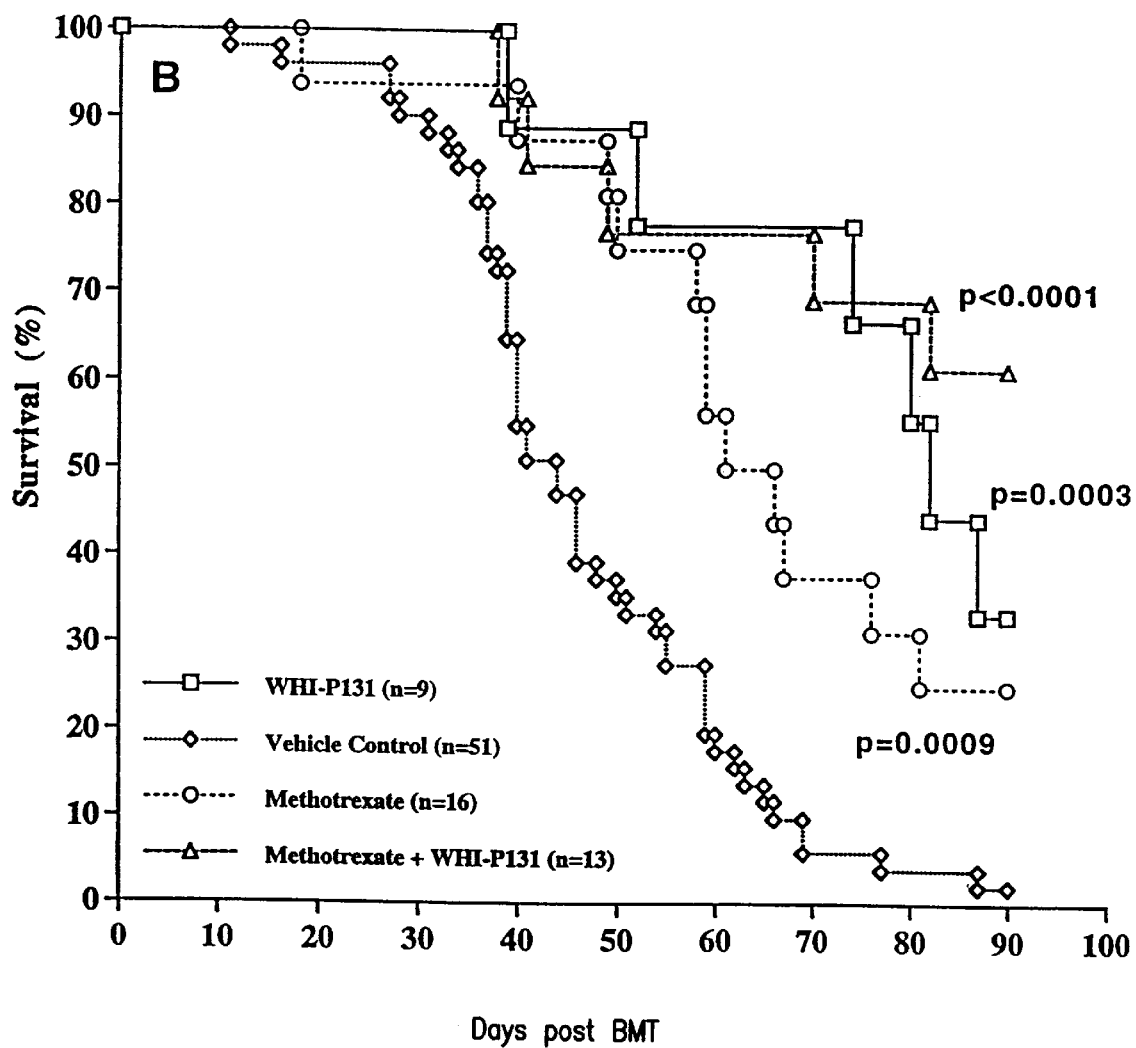
FIG. 25. The in vivo prophylactic effect of administration of drug combinations presented in FIG. 23 on GVHD induced across the major histocompatibility barrier in C57BL6 (H-$2^b$) recipients with BALB/c (H-$2^d$) BM/splenocyte grafts. WHI-P131 (25 mg/kg), and WHI-P131 and methotrexate (10 mg/m$^2$) or combination of methotrexate and WHI-P131 were administered i.p. Differences in survival between the groups were analyzed by life-table analysis, Mantel-Cox test.

FIG. 21. Dose-dependent suppression of MLR (A), PHA-induced (B) and ConA-induced (C) proliferation of splenocytes by WHI-P131. WHI-P131 was added in the concentration of 0.1, 1, 10 and 50 μg/ml during the 5-day-culture (MLR) or 3-day-culture period (PHA and ConA assays). Proliferation was measured by WST-1 colorimetric assay. Results are presented as mean O.D.±SEM of 3–7 separate experiments. Statistical differences between the groups analyzed by Student's t-test.

The ability of a compound to prevent or treat autoimmune diseases (e.g. autoimmune induced diabetes) be determined using assays that are known in the art, or can be determined using assays similar to those described in Example 7.

Example 7

Autoimmune Diseases

C57BL/6 and NOD mice were purchased from Taconic, Germantown, N.Y., and housed under pathogen-free conditions in Animal care facility of Hughes Institute. Jak 3$^{-/-}$ (C57BL/6×129/Sv) mice, homologous for disrupted Jak3 gene were generous gift of Dr. J. N. Ihle, St. Jude Children's Research Hospital, Memphis, Tenn. A homozygous Jak 3$^{-/-}$ mice were bred to C57BL/6 mice and the offspring of the F1 generation were backcrossed to C57BL/6 mice. After three generations of backcrossing to C57BL/6, the offspring were intercrossed to produce Jak 3$^{-/-}$ and wild-type (WT)Jak3$^{+/+}$ mice, which were used in our experiments.

Induction of LDSTZ model of diabetes. C57BL/6 male mice or JAK 3-deficient and WT mice (8–10-wk-old) were injected intraperitoneally with low-dose (40 mg/kg ) of STZ (Sigma, St Louis, Mo.) daily for 5 consecutive days, for induction of autoimmune experimental diabetes (LDSTZ). STZ was dissolved in citrate buffer pH 4.0 on ice, and injected within 10 min of preparation. Mice were monitored for diabetes development by testing blood glucose from the second week (day 7) after the STZ administrations by One Touch Profile diabetes tracking system (Lifescan, Milpitas, Calif.). Mice with glycemia over 220 mg/dl on three consecutive tests were considered diabetic, with the first detection of chronic glycemia taken as the date of diabetes onset. A group of C57BL/6 males was treated with WHI-P131 - 100 mg/kg/day, i.p., devided in two equal doses, from a beggining of the experiment till day 25. As WHI-P131 was solubilazed in 10% DMSO in PBS, control mice were treated with 10% DMSO in PBS, using the same conditions as described above.

Treatment of NOD females with WHI-P131 and assessment of diabetes development. NOD females were treated from 5- or 10-wk of age with different dose of WHI-P131, daily, i.p. Control mice were treated with 10% DMSO in PBS. Mice were monitored for diabetes development by testing blood glucose from 10 wk of age by One Touch Profile diabetes tracking system, as described above.

Intraperitoneal glucose tolerance test (IPGTT). Intraperitoneal glucose tolerance test (IPGTT) was performed in the group of non-diabetic WHI-P131-treated and vehicle-treated control NOD females on the end of experimental period (25 wk of age of NOD mice). Mice were fasted for 10 hours, and the glucose solution (1.5 g/kg body weight) was injected i.p. Before and after injection of glucose, blood samples were taken and blood glucose levels were measured (as described above) at 0, 30, 60 and 120 min time points.

Histology. The group of control and WHI-P131-treated non-diabetic NOD females was sacrificed at the end of experimental period, at 25 wks of age, and characteristic histopathologic lesion of islets (insulitis) was evaluated in each mouse scoring at least 25 islets per mouse. Briefly, pancreas was removed, fixed in 10% formalin, parafin embedded, cut and stained with hematoxylin and eosin for light microscopic examinations. All islets sampled from three nonoverlapping pancreatic levels were assigned an insulitis score as follows: 0—no visible lesions; 1—peri-insulitis with no islet penetration; 2—<25% of the islet infiltrated; 3—>25% of the islet infiltrated; 4—end stage.

Adoptive transfer of diabetic splenocytes to NOD-scid/scid females and assesment of diabetes development. Single-cell suspensions of splenic leucocytes pooled from 8–10 diabetic NOD females were prepared by passage through Nitex 110 mesh, and red blood cells were lysed in 10× Gey's solution. Aliquots of 1×10$^7$ splenocytes were adoptively transferred intravenously into 4-week-old NOD/Lt-scid/scid females (The Jackson Laboratory, Bar Harbor, Me.). WHI-P131 treatment (50 mg/kg) or control treatment (10% DMSO in PBS) of NOD-scid mice started at the same time. Mice were monitored for diabetes development by testing urinary glucose every week from second week after the transfer by Chemstrip uGK strips (Boehringer Mannheim, Indianapolis, Ind.). Mice with glycosuria over 500 mg/dl (+++) on consecutive weekly tests were considered diabetic, with the first detection of chronic glycosuria taken as the date of IDDM onset.

Statistical analysis. Statistical analysis was done by using unpaired Student's t-test (IPGTT and insulitis data) and ANOVA test (differences in glycemic level between the experimental groups). Experimental differences in IDDM incidence studies in WHI-P131-treated and control NOD and LDSTZ-treated mice or in adoptively transferred scid mice were assessed by the Kaplan-Meier life table analysis using Mantel-Cox test. The p value <0.05 was considered as statistically significant.

Results for Example 7

Figure 27:
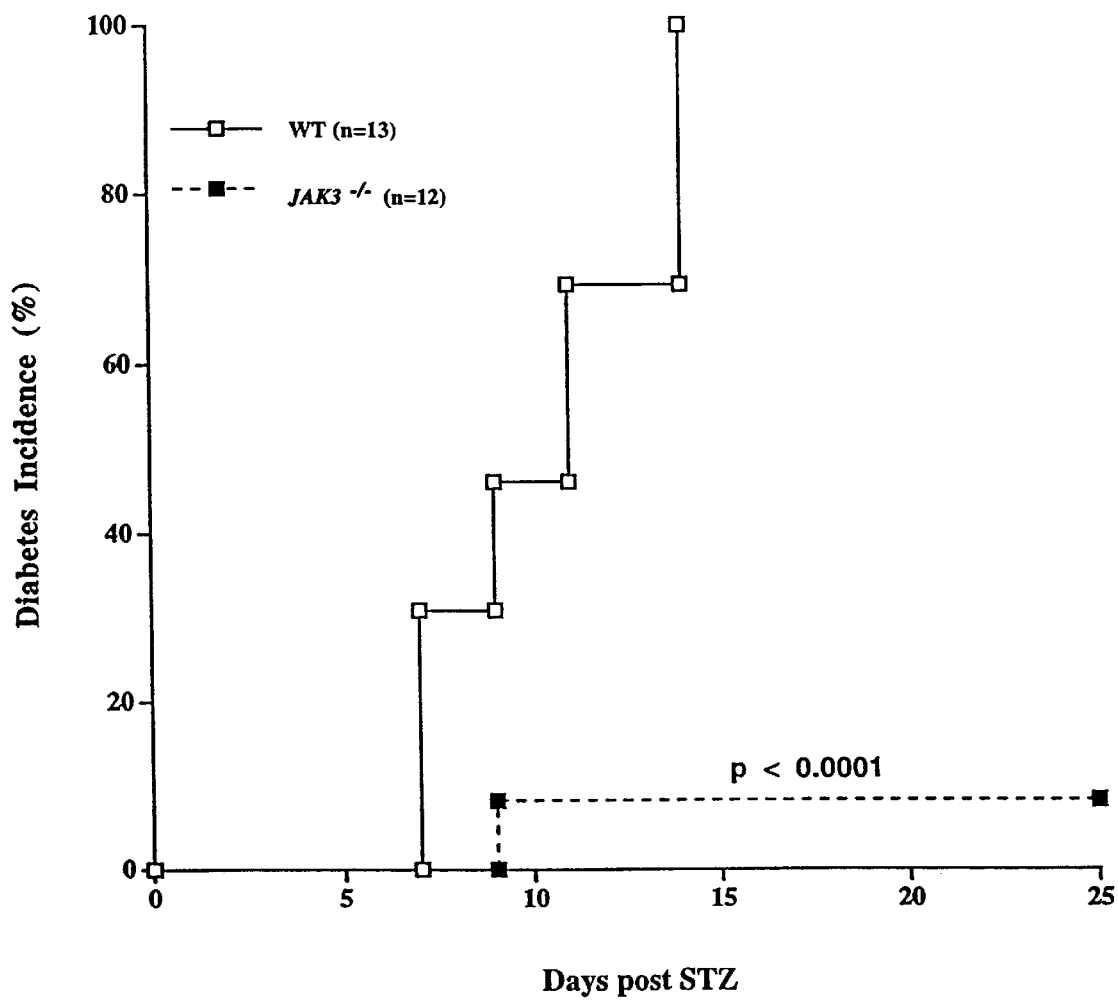
FIG. 27. Cummulative diabetes incidence (A) in LDSTZ-treatedJak3-deficient and wild-type (WT) males studied during the experimental period of 25 days post administration of first STZ injection; statistical difference obtained by life table analysis.
Figure 28:
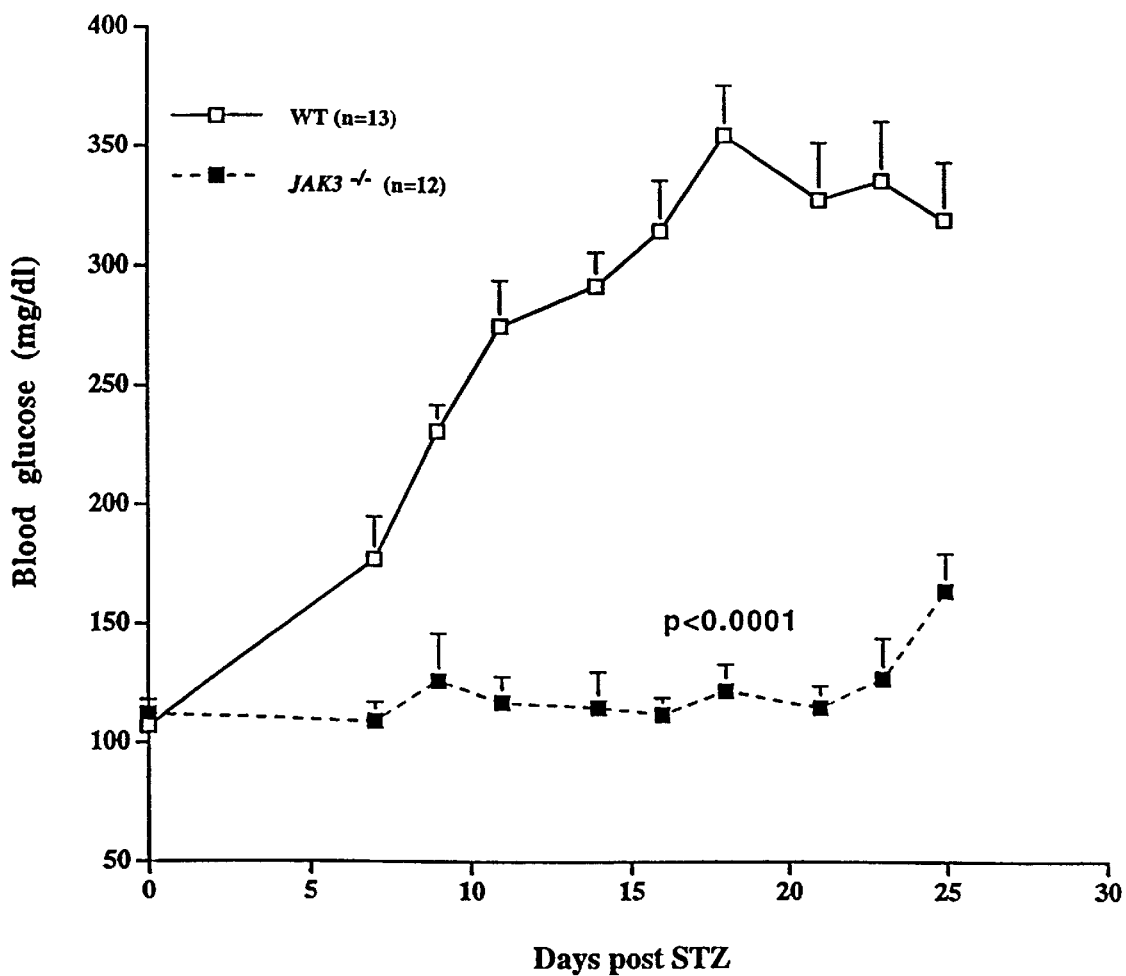
FIG. 28. Blood glucose level (mg/dl) (B) in LDSTZ-treatedJak3-deficient and wild-type (WT) males studied during the experimental period of 25 days post administration of first STZ injection; statistical difference obtained by ANOVA.

Development of LDSTZ diabetes is inhibited in JAK 3-deficient mice FIG. 27 shows cummulative diabetes incidence (A) and blood glucose level (B) in JAK3-deficient and WT mice treated by low-dose STZ. While 13/13 (100 %) of WT mice developed hyperglycemia till day 14 post first STZ injection, only 1/12 (8.3%) of JAK3-deficient mice became diabetic in entire experimental period of 25 days (p <0.0001) (FIG. 27). WT mice exhibited increase of blood glucose from day 7, reaching the hyperglycemic level (>220 mg/dl) on day 9 post first STZ injection (FIG. 28). In contrary, JAK 3-deficient mice stayed normoglycemic throught entire experimental period (p<0.0001 compared to WT glycemic level by ANOVA) (FIG. 28).

Figure 29:
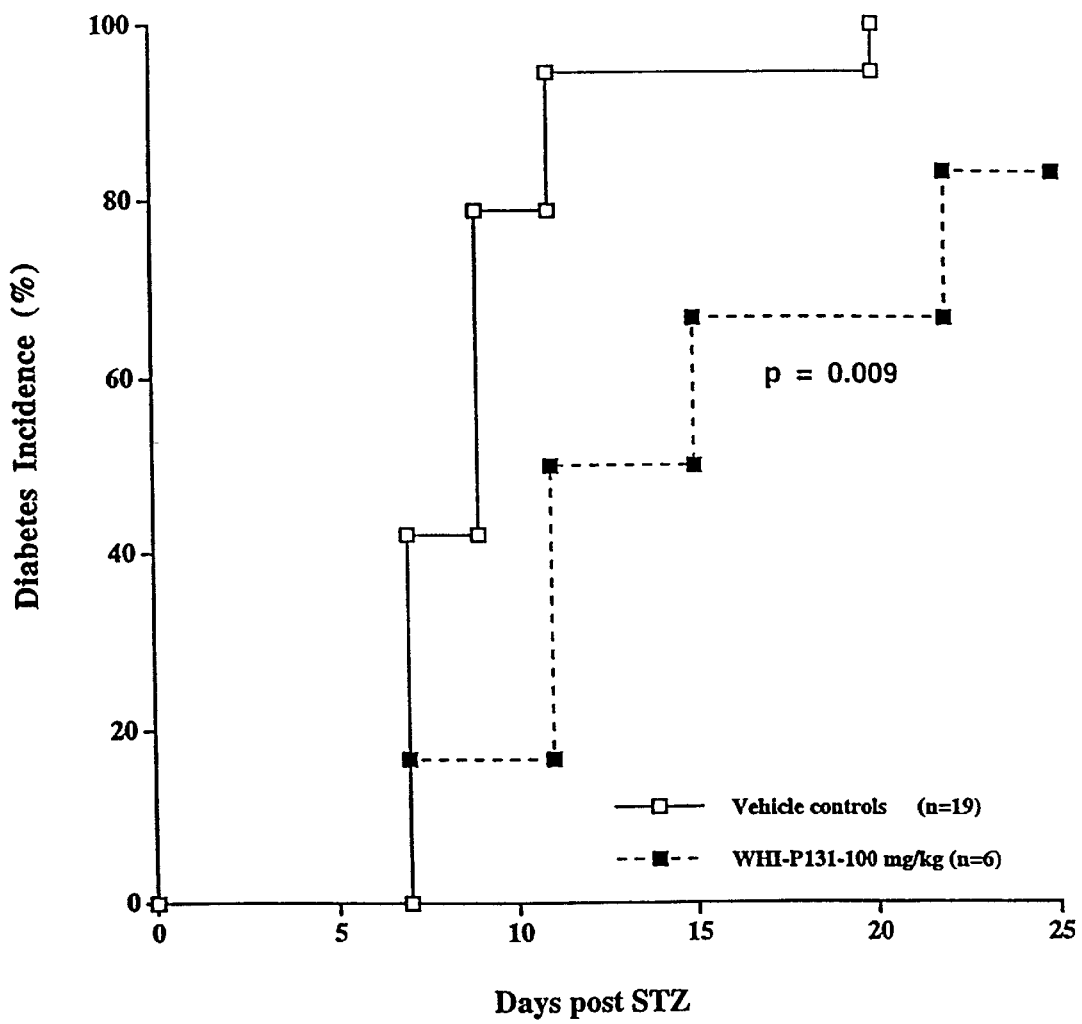
FIG. 29. Cummulative diabetes incidence (A) in LDSTZ-treated C57BL/6 males studied during the experimental period of 25 days post administration of first STZ injection; statistical difference obtained by life table analysis (Mantel-Cox test).
Figure 30:
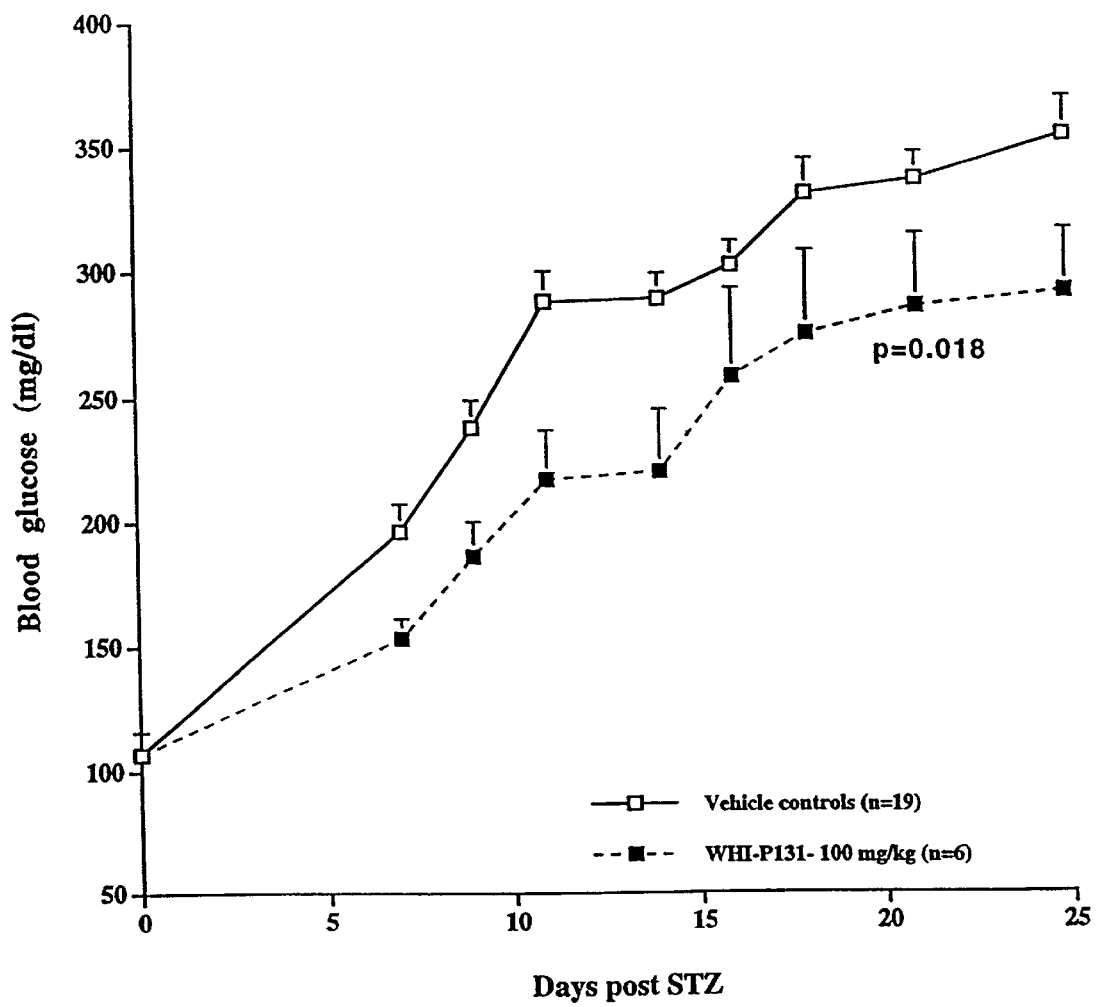
FIG. 30. Blood glucose level (mg/dl) in LDSTZ-treated C57BL/6 males studied during the experimental period of 25 days post administration of first STZ injection; statistical difference obtained by ANOVA.
Figure 31:
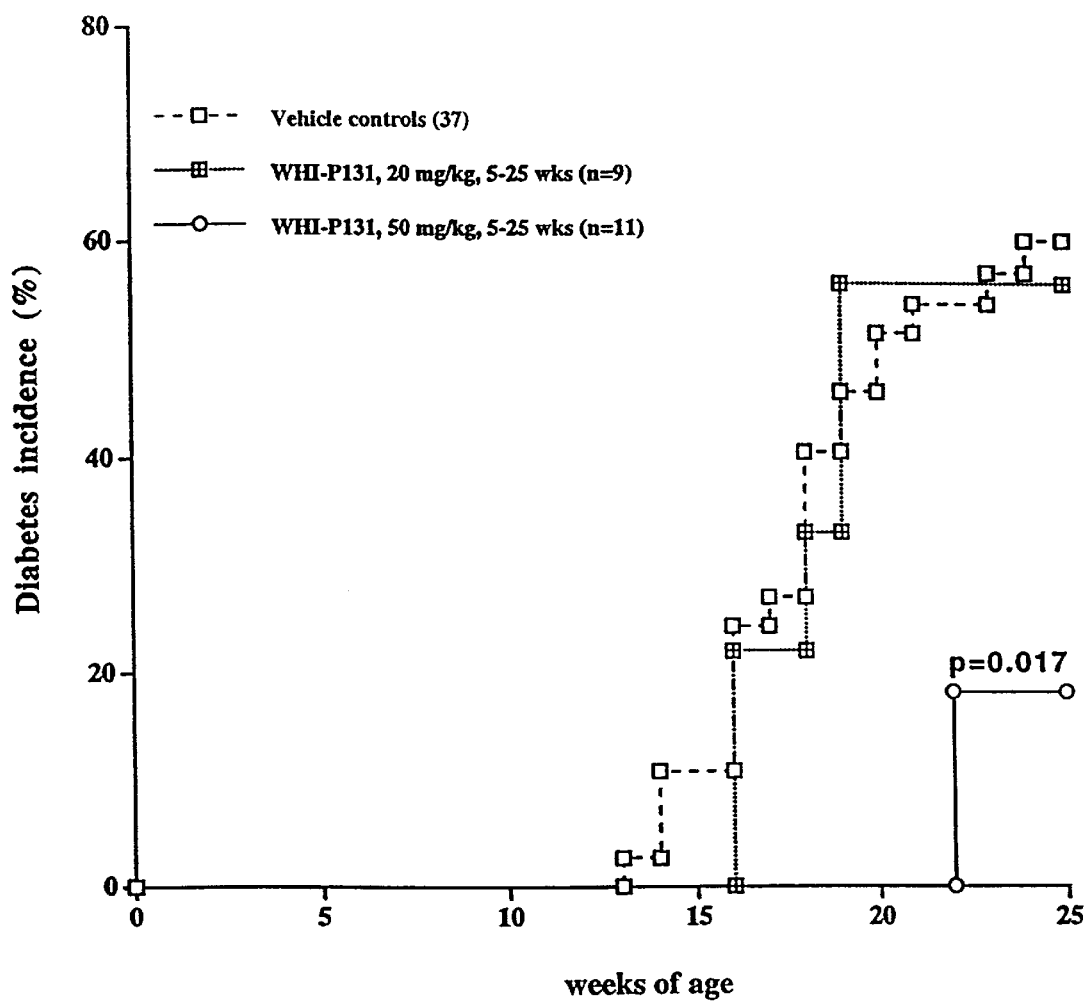
FIG. 31. Diabetes incidence in NOD females treated with 20 and 50 mg/kg of WHI-P131 daily from 5 to 25 wk of age (A) statistically significant differences between WHI-P131-treated and control mice were obtained by life table analysis (Mantel-Cox test).
Figure 32:
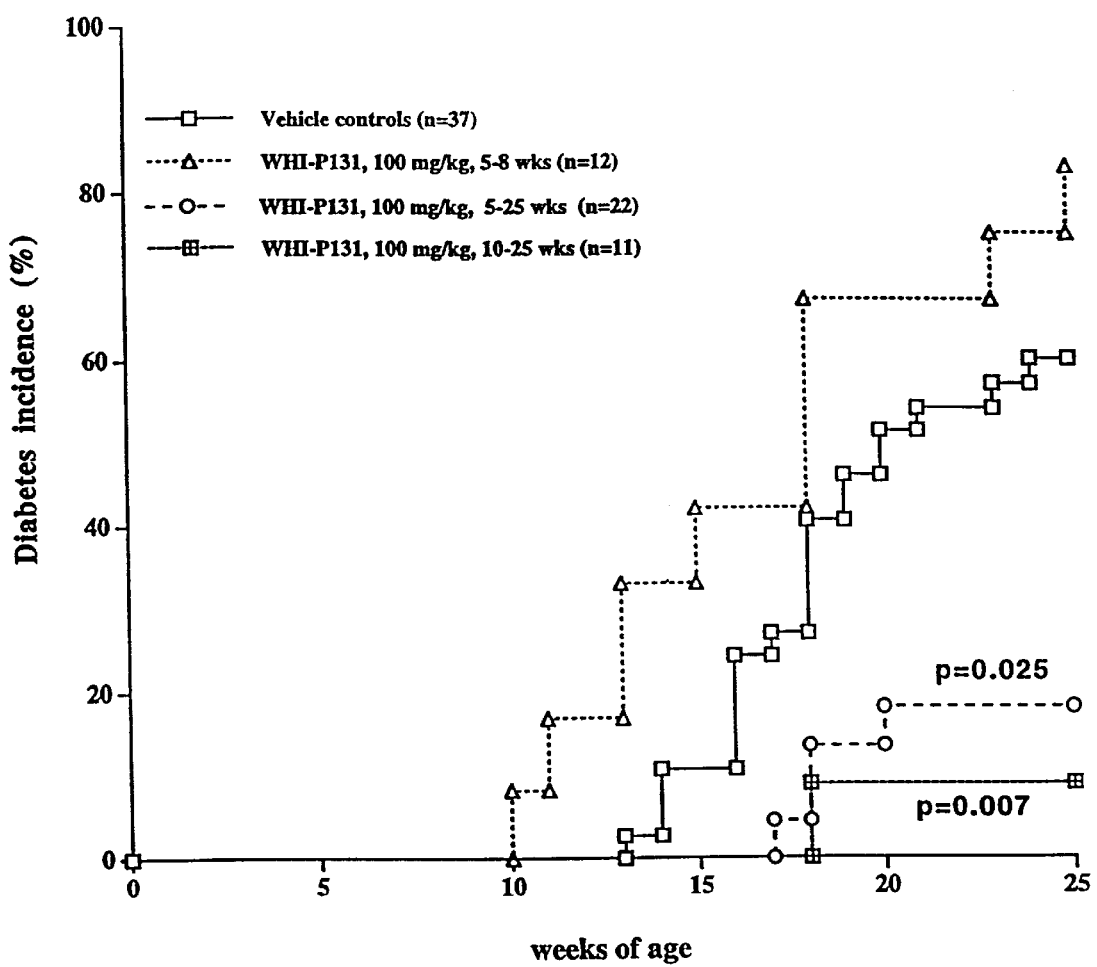
FIG. 32. Diabetes incidence in NOD females treated with 100 mg/kg of WHI-P131 from 5 or 10 to 25 wk of age; statistically significant differences between WHI-P131-treated and control mice were obtained by life table analysis (Mantel-Cox test).
Figure 33:
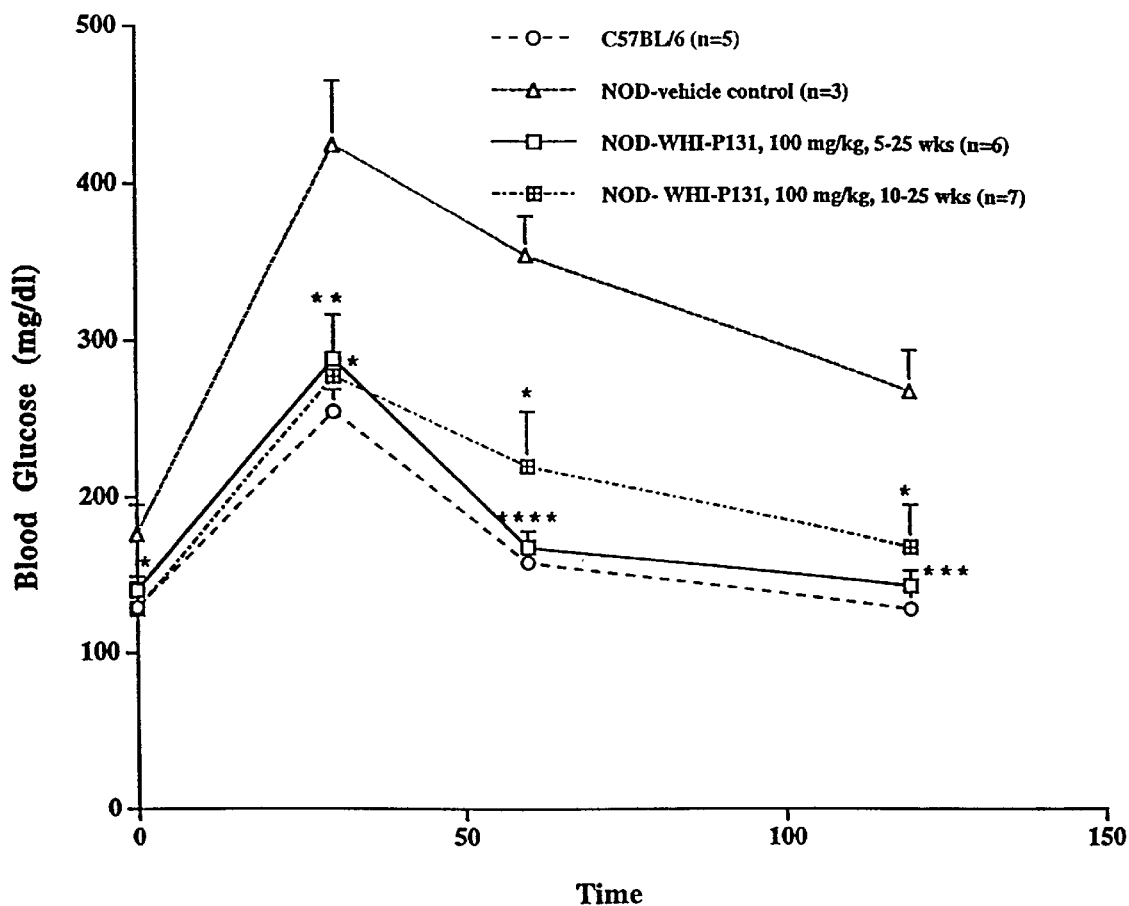
FIG. 33. IPGTT test performed in C57BL/6 females (20-wk-old), non-diabetic control NOD females (25 -wk-old) and NOD females (25-wk-old) treated for 15 or 20 weeks with 100 mg/kg of WHI-P131; statistical differences obtained by Student's t-test: *, , *, **** p<0.05, 0.01, 0.005 and 0.0001, respectively, compared to NOD vehicle-control group.

Inhibition of diabetes development in LDSTZ model of disease by JAK 3 kinase inhibitor WHI-P131. Daily treatment of C57BL-6 males by 100 mg/kg of WHI-P131 (2 doses) i.p., initiated from the first day of STZ injections, inhibited the development of LDSTZ diabetes (FIG. 29). While 20/38 (52.6%) of control mice developed diabetes on day 7, followed by 32/38 (84.2%) of diabetic mice on day 9 and 36/38 (97.4%) of diabetic mice on day 11 post first STZ injection, only 4/20 (20%) WHI-P131-treated mice became diabetic on day 7, followed by 10/20 (50%) on day 9 and 13/20 (65%) on day 11 (FIG. 29). FIG. 30 shows that WHI-P131-treated mice exhibited significantly lower (p=0.027) blood glucose level throught entire experimental period compared to the control mice.

Prevention of IDDM development in NOD females by WHI-P131 treatment. The diabetes incidence in NOD females treated daily with: a) 20 and 50 mg/kg of WHI-P131 from 5 to 25 wks of age (FIG. 27), and b) 100 mg/kg of WHI-P131 from 5 to 8, 5 to 25 and 10–25 wks of age (FIG. 28) was studied. While diabetes appeared at 13 wks of age in DMSO-treated mice (control), the WHI-P131- (50 mg/kg) treated mice started to develop diabetes at 22 wks of age (FIG. 27). At 25 wks, 22/37 (60%) of control mice became diabetic, while only 2/11 (18%) of NOD females treated with 50 mg/kg of WHI-P131 developed diabetes (p=0.017). Daily treatment with 20 mg/kg of WHI-P131 did not show protective effect on diabetes development - 5/9 (56%) of treated mice developed diabetes till 18 wks of age (FIG. 27). We asked whether short course of treatment with 100 mg/kg of WHI-P131, from wks 5 to 9 of life, could have a lasting protective effect. FIG. 28 shows that such treatment did not result with the protection from diabetes development—diabetes started at 10 wks and by 25 wks of age 10/12 (83%) of NOD females became diabetic. Then, it was studied whether later beginning of treatment (at 10 wks of age) with 100 mg/kg of WHI-P131 could be effective in the prevention of diabetes. FIG. 28 shows that treatment with 100 mg/kg of WHI-P131, initiated at 10 wks of age, is as effective as treatment initiated earlier, at 5 wks of age—diabetes incidence reached 9% (1/11) at 25 wks of age under the first treatment (p=0.007 compared to controls) and 18% (4/22) under the later one (p=0.025 compared to controls).

Group of normoglycemic NOD females treated with DMSO (n=3) or with 100 mg/kg of WHI-P131 for 20 (n=6) or 15 weeks (n=7) was fasted on the end of experimental period (at 25 wks of age) and IPGTT was performed. Non-diabetic, non-treated C57BL-6 mice (n=5) were used as controls in IPGTT test, as well. The results—blood glucose levels were similar between the C57BL/6 mice and both groups of WHI-P131-treated NOD mice during 120 min time period post glucose challenge. In contrast, normoglycemic DMSO-treated mice exhibited a significantly higher blood glucose level at each observed time point then either of WHI-P131-treated groups.

Further, histological examination of the insulitis level of the pancreata obtained from the mice analyzed in IPGTT was done. Insulitis score of controls (n=3) was 1.43±0.15, while insulitis score of NOD females treated by WHI-P131 from 5–25 wks of age was significantly (p=0.026) lower - 0.86±0.12. However, insulitis score of NOD females treated by WHI-P131 from 10–25 wks of age was not different from controls (1.42±0.24).

Figure 34:
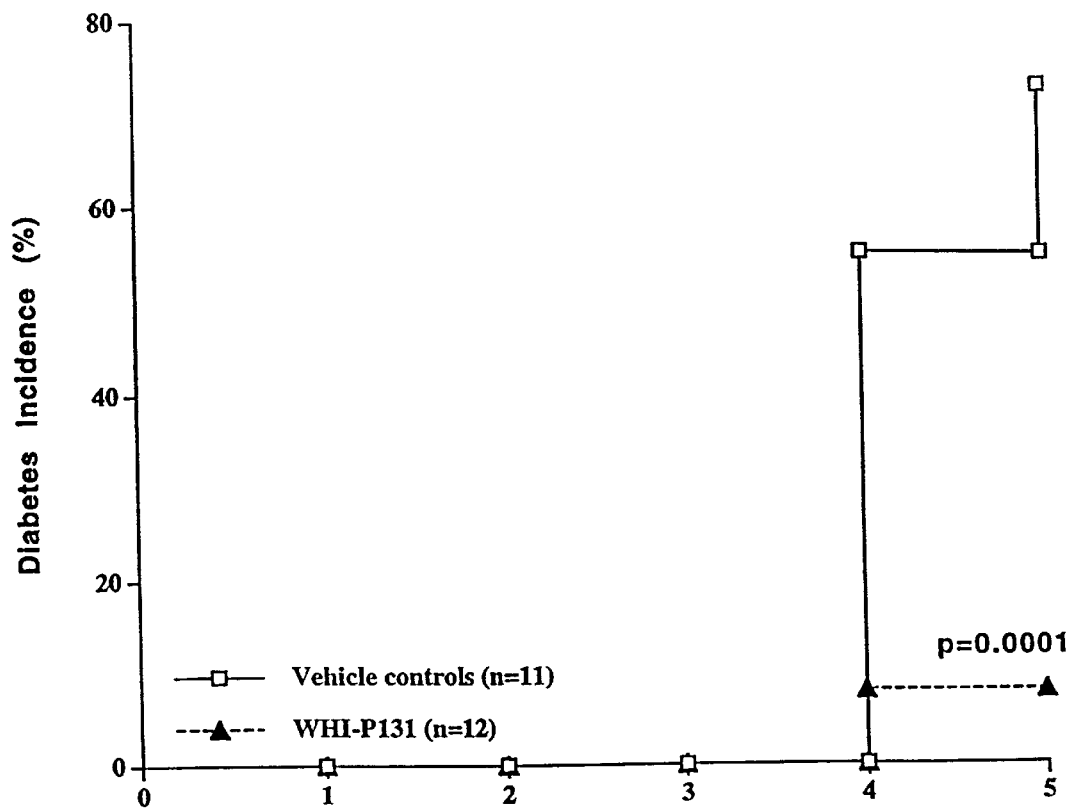
FIG. 34. Delayed adoptive transfer of diabetes into NOD-scid females by WHI-P131 treatment. NOD-scid females were transferred with $10 \times 10^6$ diabetic splenocytes and treated daily with 50 mg/kg of WHI-P131 i.p. till diabetes onset. Statistically significant difference obtained by life table analysis (Mantel-Cox test).

Prevention of diabetes development in adoptively transferred NOD-scid/scid females by WHI-P131 treatment. As WHI-P131 showed capability to prevent diabetes development in NOD females during the prediabetic phase of spontaneous development of type I diabetes, next we wanted to determine whether WHI-P131 was capable of suppressing effectors from already diabetic mice in transferring disease to NOD-scid mice. Two groups of NOD-scid females were adoptively transferred with $1 \times 10^7$ splenocytes from diabetic NOD females and one group was treated daily from the day of transfer with 50 mg/kg of WHI-P131 (n=12), while another one was treated by 10% DMSO (n=11) (FIG. 34). While 6/11 (55%) of control NOD-scid became diabetic at 4 wk, followed by 8/11 (73%) of diabetic mice at week 5 post adoptive transfer, only 1/12 (8%) of WHI-P131—treated NOD—scid females became diabetic in the same experimental period (FIG. 4). Clearly, diabetes development post adoptive transfer was significantly (p<0.002) prevented by WHI-P131 treatment.

The ability of a compound to prolong allograft survival can be determined using assays that are known in the art, or can be determined using assays similar to those described in Example 8.

Example 8

Prolongation of Allograft Survival Without Impairment of Islet Cell Function

Male C57BL/6 mice ($H-2^b$) 8–12-wk-old were used as recipients and BALB/c ($H-2^d$) males of the same age were used as a donors. Both strain of mice were purchased at Taconic, Germantown, N.Y., and housed under pathogen-free conditions in Animal care facility of Hughes Institute. Jak3$^{-/-}$ (C57BL/6×129/Sv, $H-2^b$) mice, homologous for disrupted Jak 3 gene were generous gift of Dr. J. N. Ihle, St. Jude Children's Research Hospital, Memphis, Tenn. A homozygous Jak3$^{-/-}$ mice were bred to C57BL/6 mice and the offspring of the F1 generation were backcrossed to C57BL/6 mice. After three generations of backcrossing to C57BL/6, the offspring were intercrossed to produce Jak3$^{-/-}$ and wild-type (WT)Jak 3$^{+/+}$ mice. 10–12-wk-old Jak3$^{-/-}$ and WT males were used as recipients of BALB/c islets.

Mixed lymphocyte reaction (MLR). For MLR assay, responder cells (splenocytes obtained from 10-wk-old C57BL/6 males) were plated in triplicates in 96-well-plates in the concentration of $4 \times 10^5/100$ μl of RPMI (Life Technologies, Grand Island, N.Y.) with addition of 10% fetal bovine serum (Laboratories Inc., Logan, Utah). Mitomycin-treated stimulators (splenocytes obtained from 10–12-wk-old BALB/c males) were added in the concentration of $8 \times 10^4$ in 50 μl. WHI-P131 was added in different concentrations to a final volume of 200 μl and cells were cultured in 5% CO2 with humidified air in an incubator at 37° C. for 5 days. Then, a calorimetric assay for the quantification of cell proliferation, based on the cleavage of the tetrazolium salt WST-1 by mitochondrial dehydrogenases in viable cells (Boehringer Mannheim, Indianapolis, Ind.), was performed following manufacturer's instructions. The absorbance was measured at 450/690 nm on a Multiskan MS microplate scanner. The value of cell proliferation was obtained by diminishing O.D. value of proliferation of stimulated cells by O.D. value of non-stimulated cells (O.D. values of non-stimulating cells were between 0.370–0.450).

Apoptosis detection. C57BL6 splenocytes ($3 \times 10^6$/ml) were cultured in 24-well plate for 20 h in 500 µl of RPMI-1640 under the conditions described above. WHI-P131 was added in the concentrations of 0.1, 1, 10 and 100 µg/ml. Apoptotic cell death was detected by TUNEL, using InSitu Cell Detection Kit, Fluorescein (Boehringer Mannheim, Indianapolis, Ind.). After the culture period, cells were washed, fixed, permeabilised and stained following manufacturer's instructions and apoptosis was analyzed by flow cytometry, using FACS Calibur (Becton Dickinson, San Jose, Calif.).

Flow cytometric (FACS) analysis. Single cell suspension of splenocytes was prepared from WHI-P131- (130 mg/kg/day) or vehicle-treated C57BL/6 mice, red blood cells were lysed by lysis buffer and splenocytes ($1 \times 10^6$) were stained with 1:100 dilution of following anti-mouse monoclonal antibodies (Ab): anti-CD3-FITC Ab (clone 145-2C11), anti-CD4-FITC Ab (clone GK 1.5), anti-CD8-PE Ab (clone 53-6.7) and anti-CD19-PE Ab (clone 1D3). All Abs were purchased from Pharmingen, San Diego, Calif. Stained splenocytes were analyzed by FACS Calibur, as described above.

Islet isolation. Islets of Langerhans were isolated from BALB/c males by the bile duct perfusion with 3–4 ml of collagenase P (3 mg/ml) (Boehringer Mannheim, Indianapolis, Ind.) and deoxyribonuclease (0.1 mg/ml) (Sigma, St. Louis, Mo.), as described previously Cetkovic-Cvrlje M, et al., 1997, Diabetes, 46: 1975–1982). Islets were hand-picked 3–4 times under the dissecting scope before islets were free of exocrine tissue, vessels, lymph nodes and ducts and ready for transplantation.

Allogeneic islet transplantation and drug treatment. Four hundred islets were placed in Hamilton syringe and transplanted under the left kidney capsule of each diabetic recipient mouse. Recipients were rendered diabetic with a single i.p. dose of streptozotocin (200 mg/kg; Sigma, St. Louis, Mo.) 1 wk before transplantation. Blood glucose level was measured by One Touch Profile glucose monitor system (Lifescan, Milpitas, Calif). Only diabetic mice with glycemia over 350 mg/dl were used as transplant recipients. Allograft function was monitored by serial blood glucose measurements. Primary graft function was defined as a blood glucose under 200 mg/dl on day 3 post transplantation and graft rejection was defined as a rise in blood glucose exceeding 250 mg/dl on two consecutive measurements, following a period of primary graft function. Recipients were treated daily with high-dose (20 mg/kg) of cyclosporine A (Sigma, St. Louis, Mo.), WHI-P131 (50 and 75 mg/kg, divided in three doses), WHI-P132 (50 mg/kg, divided in three doses) or with vehicle control from the day of transplantation until the day of rejection. All injections were given i.p.

Intraperitoneal glucose tolerance test (IPGTT) in syngeneic islet transplant recipients. IPGTT was performed in C57BL/6 recipients that were transplanted with syngeneic islet grafts (400 C57BL/6 islets) and treated with WHI-P131 or vehicle control for two months. Mice were fasted for 10 hours, and the glucose solution (1.5 g/kg body weight) was injected i.p. Before and after injection of glucose, blood samples were taken and blood glucose levels were measured (as described above) at 0, 30, 60 and 120 min time points.

Histopathological studies. The vehicle control— (n=3) and WHI-P131—treated C57BL/6 recipients (n=5) of islet allograft were sacrificed on day 14 post transplantation; Jak3$^{-/-}$ recipients (n=6) were sacrificed on day 100 post transplantation; the C57BL/6 recipients of syngeneic islets — vehicle control— (n=4) and WHI-P131-treated (n=5) were sacrificed on day 180 post transplantation. Kidneys bearing grafts were removed, fixed in 10% formalin and embedded in paraffin. Serial sections of graft area were cut and stained with hematoxylin and eosin. For insulin staining, sections were stained by immunoperoxidase method using 1:100 dilution of polyclonal guinea pig anti-insulin antibody (Gpx Insulin, Dako, Carpinteria, Calif.) and 1:100 dilution of secondary antibody conjugated to horse radish peroxidase (Guinea Pig Inmunoglobulins HRP, Dako, Carpinteria, Calif.). Sections were briefly counterstained with hematoxylin and mounted for light microscopic examination.

Statistical analysis. Statistical analysis was done by using unpaired Student's t-test (MLR and FACS data). Experimental differences in allograft rejections between the drug-treated and control groups were assessed by the Kaplan-Meier life table analysis using Mantel-Cox test. The p value <0.05 was considered as statistically significant.

Results for Example 8.

Figure 35:
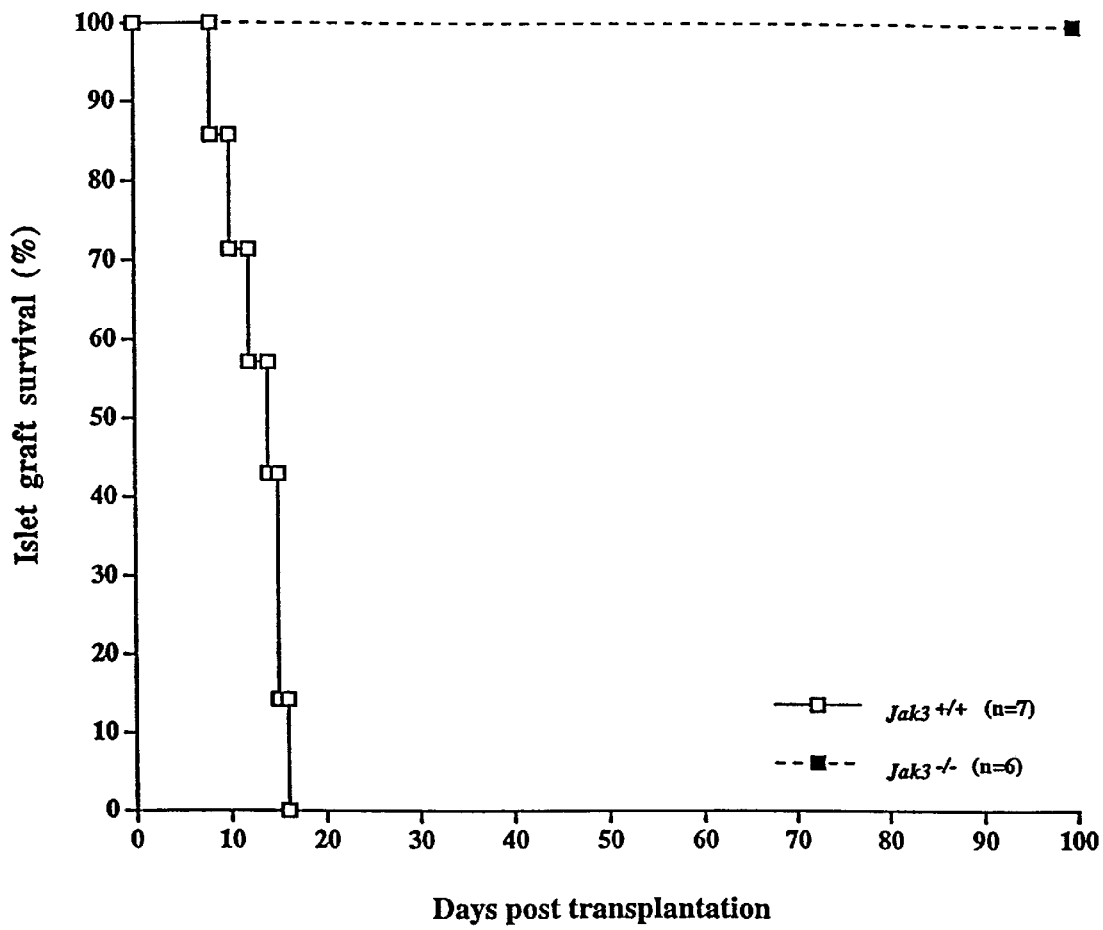
FIG. 35. Jak3$^{-/-}$ mice do not reject islet allograft (A); hematoxilin and eosin (B) and immunostaining for insulin (C) of allogeneic islet graft transplanted under the kidney capsule of diabetic Jak3$^{-/-}$ recipient sacrified on day 100 post transplantation. Data representative of >30 sections/graft and 6 mice/group; ×10.

Jak3$^{-/-}$ mice do not reject islet alograft JAK3-deficient males (n=6) and their WT littermates (n=7), rendered diabetic by STZ, were transplanted with BALB/c islets under the kidney capsule and blood glucose level was followed for 100 days post transplantation. While islet allografts of WT controls were rejected with a MST of 12.9±1.1 days, all islet allografts of Jak3$^{-/-}$ recipients survived 100 days post transplantation (FIG. 35). Histological analysis of grafts showed no infiltration (data not shown) to slight mononuclear infiltration of graft area with completely preserved islet morphology.

Figure 36:
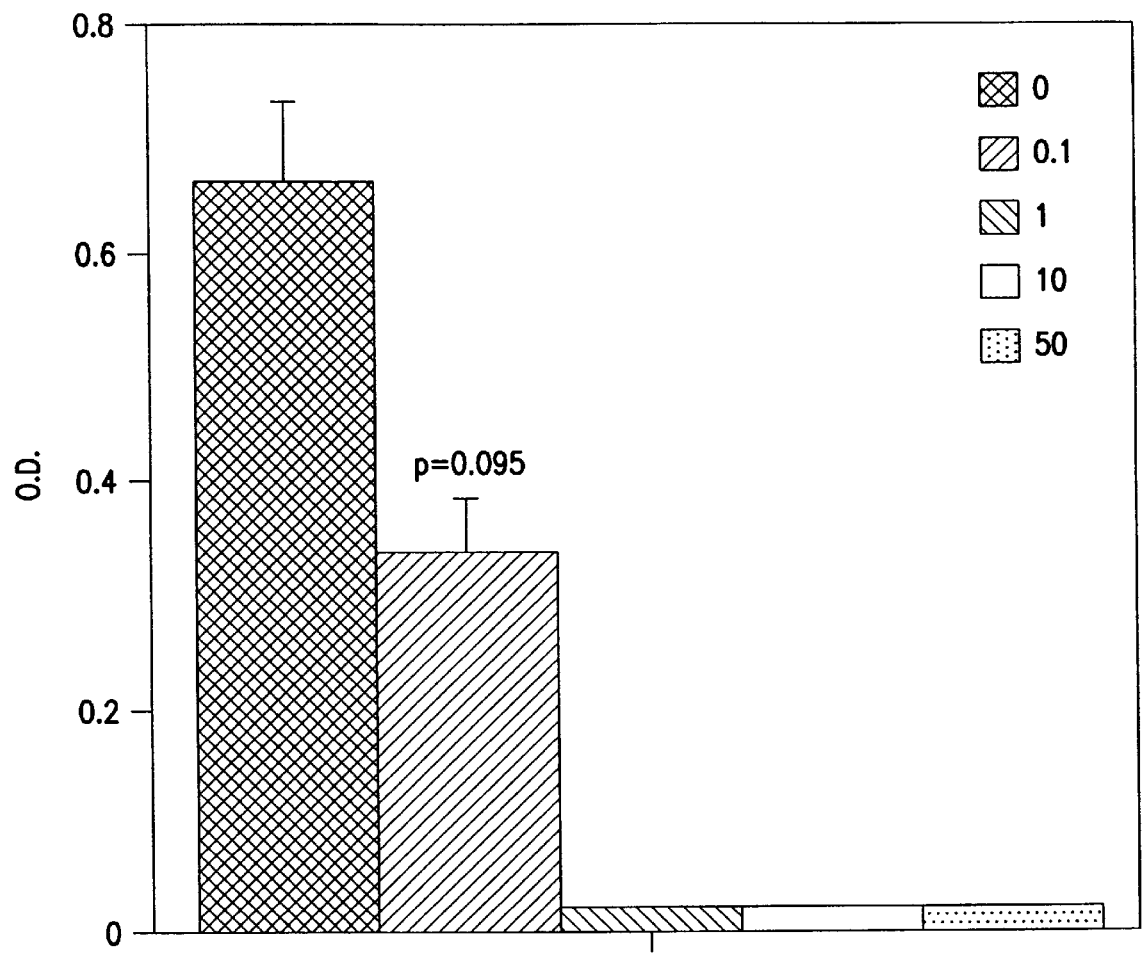
FIG. 36. WHI-P131 supresses MLR reaction. Responder splenocytes ($4 \times 10^6$/ml) were mixed with stimulator splenocytes ($1.6 \times 10^6$/ml) and drugs were added in the concentration of 0.1, 1, 10 and 50 •g/ml during the 5-day-culture period. Proliferation was measured by WST-1 colorimetric assay. Results are presented as mean O.D.±SEM of 6 separate experiments; p=0.0095 compared to proliferation of control cells not-exposed to the WHI-P131.
Figure 37:
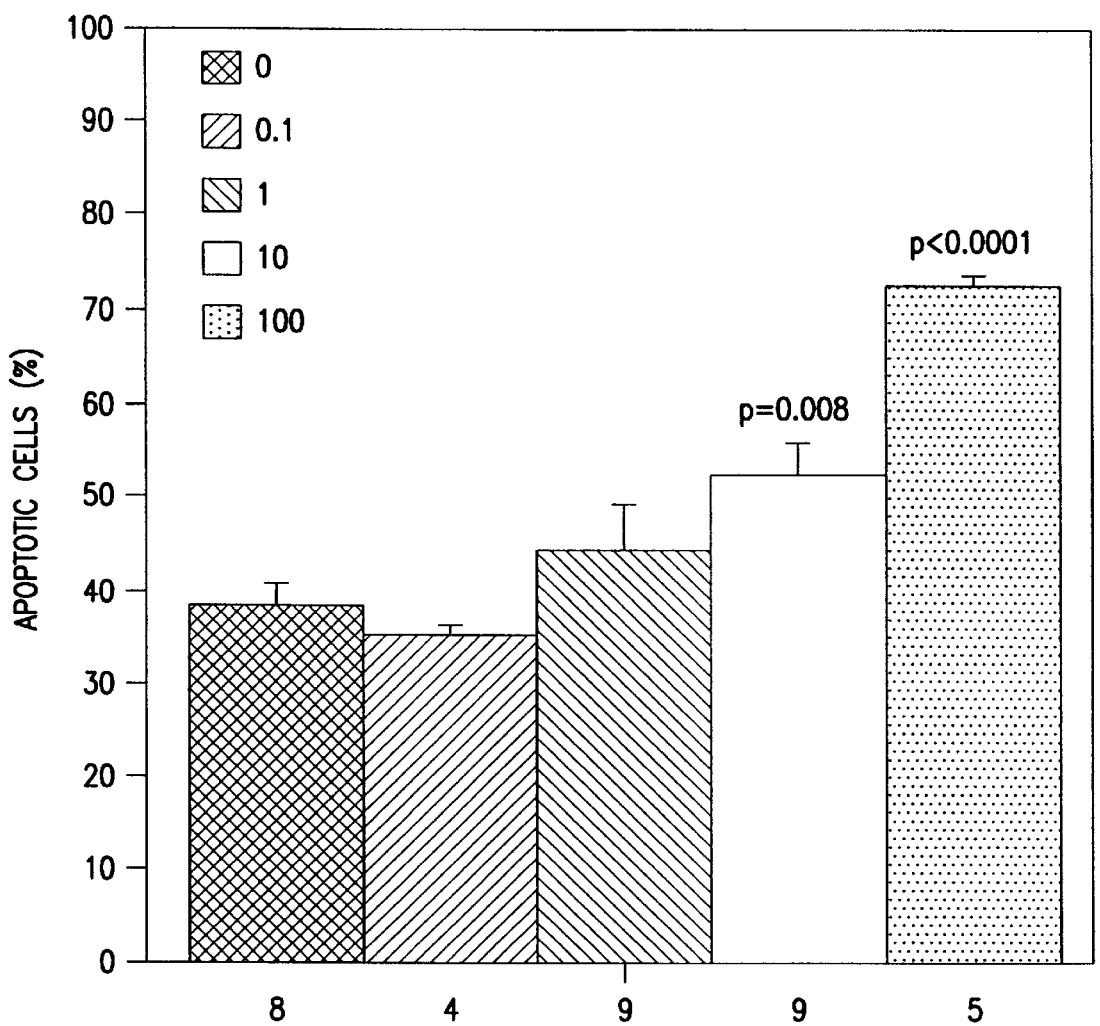
FIG. 37. Flow cytometry analysis of apoptotic splenocytes (TUNEL-positive). TUNEL staining was performed after 20 h incubation period of splenocytes ($1.5 \times 10^6$) with 0.1, 1, 10 and 100 $\mu$g/ml of WHI-P131. Results are presented as mean±SEM. Statistical differences between the groups analyzed by Student's t-test.

WHI-P131-induced inhibition of MLR response. WHI-P131, added in the concentration of 0.1, 1, 10 and 50 µg/ml, inhibited proliferation of alloreactive splenocytes in MLR in a dose-dependent manner (FIG. 36). While the concentration of 0.1 •g/ml of WHI-P131 induced statistically significant (p=0.0095) reduction of MLR response, complete abrogation of the response (obtained O.D. values were below the O.D. level of non-stimulating controls) was obtained with addition of 1 µg/ml of WHI-P131 (FIG. 36). Next we tested whether WHI-P131-induced lymphocyte death was the reason for inhibited MLR response. Therefore, apoptotic splenocytes (TUNEL-positive) were determined after the culture period of 20 h with addition of different concentrations of WHI-P131. FIG. 37 shows that apoptotic cell death of splenocytes cultured with addition of 0.1 and 1 µg/ml of WHI-P131 does not differ from control cells, while addition of 10 and 100 µ/ml significantly increased (p=0.008 and p<0.0001, respectively) apoptotic cell death in comparison to control cell death during the observed culture period. Therefore, WHI-P131 effects on MLR suppression, obtained with lower concentration of the drug (0.1 and 1 µg/ml), seems to not be caused by the induction of cell death.

Figure 38:
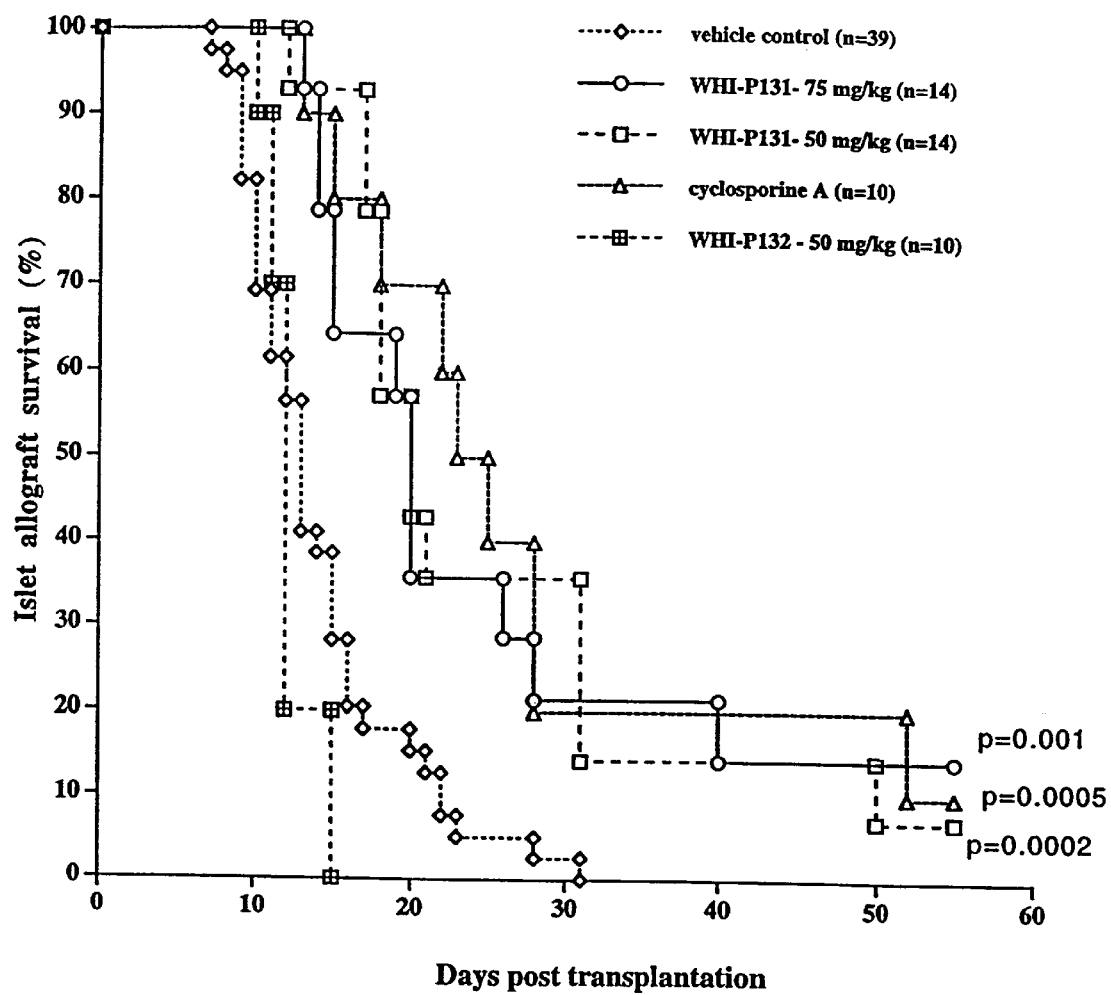
FIG. 38. Effect of WHI-P131- (50 and 75 mg/kg), WHI-P132 (50 mg/kg) and cyclosporine A-treatment (20 mg/kg ) on islet allograft survival; p values obtained by life table analysis (Mantel-Cox test).

WHI-P131 treatment of recipients prolonged islet allograft survival. The control C57BL/6 mice (n=39) rejected BALB/c islet allograft with a mean survival time (MST) of 14.1±0.9 days. Daily treatment of recipients (n=10) with high-dose—20 mg/kg—of CsA (18) significantly increased (p=0.0005) allograft survival (MST=27.9±4.6 days) (FIG. 38). Treatments with 50 mg/kg (n=14) or 75 mg/kg (n=14) of WHI-P131 were as effective as CsA treatment in prolongation of allograft survival (MST=24.7±3.4 and 25.3±3.8, respectively) in comparison to controls (p=0.0002 and 0.001, respectively) (FIG. 38).

Histologic examination of the islet allografts that were harvested at 14 days post transplantation from normoglycemic recipients treated with vehicle control (n=3) showed lymphocytic invasion and massive islet destruction, clearly seen with immunostaining for insulin. This finding is in striking contrast with allografts from recipients treated with 50 mg/kg of WHI-P131 (n=5), in which lymphocytic infiltration was present but without extensive destruction of islets. The hyperglycemic vehicle-treated allografts (n=4), harvested at the same time point, were completely invaded by lymphocytes with no remaining insulin-producing cells.

Figure 39:
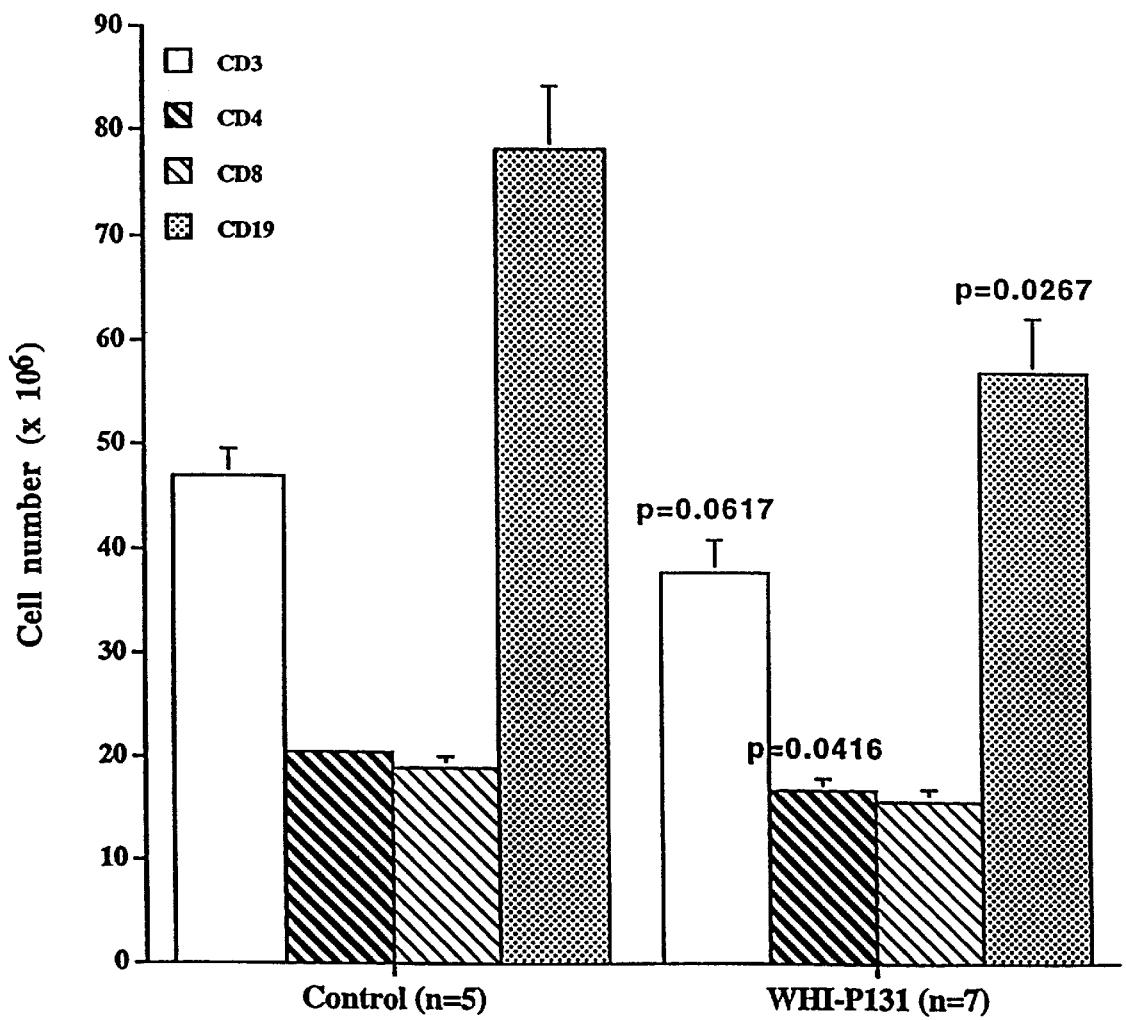
FIG. 39. Flow cytometry analysis of C57BL/6 splenocytes after the treatment with 130 mg/kg of WHI-P131 for 10 days. Results are presented as mean±SEM. Statistical differences between the groups analyzed by Student's t-test.

The next experiment was performed with an aim to study the effects of WHI-P131 treatment on splenocyte populations in vivo. C57BL/6 males were treated with 130 mg/kg of WHI-P131 (n=7) and with vehicle control (n=5) for 10 days. Total number of splenocytes was $154\pm8.5\times10^6$ in vehicle-treated controls, while reduced number of splenocytes $-119\pm9.4\times10^6$ was found in WHI-P131-treated mice (p=0.025). There were no differences in the percentages of CD3+, CD4+ and CD8+T-cells and CD19+B-cells between the WHI-P131- and vehicle-treated mice (data not shown). However, FIG. 6 shows that slight differences in the number of studied cell populations between the WHI-P131-treated and control groups were found. Thus, the number of CD3+ splenocytes was reduced to $37.7\pm3.2\times10^6$ (however, not statistically significant, p=0.0617) in WHI-P131-treated mice in comparison to $46.9\pm2.6\times10^6$ in controls. The number of CD4+T-cells—$16.8\pm1.2\times10^6$ (p=0.0416), as well as B-cells—$57.1\pm5.3\times10^6$ (p=0.0267) were reduced in WHI-P131-treated mice compared to the controls—$20.5\pm0.6\times10^6$ and $78.2\pm6.1\times10^6$, respectively (FIG. 39).

Figure 40:
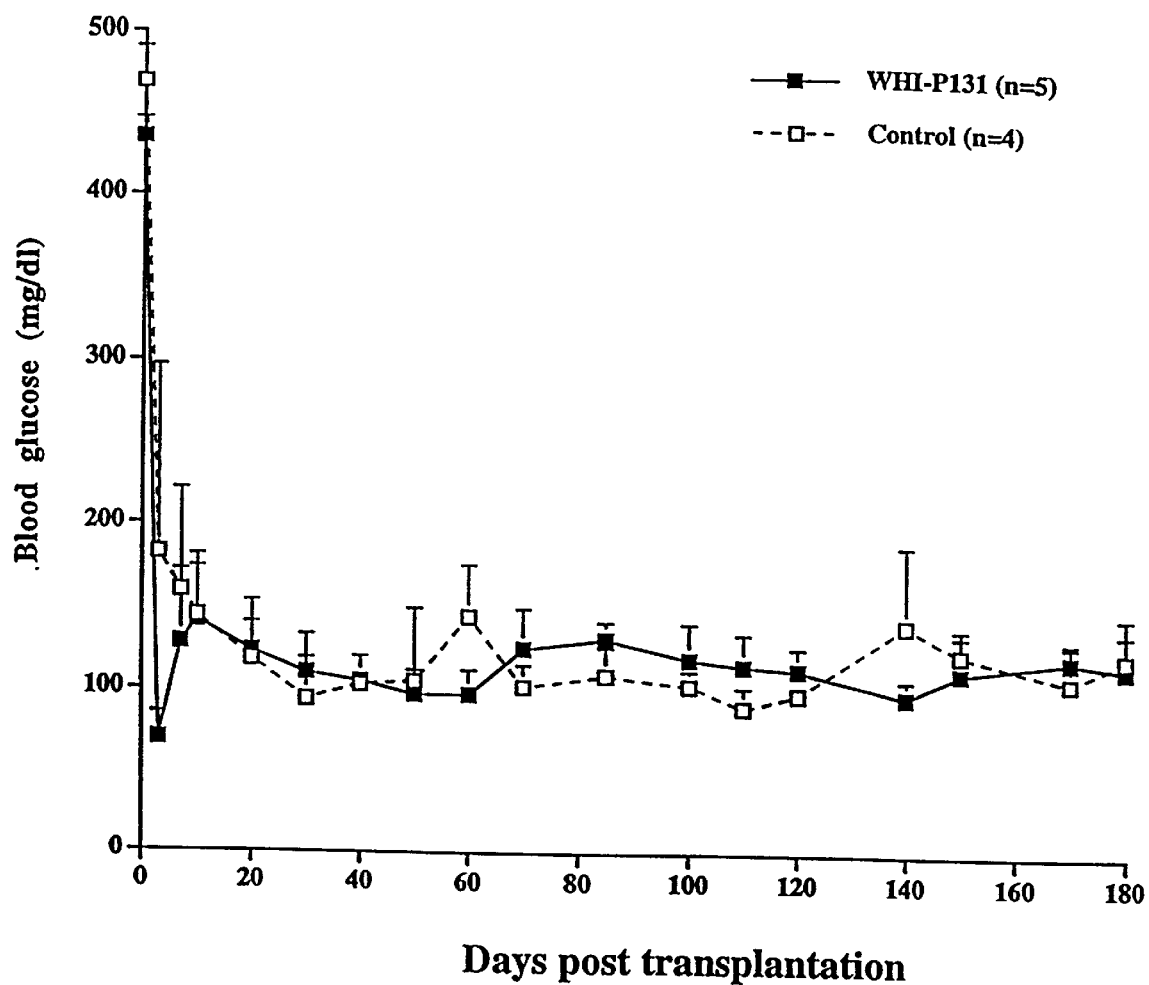
FIG. 40. Non-fasting blood glucose (mg/dl) in syngeneic islet transplant recipients treated with 50 mg/kg/day of WHI-P131 or vehicle control during the period of 180 days post transplantation (A). Results are presented as mean±SD.
Figure 41:
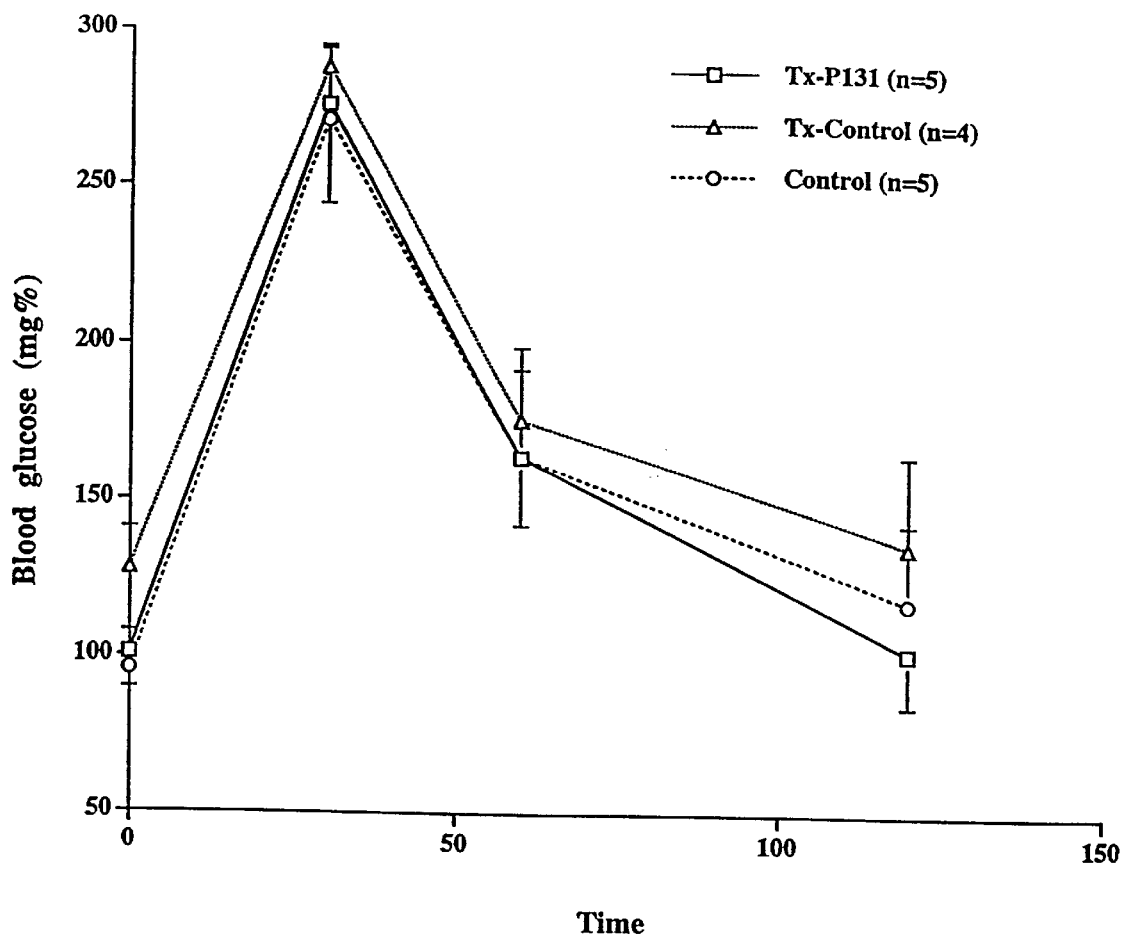
FIG. 41. IPGTT of the same recipients in FIG. 39 and non-transplanted control mice performed on day 70 (B) post transplantation after the fasting period of 8 hours. Results are presented as mean±SEM (B, C).
Figure 42:
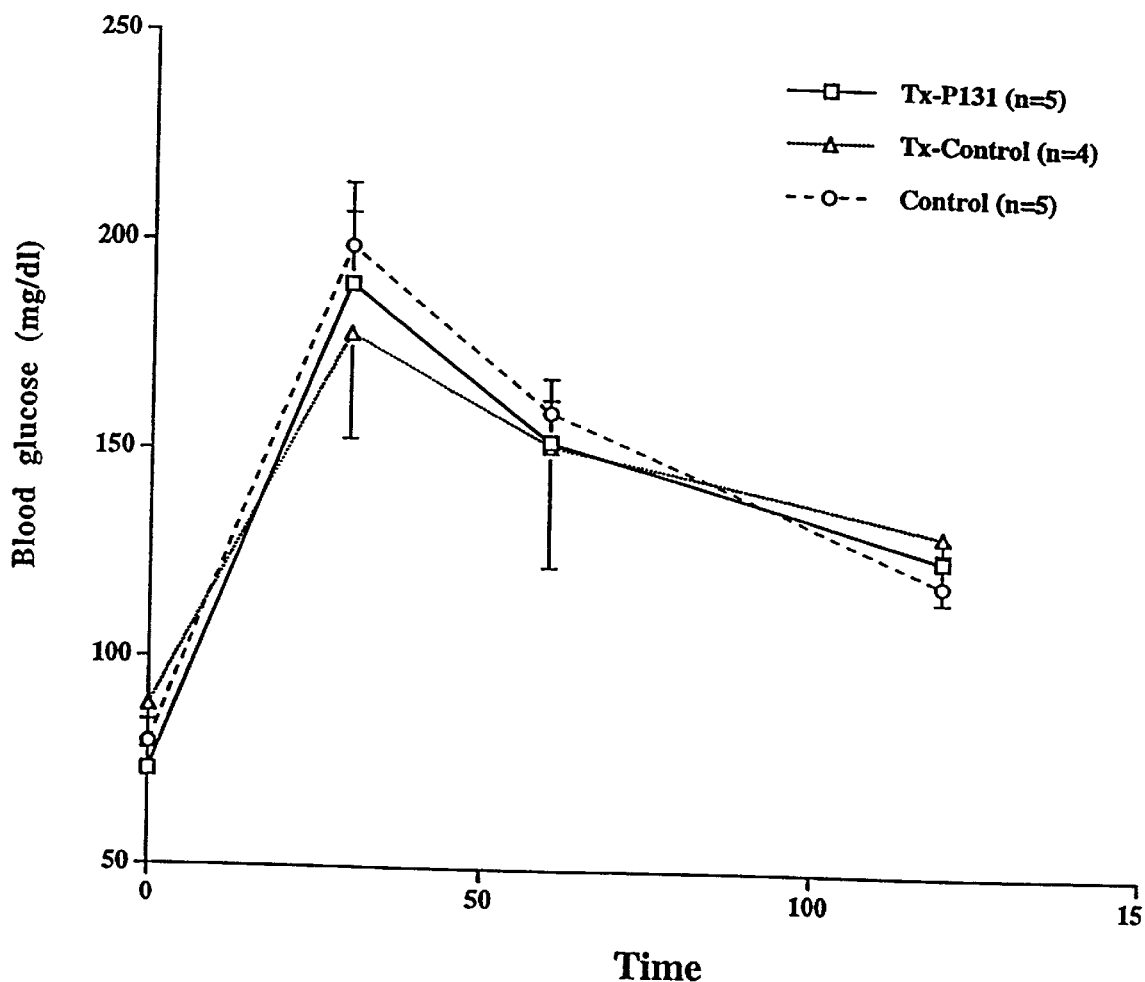
FIG. 42. IPGTT of the same recipients in FIG. 39 and non-transplanted control mice performed on day 180 (C) post transplantation after the fasting period of 8 hours. Results are presented as mean±SEM.

Function of transplanted syngeneic islets is preserved after the long-term treatment with WHI-P131. This study was performed to test the effect of long-term treatment (180 days) with 50 mg/kg of WHI-P131 on syngeneic islet graft function. As it could be seen on FIG. 40, non-fasting blood glucose level did not differ during the entire experimental period of 180 days post transplantation between the vehicle control— (n=4) and WHI-P131 -treated (n=5) syngeneic recipients. IPGTT was performed on day 70 of treatment. The nonfasting blood glucose of the controls and P131-treated recipients at that time was $102.0\pm6.7$ and $124.6\pm10.8$ mg/dl, respectively. IPGTT test showed that there was no significant difference in islet function of non-transplanted, non-treated C57BL/6 males, transplanted vehicle-treated recipients (controls) and transplanted WHI-P131 -treated recipients (FIG. 41). Another IPGTT test was performed on the end of experimental period (day 180 post transplantation). The non-fasting blood glucose level at that time was $120.9\pm12.5$ in vehicle control— and $115.2\pm9.2$ mg/dl in WHI-P131-treated recipients. IPGTT test showed again that islet function of WHI-P131-treated recipients was not different from islet function of either control recipients or non-transplanted C57BL/6 mice.

Representative examples from the light microscopical evaluation of the vehicle control— and WHI-P131-treated syngeneic islet grafts are illustrated in FIG. 8. Hematoxylin and eosin staining of vehicle control and WHI-P131-treated grafts showed that there were no significant morphological changes between them. Immunohistochemical analysis confirmed that insulin expression in WHI-P131-treated grafts was comparable to that of the grafts of the vehicle control-treated recipients.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method of treating diabetes comprising:
   a) transplanting insulin producing cells into a mammal in need thereof; and
   b) administering to the mammal an effective transplant rejection inhibiting amount of a compound 4-(4-hydroxyl-phenyl)-amino-6,7-dimethoxyquinazoline; or a pharmaceutically acceptable salt thereof.

* * * * *

UNITED STATES PATENT AND TRADEMARK OFFICE
CERTIFICATE OF CORRECTION

PATENT NO.     : 6,495,556 B2                                              Page 1 of 1
DATED          : December 17, 2002
INVENTOR(S)    : Uckun et al.

It is certified that error appears in the above-identified patent and that said Letters Patent is hereby corrected as shown below:

<u>Title page,</u>
Item [75], Inventors, "White Bear Leak" should read -- White Bear Lake --
Item [56], References Cited, OTHER PUBLICATIONS, In the Fujii, H. et al. reference, "The Histrochemical Journal" should read -- The Histochemical Journal --
"Tuel, Ahlgren, L. et al.," should read -- Tuel-Ahlgren, L. et al. --

Signed and Sealed this

Twenty-second Day of April, 2003

JAMES E. ROGAN
*Director of the United States Patent and Trademark Office*